(12) United States Patent
Lanzavecchia

(10) Patent No.: US 9,073,981 B2
(45) Date of Patent: Jul. 7, 2015

(54) DENGUE VIRUS NEUTRALIZING ANTIBODIES AND USE THEREOF

(75) Inventor: Antonio Lanzavecchia, Bellinzona (CH)

(73) Assignee: Institute for Research in Biomedicine, Bellinzona (CH)

(*) Notice: Subject to any disclaimer, the term of this patent is extended or adjusted under 35 U.S.C. 154(b) by 716 days.

(21) Appl. No.: 13/124,076

(22) PCT Filed: Oct. 13, 2009

(86) PCT No.: PCT/IB2009/007372
§ 371 (c)(1),
(2), (4) Date: Aug. 16, 2011

(87) PCT Pub. No.: WO2010/043977
PCT Pub. Date: Apr. 22, 2010

(65) Prior Publication Data
US 2012/0020957 A1    Jan. 26, 2012

Related U.S. Application Data

(60) Provisional application No. 61/104,911, filed on Oct. 13, 2008.

(51) Int. Cl.
*C07K 16/10* (2006.01)

(52) U.S. Cl.
CPC ......... *C07K 16/1081* (2013.01); *C07K 2317/21* (2013.01); *C07K 2317/56* (2013.01); *C07K 2317/565* (2013.01); *C07K 2317/71* (2013.01); *C07K 2317/76* (2013.01)

(58) Field of Classification Search
CPC ........... C07K 16/1081; C07K 2317/21; C07K 2317/565; C07K 2317/71; C07K 2317/56
USPC ................. 424/159.1, 218.1; 435/328, 339; 535/387.3, 388.15, 389.4, 23.53
See application file for complete search history.

(56) References Cited

U.S. PATENT DOCUMENTS

| | | | |
|---|---|---|---|
| 4,179,337 | A | 12/1979 | Davis |
| 4,495,285 | A | 1/1985 | Shimizu |
| 4,609,546 | A | 9/1986 | Hiratani |
| 4,676,980 | A | 6/1987 | Segal et al. |
| 4,766,106 | A | 8/1988 | Katre et al. |
| 4,831,175 | A | 5/1989 | Gansow et al. |
| 5,595,721 | A | 1/1997 | Kaminski et al. |
| 5,807,715 | A | 9/1998 | Morrison et al. |
| 6,300,104 | B1 | 10/2001 | Morrison et al. |
| 2004/0209244 | A1* | 10/2004 | Burton et al. ............ 435/5 |
| 2013/0344058 | A1* | 12/2013 | Goncalvez et al. ....... 424/133.1 |

FOREIGN PATENT DOCUMENTS

| WO | 0052031 A2 | 8/2000 |
|---|---|---|
| WO | 0052473 A2 | 8/2000 |
| WO | 2004003019 A2 | 1/2004 |
| WO | WO 2004/003019 | * 6/2004 |
| WO | 2004067567 A2 | 8/2004 |
| WO | 2004076677 A2 | 10/2004 |
| WO | 2005056600 A2 | 6/2005 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Recher et al. (Curr. Op. Microbiol. 7(4): 426-433 (Aug. 2004)).*
Hessell et al. (Nature 449:101-104 (2007)).*
Beltramello et al., Cell Host Microbe 8(3): 1-25 (Sep. 16, 2010).*
de Alwis et al., PLOS Negl. Trop. Dis. 5(6):1-8 (Jun. 2011).*
Simonelli et al., PLOS One 8(2):1-11 (Feb. 2013).*
Williams et al., PLOS Pathog 9(2):1-17 (Feb. 2013).*
Cafiso D et al., 1981, Preparation of Unilamellar Lipid Vesicles at 37° C by Vaporization Methods, Biochimica et Biophysica Acta, 649, 129-132.
Cho M et al., 2001, An oriP expression vector containing the HIV-1 Tat/TAR transactivation axis produces high levels of protein expression in mammalian cells, Cytotechnology, 37: 23-30.
Cho M et al., 2003, Versatile Expression System for Rapid and Stable Production of Recombinant Proteins, Biotechnology Progress, vol. 19, Issue 1, pp. 229-232, 2003.
Gabizon A. et al., 1982, Liposomes as in Vivo Carriers of Adriamycin: Reduced Cardiac Uptake and Preserved Antitumor Activity in Mice, Cancer Research 42, 4734-4739.
Jones D. et al., 2003, High-Level Expression of Recombinant IgG in the Human Cell Line PER.C6, Biotechnology Progress, vol. 19, Issue 1, pp. 163-168.
Knauf MJ et al 1988 Relationship of Effective Molecular Size to Systemic Clearance in Rats of Recombinant Interleukin-2 Chemically Modified with Water-soluble Polymers, Thej Ournaolf Biologicachle Mistry, vol. 263, No. 29, pp. 15064-15070.

(Continued)

Primary Examiner — Lynn Bristol
(74) Attorney, Agent, or Firm — Dennis A. Bennett

(57) ABSTRACT

The invention relates to antibodies and antigen binding fragments thereof and to cocktails of antibodies and antigen binding fragments that neutralize dengue virus infection without contributing to antibody-dependent enhancement of dengue virus infection. The invention also relates to immortalized B cells that produce, and to epitopes that bind to, such antibodies and antigen binding fragments. In addition, the invention relates to the use of the antibodies, antigen binding fragments, and epitopes in screening methods as well as in the diagnosis and therapy of dengue virus infection.

11 Claims, 2 Drawing Sheets

(56) References Cited

OTHER PUBLICATIONS

Kohler G and Milstein C., 1975, Continuous cultures of fused cells secreting antibody of predefined specificity, Nature vol. 256, pp. 495-497.
Kozbar et al. 1983, The production of monoclonal antibodies from human lymphocytes, Immunology Today 4:72-79.
Alexander B et al., Novel human monoclonal antibody combination effectively neutralizing natural rabies virus variants and individual in vitro escape mutants, Journal of Virology, 2005, pp. 9062-9068.
Lefranc MP et al., 1997, Unique database numbering system for immunogenetic analysis Immunology Today, 18:509.
Lefranc MP et al., 2003 IMGT unique numbering for immunoglobulin and T cell receptor variable domains and Ig superfamily V-like domains, Developmental & Comparative Immunology 27(1):55-77.
Poznansky M. J. et al., 1984 Biological Approaches to the Controlled Delivery of Drugs: A Critical Review, Pharmacologiocal Reviewss vol. 36: No. 4, 277-336.
Nakowitsch S et al., HIV-1 mutants escaping neutralization by the human antibodies 2F5, 2G12, and 4E10: in vitro experiments versus clinical studies, AIDS, 2005, 19(17):1957-66.
Szoka F., 1980 Comparative Properties and Methods of Preparation of Lipid Vesicles (Liposomes), Annual Review Biophysics Engineering 9:467-508.
Traggiai E. et al., 2004, An efficient method to make human monclonal antibodies from memory B cells: potent neutralization of SARS coronavirus, Nature Medicine, EBV paper 10(8): 871-875.
Goncalvez A P et al., 2007, Monoclonal antibody-mediated enhancement of dengue virus infection in vitro and in vivo and strategies for prevention, Proceedings of the National Academy of Science USA, 104(22) : pp. 9422-9427.
Puttikhunt et al., Novel anti-dengue monoclonal antibody recognizing conformational structure of the prM-E heterodimeric complex of dengue virus, Journal Medical of Virology, 2008, 80(1):125-33.
Chambers et al., Yellow fever virus/dengue-2 virus and yellow fever virus/dengue-4 virus chimeras: biological and characterization, immunogenicity, and protection against dengue encephalitis in the mouse model, Journal of Virology 2003, 77(6):3655-3668.
Hezareh M, et al., Effector function activities of a panel of mutants of a broadly neutralizing antibody against human immunodeficiency virus type 1, Journal of Virology, 2001, 75(24):12161-8.
Rudikoff et al., Single amino acid substitution altering antigen-binding specificity, Proc Natl Acad Sci USA 1982 vol. 79 p. 1979-1983.
MacCallum et at., Antibody-antigen interactions: contact analysis and binding site topography, Journal of Molecular Biology 1996 V262 pp. 732-745.
De Pascal et al., Grafting of "abbreviated" complementarity-determining regions containing specificity-determining residues essential for ligand contact to engineer a less immunogenic humanized monoclonal antibody, The Journal of Immunology (2002) 169, 3076-3084.
Casset et al., A peptide mimetic of an anti-CD4 monoclonal antibody by rational design, 2003 BBRC 307, pp. 198-205.
Vajdos et al., Comprehensive functional maps of the antigen-binding site of an anti-ErbB2 antibody obtained with shotgun scanning mutagenesis, 2002, Journal of Molecular Biology, 320, pp. 415-428.
Holm et al., Functional mapping and single chain construction of the anti-cytokeratin 8 monoclonal antibody TS1, 2007, Molecular Immunology, 44 pp. 1075-1084.
Chen et al. Selection and analysis of an optimized anti-VEGF antibody: crystal structure of an affinity-matured Fab in complex with antigen, Journal of Molecular Biology, 1999, 293, pp. 865-881.
Wu CJ et al., Clinical significance and distribution of putative virulence markers of 116 consecutive clinical Aeromonas isolates in southern Taiwan, Journal of Molecular Biology, (1999) 294, pp. 151-162.
Brummell et al., Probing the combining site of an anti-carbohydrate antibody by saturation-mutagenesis: role of the heavy-chain CDR3 residuesBiochemistry, 1993, 32:1180-1187.
Kobayashi et al., Tryptophan H33 plays an important role in pyrimidine (6-4) pyrimidone photoproduct binding by a high-affinity antibody, 1999, Protein Engineering 12:879-844.
Burks et al., In vitro scanning saturation mutagenesis of an antibody binding pocket, PNAS 1997, 94:412-417.
Jang et al., The structural basis for DNA binding by an anti-DNA autoantibody, Molecular Immunology, 1998, 35:1207-1217.
Brorson et al., Mutational analysis of avidity and fine specificity of anti-levan antibodies,Journal of Immunology, 1999, 163:6694-6701.
Coleman PM, Effects of amino acid sequence changes on antibody-antigen interactions, Research in Immunology 19994, 145:33-36.
Ward et al., Binding activities of a repertoire of single immunoglobulin variable domains secreted from *Escherichia coli*, Nature, 1989, 341:544-546.
Smith-Gill et al., Contributions of immunoglobulin heavy and light chains to antibody specificity for lysozyme and two haptens, Journal of Immunology, 1987, 139:4135-4144.
Kumar et al., Molecular cloning and expression of the Fabs of human autoantibodies in *Escherichia coli*. Determination of the heavy or light chain contribution to the anti-DNA/-cardiolipin activity of the Fab, (Journal of Biological Chemistry, 2000, 275:35129-35136.
Song et al., Light chain of natural antibody plays a dominant role in protein antigen binding, Biochemical and Biophysical Research Communications, 2000, 268:390-394.
Recher et al., Public, private and non-specific antibodies induced by non-cytopathic viral infectionsCurrent Opinion in Microbiology, 2004, 7(4): 426-433.
Hessell et al., Fc receptor but not complement binding is important in antibody protection against HIV, Nature, 2007 449:101-104.
Beltramello et al., The human immune response to Dengue virus is dominated by highly cross-reactive antibodies endowed with neutralizing and enhancing activity, Cell Host Microbe, 2010, 8(3): 1-25.
de Alwis et al., In-Depth Analysis of the Antibody Response of Individuals Exposed to Primary Dengue Virus InfectionPLOS Neglected Tropical Dissease, 2011, 5(6)-1-8.
Simonelli et al., Rational engineering of a human anti-dengue antibody through experimentally validated computational docking, PLOS One 2013, 8(2):1-1 1.
Williams et al., Therapeutic efficacy of antibodies lacking Fcγ receptor binding against lethal dengue virus infection is due to neutralizing potency and blocking of enhancing antibodies, PLOS Pathog 2013, 9(2):1-17.
Ter Meulen et al., Human monoclonal antibody combination against SARS coronavirus: synergy and coverage of escape mutants, PLOS Medicine 2006, 3(7):e237.

\* cited by examiner

FIG. 1

Neutralization and antibody-dependent enhancement of wild-type mAbs

FIG. 2

Neutralization and antibody-dependent enhancement of LALA-variant mAbs

SEQUENCE LISTING

<160> NUMBER OF SEQ ID NOS: 198

<210> SEQ ID NO 1
<211> LENGTH: 8
<212> TYPE: PRT
<213> ORGANISM: Artificial Sequence
<220> FEATURE:
<223> OTHER INFORMATION: CDRH1 aa

<400> SEQUENCE: 1

Gly Phe Ser Phe Ser Ser Ser Ser
1               5

<210> SEQ ID NO 2
<211> LENGTH: 8
<212> TYPE: PRT
<213> ORGANISM: Artificial Sequence
<220> FEATURE:
<223> OTHER INFORMATION: CDRH2 aa

<400> SEQUENCE: 2

Ile Ser Thr Ser Gly Asn Tyr Ile
1               5

<210> SEQ ID NO 3
<211> LENGTH: 19
<212> TYPE: PRT
<213> ORGANISM: Artificial Sequence
<220> FEATURE:
<223> OTHER INFORMATION: CDRH3 aa

<400> SEQUENCE: 3

Ala Arg Asp Pro Cys Ser Ser Thr Thr Cys Tyr Phe Gly Tyr Tyr Ala
1               5                   10                  15

Met Asp Val

<210> SEQ ID NO 4
<211> LENGTH: 6
<212> TYPE: PRT
<213> ORGANISM: Artificial Sequence
<220> FEATURE:

```
<223> OTHER INFORMATION: CDRL1 aa

<400> SEQUENCE: 4

Asn Ile Gly Ser Lys Thr
1               5

<210> SEQ ID NO 5
<211> LENGTH: 3
<212> TYPE: PRT
<213> ORGANISM: Artificial Sequence
<220> FEATURE:
<223> OTHER INFORMATION: CDRL2 aa

<400> SEQUENCE: 5

Arg Asp Thr
1

<210> SEQ ID NO 6
<211> LENGTH: 9
<212> TYPE: PRT
<213> ORGANISM: Artificial Sequence
<220> FEATURE:
<223> OTHER INFORMATION: CDRL3 aa

<400> SEQUENCE: 6

Gln Val Trp Asp Gly Thr Ser Val Val
1               5

<210> SEQ ID NO 7
<211> LENGTH: 24
<212> TYPE: DNA
<213> ORGANISM: Artificial Sequence
<220> FEATURE:
<223> OTHER INFORMATION: CDRH1 nuc

<400> SEQUENCE: 7
ggattcagct ttagtagctc tagc                                          24

<210> SEQ ID NO 8
<211> LENGTH: 24
<212> TYPE: DNA
<213> ORGANISM: Artificial Sequence
<220> FEATURE:
<223> OTHER INFORMATION: CDRH2 nuc

<400> SEQUENCE: 8
atcagtacta gtggtaatta catc                                          24

<210> SEQ ID NO 9
<211> LENGTH: 56
<212> TYPE: DNA
<213> ORGANISM: Artificial Sequence
<220> FEATURE:
<223> OTHER INFORMATION: CDRH3 nuc

<400> SEQUENCE: 9
gcgagagatc cctgtagtag taccacgtgc tattttggtt attacgctat ggacgt       56

<210> SEQ ID NO 10
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 10
```

```
aatattggaa gtaaaact                                                    18

<210> SEQ ID NO 11
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 11 agggatacc                                                               9

<210> SEQ ID NO 12
<211> LENGTH: 27
<212> TYPE: DNA
<213> ORGANISM: Artificial Sequence
<220> FEATURE:
<223> OTHER INFORMATION: CDRL3 nuc

<400> SEQUENCE: 12
caggtgtggg acggcacttc tgtggtg                                          27

<210> SEQ ID NO 13
<211> LENGTH: 126
<212> TYPE: PRT
<213> ORGANISM: Artificial Sequence
<220> FEATURE:
<223> OTHER INFORMATION: heavy ch aa

<400> SEQUENCE: 13
```

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Ser Phe Ser Ser Ser
            20                  25                  30

Ser Met Asn Trp Val Arg Gln Ala Pro Gly Lys Gly Leu Gln Trp Val
        35                  40                  45

Ser Tyr Ile Ser Thr Ser Gly Asn Tyr Ile Tyr Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Val Glu Asp Thr Ala Val Tyr Tyr Cys
                85                  90                  95

Ala Arg Asp Pro Cys Ser Ser Thr Thr Cys Tyr Phe Gly Tyr Tyr Ala
            100                 105                 110

Met Asp Val Trp Gly Gln Gly Thr Thr Val Ala Val Ser Ser
        115                 120                 125

```
<210> SEQ ID NO 14
<211> LENGTH: 106
<212> TYPE: PRT
<213> ORGANISM: Artificial Sequence
<220> FEATURE:
<223> OTHER INFORMATION: light ch aa

<400> SEQUENCE: 14
```

Ser Tyr Glu Leu Thr Gln Pro Leu Ser Val Ser Val Ala Leu Gly Gln
1               5                   10                  15

Thr Ala Arg Val Thr Cys Gly Gly Asn Asn Ile Gly Ser Lys Thr Val
            20                  25                  30

His Trp Tyr Gln Gln Arg Pro Gly Gln Ala Pro Val Leu Val Ile Tyr
        35                  40                  45

```
Arg Asp Thr Asn Arg Pro Ser Gly Ile Pro Glu Arg Phe Ser Gly Ser
        50                  55                  60
Lys Ser Gly Ser Ala Ala Thr Leu Thr Ile Ser Arg Ala Gln Ala Gly
 65                  70                  75                  80
Asp Glu Ala Glu Tyr Tyr Cys Gln Val Trp Asp Gly Thr Ser Val Val
                     85                  90                  95
Phe Gly Gly Gly Thr Lys Leu Thr Val Leu
                100                 105
```

<210> SEQ ID NO 15
<211> LENGTH: 379
<212> TYPE: DNA
<213> ORGANISM: Artificial Sequence
<220> FEATURE:
<223> OTHER INFORMATION: heavy ch nuc

<400> SEQUENCE: 15

```
gaggtgcagc tggtgcagtc tggggggaggc ctggtcaagc cgggggggtc cctgagactc    60
tcctgtacag cctctggatt cagctttagt agctctagca tgaactgggt ccgccaggct   120
ccagggaagg gctgcagtg gtctcatac atcagtacta gtggtaatta catctactac    180
gcagactcag tgaagggccg attcaccatc tccagagaca cgccaagaa ctcagtgtat    240
ctgcaaatga acagcctgag agtcgaggac acggctgtgt attactgtgc gagagatccc   300
tgtagtagta ccacgtgcta ttttggttat acgctatgg acgtctgggg ccaagggacc   360
acggtcgccg tctcctcag                                                379
```

<210> SEQ ID NO 16
<211> LENGTH: 319
<212> TYPE: DNA
<213> ORGANISM: Artificial Sequence
<220> FEATURE:
<223> OTHER INFORMATION: light ch nuc

<400> SEQUENCE: 16

```
tcctatgagc tgactcagcc actctctgtg tcagtggccc tgggacagac ggccagggtt    60
acctgtgggg gaaacaatat tggaagtaaa actgtgcact ggtaccagca gaggccaggc   120
caggcccctg tgctggtcat ttatagggat accaaccggc cctctgggat ccctgagcga   180
ttctctggct ccaagtcggg gagcgcggcc accctgacca tcagcagagc ccaagccggg   240
gatgaggctg agtattactg ccaggtgtgg gacggcactt ctgtggtgtt cggcggaggg   300
accaagctga ccgtcctag                                                319
```

<210> SEQ ID NO 17
<211> LENGTH: 10
<212> TYPE: PRT
<213> ORGANISM: Artificial Sequence
<220> FEATURE:
<223> OTHER INFORMATION: CDRH1 aa

<400> SEQUENCE: 17

```
Gly Gly Ser Ile Ser Ser Ala Ser Tyr Tyr
 1               5                  10
```

<210> SEQ ID NO 18
<211> LENGTH: 7
<212> TYPE: PRT
<213> ORGANISM: Artificial Sequence
<220> FEATURE:
<223> OTHER INFORMATION: CDRH2 aa

```
<400> SEQUENCE: 18

Ile Tyr Thr Ser Gly Ser Thr
1               5

<210> SEQ ID NO 19
<211> LENGTH: 13
<212> TYPE: PRT
<213> ORGANISM: Artificial Sequence
<220> FEATURE:
<223> OTHER INFORMATION: CDRH3 aa

<400> SEQUENCE: 19

Ala Arg Glu Trp Ala Ala Arg Gly Gly Ile Val Asp Tyr
1               5                   10

<210> SEQ ID NO 20
<211> LENGTH: 6
<212> TYPE: PRT
<213> ORGANISM: Artificial Sequence
<220> FEATURE:
<223> OTHER INFORMATION: CDRL1 aa

<400> SEQUENCE: 20

Gln Ser Ile Ser Tyr Tyr
1               5

<210> SEQ ID NO 21
<211> LENGTH: 3
<212> TYPE: PRT
<213> ORGANISM: Artificial Sequence
<220> FEATURE:
<223> OTHER INFORMATION: CDRL2 aa

<400> SEQUENCE: 21

Gly Ala Ser
1

<210> SEQ ID NO 22
<211> LENGTH: 9
<212> TYPE: PRT
<213> ORGANISM: Artificial Sequence
<220> FEATURE:
<223> OTHER INFORMATION: CDRL3 aa

<400> SEQUENCE: 22

Gln Gln Ser Tyr Asp Phe Pro Arg Thr
1               5

<210> SEQ ID NO 23
<211> LENGTH: 30
<212> TYPE: DNA
<213> ORGANISM: Artificial Sequence
<220> FEATURE:
<223> OTHER INFORMATION: CDRH1 nuc

<400> SEQUENCE: 23
ggtggctcca tcagcagtgc tagttactac                                      30

<210> SEQ ID NO 24
<211> LENGTH: 21
<212> TYPE: DNA
<213> ORGANISM: Artificial Sequence
<220> FEATURE:
<223> OTHER INFORMATION: CDRH2 nuc

<400> SEQUENCE: 24
```

```
atctatacca gcgggagcac c                                              21
```

<210> SEQ ID NO 25
<211> LENGTH: 39
<212> TYPE: DNA
<213> ORGANISM: Artificial Sequence
<220> FEATURE:
<223> OTHER INFORMATION: CDRH3 nuc

<400> SEQUENCE: 25

```
gcgagagagt gggcagctcg gggggcatt gttgactac                            39
```

<210> SEQ ID NO 26
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 26

```
cagagcatta gttactat                                                  18
```

<210> SEQ ID NO 27
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 27

```
ggtgcatcc                                                             9
```

<210> SEQ ID NO 28
<211> LENGTH: 27
<212> TYPE: DNA
<213> ORGANISM: Artificial Sequence
<220> FEATURE:
<223> OTHER INFORMATION: CDRL3 nuc

<400> SEQUENCE: 28

```
caacaaagtt acgattttcc tcggacg                                        27
```

<210> SEQ ID NO 29
<211> LENGTH: 121
<212> TYPE: PRT
<213> ORGANISM: Artificial Sequence
<220> FEATURE:
<223> OTHER INFORMATION: heavy ch aa

<400> SEQUENCE: 29

```
Gln Val Gln Leu Gln Glu Ser Gly Pro Thr Leu Val Lys Pro Ser Gln
1               5                   10                  15

Thr Leu Ser Leu Thr Cys Ser Val Ser Gly Gly Ser Ile Ser Ser Ala
            20                  25                  30

Ser Tyr Tyr Trp Ser Trp Ile Arg Gln Pro Ala Gly Lys Gly Leu Glu
        35                  40                  45

Trp Ile Gly Gln Ile Tyr Thr Ser Gly Ser Thr Lys Tyr Asn Pro Ser
    50                  55                  60

Leu Lys Ser Arg Leu Thr Leu Ser Met Asp Thr Ser Lys Asn Gln Phe
65                  70                  75                  80

Thr Leu Lys Leu Ser Ser Val Thr Ala Ala Asp Thr Ala Leu Tyr Tyr
                85                  90                  95

Cys Ala Arg Glu Trp Ala Ala Arg Gly Gly Ile Val Asp Tyr Trp Gly
```

```
                     100                 105                 110
Gln Gly Thr Leu Val Thr Val Ser Ser
            115                 120

<210> SEQ ID NO 30
<211> LENGTH: 107
<212> TYPE: PRT
<213> ORGANISM: Artificial Sequence
<220> FEATURE:
<223> OTHER INFORMATION: light ch aa

<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Tyr Tyr
            20                  25                  30

Leu Asn Trp Tyr Gln Gln Lys Pro Gly Lys Ala Pro Lys Val Leu Ile
        35                  40                  45

Tyr Gly Ala Ser Ser Leu Gln Ser Gly Val Pro Ser Arg Phe Ser Gly
    50                  55                  60

Ser Gly Ser Glu Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Phe Pro Arg
                85                  90                  95

Thr Phe Gly Gln Gly Thr Lys Val Glu Ile Lys
            100                 105

<210> SEQ ID NO 31
<211> LENGTH: 364
<212> TYPE: DNA
<213> ORGANISM: Artificial Sequence
<220> FEATURE:
<223> OTHER INFORMATION: heavy ch nuc

<400> SEQUENCE: 31
caggtgcagc tgcaggagtc gggggccaaca ctggtgaagc cttcacagac cctgtccctc     60
acctgcagtg tctctggtgg ctccatcagc agtgctagtt actactggag ctggatccgg    120
cagcccgccg ggaagggact ggagtggatt ggcaaatct ataccagcgg gagcaccaag     180
tacaacccct ccctcaagag tcgactcacc ctgtcaatgg acacgtccaa gaaccagttc    240
accctgaagc tgagctctgt gaccgccgca gatacggcct tatattattg cgcgagagag    300
tgggcagctc ggggggggcat gttgactac tggggccagg gaaccctggt caccgtctcc    360
tcag                                                                 364

<210> SEQ ID NO 32
<211> LENGTH: 322
<212> TYPE: DNA
<213> ORGANISM: Artificial Sequence
<220> FEATURE:
<223> OTHER INFORMATION: light ch nuc

<400> SEQUENCE: 32
gacatccaga tgacccagtc tccatcctcc ctgtctgcat ctgtaggaga cagagtcacc     60
atcacttgcc gagcaagtca gagcattagt tactatttaa attggtatca gcagaaaccc    120
gggaaagccc ctaaggtcct gatctatggt gcatccagtt tgcaaagcgg ggtcccatca    180
aggttcagtg gcagtggatc tgagacagat ttcactctca ccatcagcag tctgcaacct    240
gaagattttg caacttacta ctgtcaacaa agttacgatt ttcctcggac gttcggccaa    300
```
gggaccaagg tggaaatcaa gc                                              322

<210> SEQ ID NO 33
<211> LENGTH: 10
<212> TYPE: PRT
<213> ORGANISM: Artificial Sequence
<220> FEATURE:
<223> OTHER INFORMATION: CDRH1 aa

<400> SEQUENCE: 33

Gly Gly Ser Ile Ser Ser Ser Gly Tyr Ser
1               5                   10

<210> SEQ ID NO 34
<211> LENGTH: 7
<212> TYPE: PRT
<213> ORGANISM: Artificial Sequence
<220> FEATURE:
<223> OTHER INFORMATION: CDRH2 aa

<400> SEQUENCE: 34

Ile Ser Ala Ser Gly Thr Thr
1               5

<210> SEQ ID NO 35
<211> LENGTH: 19
<212> TYPE: PRT
<213> ORGANISM: Artificial Sequence
<220> FEATURE:
<223> OTHER INFORMATION: CDRH3 aa

<400> SEQUENCE: 35

Ala Arg Asp Thr Glu Cys Ser Asp Thr Ser Cys Phe Pro Ser Ile Trp
1               5                   10                  15

Phe Asp Thr

<210> SEQ ID NO 36
<211> LENGTH: 6
<212> TYPE: PRT
<213> ORGANISM: Artificial Sequence
<220> FEATURE:
<223> OTHER INFORMATION: CDRL1 aa

<400> SEQUENCE: 36

Asn Ile Gly Thr Lys Gly
1               5

<210> SEQ ID NO 37
<211> LENGTH: 3
<212> TYPE: PRT
<213> ORGANISM: Artificial Sequence
<220> FEATURE:
<223> OTHER INFORMATION: CDRL2 aa

<400> SEQUENCE: 37

Tyr Asp Ser
1

<210> SEQ ID NO 38
<211> LENGTH: 14
<212> TYPE: PRT
<213> ORGANISM: Artificial Sequence
<220> FEATURE:
<223> OTHER INFORMATION: CDRL3 aa

<400> SEQUENCE: 38

Gln Val Trp Asp Asn Thr Asp Asp Ser Ser Asp His Pro Val
1               5                   10

<210> SEQ ID NO 39
<211> LENGTH: 30
<212> TYPE: DNA
<213> ORGANISM: Artificial Sequence
<220> FEATURE:
<223> OTHER INFORMATION: CDRH1 nuc

<400> SEQUENCE: 39
ggtggctcca tcagcagtag tggttactcc                                    30

<210> SEQ ID NO 40
<211> LENGTH: 21
<212> TYPE: DNA
<213> ORGANISM: Artificial Sequence
<220> FEATURE:
<223> OTHER INFORMATION: CDRH2 nuc

<400> SEQUENCE: 40
atttctgcca gtgggaccac c                                             21

<210> SEQ ID NO 41
<211> LENGTH: 57
<212> TYPE: DNA
<213> ORGANISM: Artificial Sequence
<220> FEATURE:
<223> OTHER INFORMATION: CDRH3 nuc

<400> SEQUENCE: 41
gcgagggata cggagtgtag tgatacgagt tgctttccct ccatctggtt cgatacc      57

<210> SEQ ID NO 42
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 42
aacattggaa ctaaaggt                                                 18

<210> SEQ ID NO 43
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 43 tatgatagc                                                           9

<210> SEQ ID NO 44
<211> LENGTH: 42
<212> TYPE: DNA
<213> ORGANISM: Artificial Sequence
<220> FEATURE:
<223> OTHER INFORMATION: CDRL3 nuc

<400> SEQUENCE: 44
caggtgtggg ataatactga tgacagtagt gatcacccgg tg                      42

<210> SEQ ID NO 45
<211> LENGTH: 127

```
<212> TYPE: PRT
<213> ORGANISM: Artificial Sequence
<220> FEATURE:
<223> OTHER INFORMATION: heavy ch aa

<400> SEQUENCE: 45

Gln Val Gln Leu Gln Glu Ser Gly Pro Gly Leu Val Lys Ser Ser Gln
1               5                   10                  15

Thr Leu Ser Leu Thr Cys Thr Val Ser Gly Gly Ser Ile Ser Ser Ser
            20                  25                  30

Gly Tyr Ser Trp Asn Trp Ile Arg Gln Pro Ala Gly Lys Gly Leu Glu
        35                  40                  45

Trp Ile Gly Arg Ile Ser Ala Ser Gly Thr Thr Asn Tyr Asn Pro Ser
50                  55                  60

Val Lys Ser Arg Gly Thr Val Ser Val Asp Thr Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Asp Thr Glu Cys Ser Asp Thr Ser Cys Phe Pro Ser Ile
            100                 105                 110

Trp Phe Asp Thr Trp Gly Gln Gly Ala Leu Val Thr Val Ser Ser
        115                 120                 125

<210> SEQ ID NO 46
<211> LENGTH: 111
<212> TYPE: PRT
<213> ORGANISM: Artificial Sequence
<220> FEATURE:
<223> OTHER INFORMATION: light ch aa

<400> SEQUENCE: 46

Ser Tyr Glu Leu Thr Gln Pro Pro Ser Val Ser Val Ala Pro Gly Lys
1               5                   10                  15

Thr Ala Thr Ile Thr Cys Gly Gly Asn Asn Ile Gly Thr Lys Gly Val
            20                  25                  30

His Trp Tyr Gln Arg Lys Ala Gly Gln Ala Pro Val Leu Val Ile Tyr
        35                  40                  45

Tyr Asp Ser Val Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asn Thr Asp Asp Ser
                85                  90                  95

Ser Asp His Pro Val Phe Gly Gly Gly Ser Lys Leu Thr Val Leu
            100                 105                 110

<210> SEQ ID NO 47
<211> LENGTH: 382
<212> TYPE: DNA
<213> ORGANISM: Artificial Sequence
<220> FEATURE:
<223> OTHER INFORMATION: heavy ch nuc

<400> SEQUENCE: 47
caggtgcagc tgcaggagtc gggcccagga ctggtgaaga gttcacagac cctgtccctc      60
acctgcactg tctctggtgg ctccatcagc agtagtggtt actcctggaa ctggatccgg     120
cagcccgccg ggaagggact ggagtggatt ggccgtattt ctgccagtgg gaccaccaac     180
tacaacccct ccgtcaagag tcgaggcact gtttcagtag acacgtccaa gaaccagttc     240
```

```
tccctgaggc tgacctctgt taccgccgcg gacacggccg tttactattg tgcgagggat    300
acggagtgta gtgatacgag ttgctttccc tccatctggt tcgatacctg gggccaggga    360
gccctggtca ccgtctcctc ag                                             382
```

```
<210> SEQ ID NO 48
<211> LENGTH: 334
<212> TYPE: DNA
<213> ORGANISM: Artificial Sequence
<220> FEATURE:
<223> OTHER INFORMATION: light ch nuc

<400> SEQUENCE: 48
```

```
tcctatgtgc tgactcagcc accctcagtg tcagtggccc caggaaagac ggccaccatt     60
acctgtgggg gaaacaacat tggaactaaa ggtgtgcact ggtaccagcg gaaggcaggc    120
caggcccctg tgttggtcat ctattatgat agcgtccggc cctcagggat ccctgagcgc    180
ttctctggct ccaactctgg gaacacggcc accctgacca tcagcagggt cgaagccggg    240
gatgaggccg actattactg tcaggtgtgg gataatactg atgacagtag tgatcacccg    300
gtgttcggcg agggtccaa gctgaccgtc ctag                                  334
```

```
<210> SEQ ID NO 49
<211> LENGTH: 10
<212> TYPE: PRT
<213> ORGANISM: Artificial Sequence
<220> FEATURE:
<223> OTHER INFORMATION: CDRH1 aa

<400> SEQUENCE: 49

Ser Gly Ser Ile Ser Thr Ser Asp Tyr Tyr
1               5                   10
```

```
<210> SEQ ID NO 50
<211> LENGTH: 7
<212> TYPE: PRT
<213> ORGANISM: Artificial Sequence
<220> FEATURE:
<223> OTHER INFORMATION: CDRH2 aa

<400> SEQUENCE: 50

Val Tyr Tyr Ser Glu Ser Thr
1               5
```

```
<210> SEQ ID NO 51
<211> LENGTH: 10
<212> TYPE: PRT
<213> ORGANISM: Artificial Sequence
<220> FEATURE:
<223> OTHER INFORMATION: CDRH3 aa

<400> SEQUENCE: 51

Ala Arg Gln Arg Gly Asn Trp Phe Asp Ser
1               5                   10
```

```
<210> SEQ ID NO 52
<211> LENGTH: 6
<212> TYPE: PRT
<213> ORGANISM: Artificial Sequence
<220> FEATURE:
<223> OTHER INFORMATION: CDRH3 aa

<400> SEQUENCE: 52

Gln Gly Ile Ser Asn Tyr
1               5
```

<210> SEQ ID NO 53
<211> LENGTH: 3
<212> TYPE: PRT
<213> ORGANISM: Artificial Sequence
<220> FEATURE:
<223> OTHER INFORMATION: CDRL2 aa

<400> SEQUENCE: 53

Ala Ala Ser
1

<210> SEQ ID NO 54
<211> LENGTH: 9
<212> TYPE: PRT
<213> ORGANISM: Artificial Sequence
<220> FEATURE:
<223> OTHER INFORMATION: CDRL3 aa

<400> SEQUENCE: 54

Gln Gln Leu Asn Asn Tyr Glu Phe Thr
1               5

<210> SEQ ID NO 55
<211> LENGTH: 30
<212> TYPE: DNA
<213> ORGANISM: Artificial Sequence
<220> FEATURE:
<223> OTHER INFORMATION: CDRH1 nuc

<400> SEQUENCE: 55
agtggctcca tcagcactag tgattactac                                    30

<210> SEQ ID NO 56
<211> LENGTH: 21
<212> TYPE: DNA
<213> ORGANISM: Artificial Sequence
<220> FEATURE:
<223> OTHER INFORMATION: CDRH2 nuc

<400> SEQUENCE: 56
gtctattata gtgagagcac c                                             21

<210> SEQ ID NO 57
<211> LENGTH: 30
<212> TYPE: DNA
<213> ORGANISM: Artificial Sequence
<220> FEATURE:
<223> OTHER INFORMATION: CDRH3 nuc

<400> SEQUENCE: 57
gccagacaac gaggaaactg gttcgactcc                                    30

<210> SEQ ID NO 58
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 58
cagggcatta gcaattat                                                 18

<210> SEQ ID NO 59
<211> LENGTH: 9

```
<212> TYPE: DNA
<213> ORGANISM: Artificial Sequence
<220> FEATURE:
<223> OTHER INFORMATION: CDRL2 nuc

<400> SEQUENCE: 59 gctgcatcc                                                                 9

<210> SEQ ID NO 60
<211> LENGTH: 27
<212> TYPE: DNA
<213> ORGANISM: Artificial Sequence
<220> FEATURE:
<223> OTHER INFORMATION: CDRL3 nuc

<400> SEQUENCE: 60
caacaactta ataattacga attcact                                            27

<210> SEQ ID NO 61
<211> LENGTH: 118
<212> TYPE: PRT
<213> ORGANISM: Artificial Sequence
<220> FEATURE:
<223> OTHER INFORMATION: heavy ch aa

<400> SEQUENCE: 61
```

Gln Leu Gln Met His Glu Ser Gly Pro Gly Leu Val Lys Pro Ser Glu
1               5                   10                  15

Thr Leu Ser Leu Thr Cys Ile Val Ser Gly Ser Ile Ser Thr Ser
            20                  25                  30

Asp Tyr Tyr Trp Gly Trp Ile Arg Gln Pro Pro Gly Lys Gly Leu Glu
        35                  40                  45

Trp Ile Gly Ser Val Tyr Tyr Ser Glu Ser Thr Tyr Tyr Ser Pro Ser
    50                  55                  60

Leu Lys Ser Arg Ile Thr Ile Ser Val Asp Thr Ser Arg Asn Gln Phe
65                  70                  75                  80

Ser Leu Asn Val Ser Ser Val Thr Ala Ala Asp Thr Ala Ile Tyr Phe
                85                  90                  95

Cys Ala Arg Gln Arg Gly Asn Trp Phe Asp Ser Trp Gly Gln Gly Thr
            100                 105                 110

Leu Val Thr Val Ser Ser
        115

```
<210> SEQ ID NO 62
<211> LENGTH: 107
<212> TYPE: PRT
<213> ORGANISM: Artificial Sequence
<220> FEATURE:
<223> OTHER INFORMATION: light ch aa

<400> SEQUENCE: 62
```

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Asn Tyr Glu Phe
                85                  90                  95

Thr Phe Gly Pro Gly Thr Lys Val Asp Ile Lys
            100                 105

<210> SEQ ID NO 63
<211> LENGTH: 355
<212> TYPE: DNA
<213> ORGANISM: Artificial Sequence
<220> FEATURE:
<223> OTHER INFORMATION: heavy ch nuc

<400> SEQUENCE: 63
cagctgcaga tgcacgagtc gggcccagga ctggtgaagc cttcggagac cctgtccctc    60
acgtgcattg tctctagtgg ctccatcagc actagtgatt actactgggg ctggatccgc   120
cagcccccag ggaaggggct ggagtggatt gggagtgtct attatagtga agcacctac    180 tacagtccgt ccctcaagag tcgaatcacc atatccgtag acacgtccag gaaccagttc   240
tccctgaacg tgagttctgt gaccgccgca gacacggcta tatatttctg tgccagacaa   300
cgaggaaact ggttcgactc ctggggccag ggaaccctgg tcaccgtctc ctcag        355

<210> SEQ ID NO 64
<211> LENGTH: 322
<212> TYPE: DNA
<213> ORGANISM: Artificial Sequence
<220> FEATURE:
<223> OTHER INFORMATION: light ch nuc

<400> SEQUENCE: 64
gccatccagt tgacccagtc tccatcctcc ctatctgcat ctgtaggaga cagagtcacc    60
atcacttgcc gggccagtca gggcattagc aattatttag cctggtatca gcaaaaacca   120
gggaaagccc ctaagctcct gatctatgct gcatccactt tgcaaagtgg ggtcccatca   180
aggttcagcg gcagtggctc tgggacagat ttcactctca ccatcagcag cctgcagcct   240
gaagattttg caacttatta ctgtcaacaa cttaataatt acgaattcac tttcggccct   300
gggaccaaag tggatatcaa ac                                            322

<210> SEQ ID NO 65
<211> LENGTH: 118
<212> TYPE: PRT
<213> ORGANISM: Artificial Sequence
<220> FEATURE:
<223> OTHER INFORMATION: heavy ch var1 aa

<400> SEQUENCE: 65

Gln Leu Gln Met His Glu Ser Gly Pro Gly Leu Val Lys Pro Ser Glu
1               5                   10                  15

Thr Leu Ser Leu Thr Cys Thr Val Ser Gly Ser Ile Ser Thr Ser
                20                  25                  30

Asp Tyr Tyr Trp Gly Trp Ile Arg Gln Pro Pro Gly Lys Gly Leu Glu
                35                  40                  45

Trp Ile Gly Ser Val Tyr Tyr Ser Glu Ser Thr Tyr Tyr Ser Pro Ser
            50                  55                  60

Leu Lys Ser Arg Ile Thr Ile Ser Val Asp Thr Ser Arg Asn Gln Phe
65                  70                  75                  80

Ser Leu Asn Val Ser Ser Val Thr Ala Ala Asp Thr Ala Ile Tyr Phe
                85                  90                  95

Cys Ala Arg Gln Arg Gly Asn Trp Phe Asp Ser Trp Gly Gln Gly Thr
                100                 105                 110

Leu Val Thr Val Ser Ser
        115

<210> SEQ ID NO 66
<211> LENGTH: 355
<212> TYPE: DNA
<213> ORGANISM: Artificial Sequence
<220> FEATURE:
<223> OTHER INFORMATION: heavy ch var1 nuc

<400> SEQUENCE: 66
cagctgcaga tgcacgagtc gggcccagga ctggtgaagc cttcggagac cctgtccctc      60
acgtgcactg tctctagtgg ctccatcagc actagtgatt actactgggg ctggatccgc     120
cagcccccag ggaagggggct ggagtggatt gggagtgtct attatagtga agcacctac     180 tacagtccgt ccctcaagag tcgaatcacc atatccgtag acacgtccag gaaccagttc     240
tccctgaacg tgagttctgt gaccgccgca gacacggcta tatatttctg tgccagacaa     300
cgaggaaact ggttcgactc ctggggccag ggaaccctgg tcaccgtctc ctcag          355

<210> SEQ ID NO 67
<211> LENGTH: 8
<212> TYPE: PRT
<213> ORGANISM: Artificial Sequence
<220> FEATURE:
<223> OTHER INFORMATION: CDRH1 aa

<400> SEQUENCE: 67

Ala Phe Asn Phe Ser Thr Asn Ala
1               5

<210> SEQ ID NO 68
<211> LENGTH: 8
<212> TYPE: PRT
<213> ORGANISM: Artificial Sequence
<220> FEATURE:
<223> OTHER INFORMATION: CDRH2 aa

<400> SEQUENCE: 68

Ile Ser Tyr Asp Gly Ser His Lys
1               5

<210> SEQ ID NO 69
<211> LENGTH: 17
<212> TYPE: PRT
<213> ORGANISM: Artificial Sequence
<220> FEATURE:
<223> OTHER INFORMATION: CDRH3 aa

<400> SEQUENCE: 69

Ala Thr Val Gly Val Leu Thr Trp Pro Val Asn Ala Glu Tyr Phe His
1               5                   10                  15

His

<210> SEQ ID NO 70
<211> LENGTH: 9
<212> TYPE: PRT
<213> ORGANISM: Artificial Sequence
<220> FEATURE:
<223> OTHER INFORMATION: CDRL1 aa

<400> SEQUENCE: 70

Ser Ser Asn Ile Gly Ala Gly Tyr Asp
1               5

<210> SEQ ID NO 71
<211> LENGTH: 3
<212> TYPE: PRT
<213> ORGANISM: Artificial Sequence
<220> FEATURE:
<223> OTHER INFORMATION: CDRL2 aa

<400> SEQUENCE: 71

Gly Asn Asn
1

<210> SEQ ID NO 72
<211> LENGTH: 11
<212> TYPE: PRT
<213> ORGANISM: Artificial Sequence
<220> FEATURE:
<223> OTHER INFORMATION: CDRL3 aa

<400> SEQUENCE: 72

Gln Ser Tyr Asp Ser Ser Leu Thr Gly Val Val
1               5                   10

<210> SEQ ID NO 73
<211> LENGTH: 24
<212> TYPE: DNA
<213> ORGANISM: Artificial Sequence
<220> FEATURE:
<223> OTHER INFORMATION: CDRH1 nuc

<400> SEQUENCE: 73
gcattcaact tcagtaccaa tgcc                                          24

<210> SEQ ID NO 74
<211> LENGTH: 24
<212> TYPE: DNA
<213> ORGANISM: Artificial Sequence
<220> FEATURE:
<223> OTHER INFORMATION: CDRH2 nuc

<400> SEQUENCE: 74
atatcatatg atggaagcca taaa                                          24

<210> SEQ ID NO 75
<211> LENGTH: 51
<212> TYPE: DNA
<213> ORGANISM: Artificial Sequence
<220> FEATURE:
<223> OTHER INFORMATION: CDRH3 nuc

<400> SEQUENCE: 75
gcgacagtgg gagtccttac atggcccgtc aacgctgagt actttcacca c            51

<210> SEQ ID NO 76
<211> LENGTH: 27
<212> TYPE: DNA
<213> ORGANISM: Artificial Sequence
<220> FEATURE:
<223> OTHER INFORMATION: CDRL1 nuc

<400> SEQUENCE: 76
agctccaaca tcggggcagg ttatgat                                       27

<210> SEQ ID NO 77

-continued

```
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 77 ggtaacaac                                                                  9

<210> SEQ ID NO 78
<211> LENGTH: 33
<212> TYPE: DNA
<213> ORGANISM: Artificial Sequence
<220> FEATURE:
<223> OTHER INFORMATION: CDRL3 nuc

<400> SEQUENCE: 78
cagtcctatg acagcagcct gactggtgtg gta                                      33

<210> SEQ ID NO 79
<211> LENGTH: 124
<212> TYPE: PRT
<213> ORGANISM: Artificial Sequence
<220> FEATURE:
<223> OTHER INFORMATION: heavy ch aa

<400> SEQUENCE: 79

Gln Ala His Leu Val Glu Ser Gly Gly Gly Val Val Gln Pro Gly Arg
1               5                   10                  15

Ser Leu Arg Leu Ser Cys Ala Ala Ser Ala Phe Asn Phe Ser Thr Asn
            20                  25                  30

Ala Met His Trp Val Arg Gln Ala Pro Gly Lys Gly Leu Glu Trp Val
        35                  40                  45

Ala Val Ile Ser Tyr Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Val Tyr Tyr Cys
                85                  90                  95

Ala Thr Val Gly Val Leu Thr Trp Pro Val Asn Ala Glu Tyr Phe His
            100                 105                 110

His Trp Gly Gln Gly Ser Leu Val Ser Val Ser Ser
        115                 120

<210> SEQ ID NO 80
<211> LENGTH: 111
<212> TYPE: PRT
<213> ORGANISM: Artificial Sequence
<220> FEATURE:
<223> OTHER INFORMATION: light ch aa

<400> SEQUENCE: 80

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Cys Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
```

```
                65                  70                  75                  80
Gln Ala Glu Asp Glu Ala Asp Tyr Tyr Cys Gln Ser Tyr Asp Ser Ser
                    85                  90                  95

Leu Thr Gly Val Val Phe Gly Gly Gly Thr Lys Leu Thr Val Leu
                100                 105                 110
```

<210> SEQ ID NO 81
<211> LENGTH: 373
<212> TYPE: DNA
<213> ORGANISM: Artificial Sequence
<220> FEATURE:
<223> OTHER INFORMATION: heavy ch nuc

<400> SEQUENCE: 81

```
caggcgcacc tggtggaatc tgggggaggc gtggtccagc ctggggaggtc cctgagactc      60
tcctgtgcag cctctgcatt caacttcagt accaatgcca tgcactgggt ccgccaggct     120
ccaggcaagg ggctggaatg ggtggcagta atatcatatg atggaagcca taaatactac     180
gcagactccg tgaagggccg attcaccatc tccagagaca attccaagaa cacgctgtat     240
ctgcaaatga acagcctgag agcggcggac acggctgtct attactgtgc gacagtggga     300
gtccttacat ggcccgtcaa cgctgagtac tttcaccact ggggccaggg ctccctggtc     360
agcgtctctt cag                                                         373
```

<210> SEQ ID NO 82
<211> LENGTH: 334
<212> TYPE: DNA
<213> ORGANISM: Artificial Sequence
<220> FEATURE:
<223> OTHER INFORMATION: light ch nuc

<400> SEQUENCE: 82

```
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttcctggaa cagcccccaa actcctcatc tgtggtaaca caatcggcc tcaggagtc       180
cctgaccgat tctctggctc caagtctggc acctcagcct ccctggccat cactgggctc     240
caggctgagg atgaggctga ttattattgc cagtcctatg acagcagcct gactggtgtg     300
gtattcggcg agggaccaa gctgaccgtc ctag                                   334
```

<210> SEQ ID NO 83
<211> LENGTH: 8
<212> TYPE: PRT
<213> ORGANISM: Artificial Sequence
<220> FEATURE:
<223> OTHER INFORMATION: CDRH1 aa

<400> SEQUENCE: 83

```
Gly Phe Thr Phe Asp Asp Tyr Ala
1               5
```

<210> SEQ ID NO 84
<211> LENGTH: 8
<212> TYPE: PRT
<213> ORGANISM: Artificial Sequence
<220> FEATURE:
<223> OTHER INFORMATION: CDRH2 aa

<400> SEQUENCE: 84

```
Ile Ser Trp Asn Ser Ala Thr Ile
1               5
```

<210> SEQ ID NO 85
<211> LENGTH: 17
<212> TYPE: PRT
<213> ORGANISM: Artificial Sequence
<220> FEATURE:
<223> OTHER INFORMATION: CDRH3 aa

<400> SEQUENCE: 85

Ala Lys Gly Gly Pro Arg Gly Leu Gln Leu Leu Ser Ser Trp Val Asp
1               5                   10                  15
Tyr

<210> SEQ ID NO 86
<211> LENGTH: 6
<212> TYPE: PRT
<213> ORGANISM: Artificial Sequence
<220> FEATURE:
<223> OTHER INFORMATION: CDRL1 aa

<400> SEQUENCE: 86

Gln Asp Ile Arg Arg Tyr
1               5

<210> SEQ ID NO 87
<211> LENGTH: 3
<212> TYPE: PRT
<213> ORGANISM: Artificial Sequence
<220> FEATURE:
<223> OTHER INFORMATION: CDRL2 aa

<400> SEQUENCE: 87

Thr Thr Ser
1

<210> SEQ ID NO 88
<211> LENGTH: 9
<212> TYPE: PRT
<213> ORGANISM: Artificial Sequence
<220> FEATURE:
<223> OTHER INFORMATION: CDRL3 aa

<400> SEQUENCE: 88

Gln Gln Ser Tyr Ser Pro Pro His Thr
1               5

<210> SEQ ID NO 89
<211> LENGTH: 24
<212> TYPE: DNA
<213> ORGANISM: Artificial Sequence
<220> FEATURE:
<223> OTHER INFORMATION: CDRH1 nuc

<400> SEQUENCE: 89
ggattcacgt ttgatgatta tgcc                                          24

<210> SEQ ID NO 90
<211> LENGTH: 24
<212> TYPE: DNA
<213> ORGANISM: Artificial Sequence
<220> FEATURE:
<223> OTHER INFORMATION: CDRH2 nuc

<400> SEQUENCE: 90
attagttgga atagtgccac cata                                          24

<210> SEQ ID NO 91
<211> LENGTH: 51
<212> TYPE: DNA
<213> ORGANISM: Artificial Sequence
<220> FEATURE:
<223> OTHER INFORMATION: CDRH3 nuc

<400> SEQUENCE: 91
gcgaaagggg gccctagggg gctgcaactg ctatcatcgt gggtcgacta c    51

<210> SEQ ID NO 92
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 92
caggacattc gcaggtat    18

<210> SEQ ID NO 93
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 93 actacatcc    9

<210> SEQ ID NO 94
<211> LENGTH: 27
<212> TYPE: DNA
<213> ORGANISM: Artificial Sequence
<220> FEATURE:
<223> OTHER INFORMATION: CDRL3 nuc

<400> SEQUENCE: 94
caacagagtt acagtccccc tcacact    27

<210> SEQ ID NO 95
<211> LENGTH: 124
<212> TYPE: PRT
<213> ORGANISM: Artificial Sequence
<220> FEATURE:
<223> OTHER INFORMATION: heavy ch aa

<400> SEQUENCE: 95

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Phe Trp Val Arg Gln Ala Pro Gly Lys Gly Leu Glu Trp Ile
        35                  40                  45

Ser Gly Ile Ser Trp Asn Ser Ala Thr Ile Gly Tyr Ala Asp Ser Val
    50                  55                  60

Lys Gly Arg Phe Thr Ile Ser Arg Asp Asn Ala Lys Lys Ser Leu Asp
65                  70                  75                  80

Leu Gln Met Asn Ser Leu Arg Pro Asp Asp Thr Ala Leu Tyr Tyr Cys
                85                  90                  95

Ala Lys Gly Gly Pro Arg Gly Leu Gln Leu Leu Ser Ser Trp Val Asp
            100                 105                 110

Tyr Trp Gly Gln Gly Thr Leu Val Thr Val Ser Ser
            115                 120

<210> SEQ ID NO 96
<211> LENGTH: 107
<212> TYPE: PRT
<213> ORGANISM: Artificial Sequence
<220> FEATURE:
<223> OTHER INFORMATION: light ch aa

<400> SEQUENCE: 96

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Arg Arg Tyr
            20                  25                  30
Leu Asn Trp Tyr Gln Gln Arg Pro Gly Arg Val Pro Gln Leu Leu Ile
        35                  40                  45
Tyr Thr Thr Ser Thr Leu Gln Ser Gly Val Pro Ser Arg Phe Ser Gly
    50                  55                  60
Ser Gly Ser Val Thr Asp Phe Thr Leu Thr Ile Ser Ser Leu Gln Pro
65                  70                  75                  80
Glu Asp Phe Gly Thr Tyr Tyr Cys Gln Gln Ser Tyr Ser Pro Pro His
                85                  90                  95
Thr Phe Gly Gln Gly Thr Lys Leu Glu Ile Lys
            100                 105

<210> SEQ ID NO 97
<211> LENGTH: 373
<212> TYPE: DNA
<213> ORGANISM: Artificial Sequence
<220> FEATURE:
<223> OTHER INFORMATION: heavy ch nuc

<400> SEQUENCE: 97
gaagtgcagc tggtggagtc tgggggaggc ttggtacagc ctggcaggtc cctgagactc      60
tcctgtgcag cctctggatt cacgtttgat gattatgcca tgttctgggt ccggcaagct     120
ccagggaagg gcctggaatg gatctcaggt attagttgga atagtgccac cataggctat     180
gcggactctg tgaagggccg attcaccatc tccagagaca acgccaagaa gtccctggat     240
ctgcagatga atagtctgag acctgatgac acggccttat attattgtgc gaaggggggc     300
cctagggggc tgcaactgct atcatcgtgg gtcgactact ggggccaggg aaccctggtc     360
accgtctcct cgg                                                       373

<210> SEQ ID NO 98
<211> LENGTH: 322
<212> TYPE: DNA
<213> ORGANISM: Artificial Sequence
<220> FEATURE:
<223> OTHER INFORMATION: light ch nuc

<400> SEQUENCE: 98
gacatccaga tgacccagtc tccgtcctcc ctgtctgcgt ctgttgggga cagagtcacc      60
atcacttgcc gggcaagtca ggacattcgc aggtatttga attggtatca gcagagacca     120
gggagagtcc ctcagctcct gatctatact acatccactc tccaaagtgg ggtcccatcc     180
aggttcagtg gcagtggatc tgtgacagat ttcactctca ccatcagcag tctgcaacct     240
gaagattttg gaacttacta ctgtcaacag agttacagtc cccctcacac ttttggccag     300
gggaccaagc tggagatcaa gc                                             322

<210> SEQ ID NO 99
<211> LENGTH: 6
<212> TYPE: PRT
<213> ORGANISM: Artificial Sequence
<220> FEATURE:
<223> OTHER INFORMATION: CDRL1 aa var1

<400> SEQUENCE: 99

```
Gln Gly Ile Ser Asn Trp
1               5
```

<210> SEQ ID NO 100
<211> LENGTH: 9
<212> TYPE: PRT
<213> ORGANISM: Artificial Sequence
<220> FEATURE:
<223> OTHER INFORMATION: CDRL3 aa var1

<400> SEQUENCE: 100

```
Gln Gln Ala Asn Ser Phe Pro Pro Thr
1               5
```

<210> SEQ ID NO 101
<211> LENGTH: 18
<212> TYPE: DNA
<213> ORGANISM: Artificial Sequence
<220> FEATURE:
<223> OTHER INFORMATION: CDRL1 nuc var1

<400> SEQUENCE: 101

```
cagggtatta gcaactgg                                                 18
```

<210> SEQ ID NO 102
<211> LENGTH: 27
<212> TYPE: DNA
<213> ORGANISM: Artificial Sequence
<220> FEATURE:
<223> OTHER INFORMATION: CDRL3 nuc var1

<400> SEQUENCE: 102

```
cagcaggcta acagtttccc tccgacg                                       27
```

<210> SEQ ID NO 103
<211> LENGTH: 107
<212> TYPE: PRT
<213> ORGANISM: Artificial Sequence
<220> FEATURE:
<223> OTHER INFORMATION: light ch aa var1

<400> SEQUENCE: 103

```
Asp Ile Leu Met Thr Gln Ser Pro Ser Phe Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Asn Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Pro
                85                  90                  95
```

Thr Phe Gly Gln Gly Thr Lys Val Glu Ser Lys
            100                 105

<210> SEQ ID NO 104
<211> LENGTH: 322
<212> TYPE: DNA
<213> ORGANISM: Artificial Sequence
<220> FEATURE:
<223> OTHER INFORMATION: light ch nuc var1

<400> SEQUENCE: 104
gacatcctca tgacccagtc tccatctttc gtgtctgcat ctgtaggaga cagagtcacc      60
atcacttgtc gggcgagtca gggtattagc aactggttag cctggtatca gcagaaacca     120
gggaaagccc ctaacctcct gatctctgct gcatccagtt tgcaaagtgg ggtcccatca     180
aggttcagcg gcagtggatc tgggacagat ttcactctca ccatcagcag cctgcagcct     240
gaagattttg caacttactt ttgtcagcag gctaacagtt tccctccgac gttcggccaa     300
gggaccaagg tggaaagcaa ac                                              322

<210> SEQ ID NO 105
<211> LENGTH: 8
<212> TYPE: PRT
<213> ORGANISM: Artificial Sequence
<220> FEATURE:
<223> OTHER INFORMATION: CDRH1 aa

<400> SEQUENCE: 105

Gly Phe Thr Phe Ser Arg Tyr Asp
1               5

<210> SEQ ID NO 106
<211> LENGTH: 7
<212> TYPE: PRT
<213> ORGANISM: Artificial Sequence
<220> FEATURE:
<223> OTHER INFORMATION: CDRH2 aa

<400> SEQUENCE: 106

Ile Thr Thr Ala Gly Asp Thr
1               5

<210> SEQ ID NO 107
<211> LENGTH: 22
<212> TYPE: PRT
<213> ORGANISM: Artificial Sequence
<220> FEATURE:
<223> OTHER INFORMATION: CDRH3 aa

<400> SEQUENCE: 107

Ala Arg Gly Pro Pro Thr Asp Cys Ser Ser Gly Arg Cys Leu Gly Val
1               5                   10                  15

Gly Val Gly Leu Asp Pro
            20

<210> SEQ ID NO 108
<211> LENGTH: 6
<212> TYPE: PRT
<213> ORGANISM: Artificial Sequence
<220> FEATURE:
<223> OTHER INFORMATION: CDRL1 aa

<400> SEQUENCE: 108

Lys Leu Gly Lys Lys Tyr
1               5

```
<210> SEQ ID NO 109
<211> LENGTH: 3
<212> TYPE: PRT
<213> ORGANISM: Artificial Sequence
<220> FEATURE:
<223> OTHER INFORMATION: CDRL2 aa

<400> SEQUENCE: 109

Gln Asp Thr
1

<210> SEQ ID NO 110
<211> LENGTH: 10
<212> TYPE: PRT
<213> ORGANISM: Artificial Sequence
<220> FEATURE:
<223> OTHER INFORMATION: CDRL3 aa

<400> SEQUENCE: 110

Gln Ala Trp Asp Ser Thr Thr His Val Ile
1               5                   10

<210> SEQ ID NO 111
<211> LENGTH: 24
<212> TYPE: DNA
<213> ORGANISM: Artificial Sequence
<220> FEATURE:
<223> OTHER INFORMATION: CDRH1 nuc

<400> SEQUENCE: 111
ggattcacct tcagtaggta cgac                                           24

<210> SEQ ID NO 112
<211> LENGTH: 21
<212> TYPE: DNA
<213> ORGANISM: Artificial Sequence
<220> FEATURE:
<223> OTHER INFORMATION: CDRH2 nuc

<400> SEQUENCE: 112
attactactg ctggtgacac a                                              21

<210> SEQ ID NO 113
<211> LENGTH: 66
<212> TYPE: DNA
<213> ORGANISM: Artificial Sequence
<220> FEATURE:
<223> OTHER INFORMATION: CDRH3 nuc

<400> SEQUENCE: 113
gcaagagggc ccccgaccga ttgtagtagt ggtcgctgct tagggrtcgg agtgggcttt    60
gacccc                                                               66

<210> SEQ ID NO 114
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 114
aaattgggga aaaaatat                                                  18

<210> SEQ ID NO 115
```

-continued

```
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 115 caagatacc                                                                   9

<210> SEQ ID NO 116
<211> LENGTH: 30
<212> TYPE: DNA
<213> ORGANISM: Artificial Sequence
<220> FEATURE:
<223> OTHER INFORMATION: CDRL3 nuc

<400> SEQUENCE: 116
caggcgtggg acagcaccac tcatgtaata                                           30

<210> SEQ ID NO 117
<211> LENGTH: 128
<212> TYPE: PRT
<213> ORGANISM: Artificial Sequence
<220> FEATURE:
<223> OTHER INFORMATION: heavy ch aa

<400> SEQUENCE: 117

Glu Val Gln Leu Val Glu Ser Gly Gly Gly Trp Val Gln Pro Gly Gly
 1               5                  10                  15

Ser Leu Arg Leu Ser Cys Ala Ala Ser Gly Phe Thr Phe Ser Arg Tyr
            20                  25                  30

Asp Met His Trp Val Arg Gln Val Thr Gly Lys Gly Leu Glu Trp Val
        35                  40                  45

Ser Ala Ile Thr Thr Ala Gly Asp Thr Tyr Tyr Pro Asp Ser Val Lys
    50                  55                  60

Gly Arg Phe Thr Ile Ser Arg Glu Asn Ala Lys Ser Ser Leu Tyr Leu
65                  70                  75                  80

Gln Met Asn Asn Leu Arg Ala Gly Asp Thr Ala Leu Tyr Tyr Cys Ala
                85                  90                  95

Arg Gly Pro Pro Thr Asp Cys Ser Ser Gly Arg Cys Leu Gly Val Gly
            100                 105                 110

Val Gly Leu Asp Pro Trp Gly Gln Gly Thr Leu Val Thr Val Ser Ser
        115                 120                 125

<210> SEQ ID NO 118
<211> LENGTH: 107
<212> TYPE: PRT
<213> ORGANISM: Artificial Sequence
<220> FEATURE:
<223> OTHER INFORMATION: light ch aa

<400> SEQUENCE: 118

Ser Tyr Glu Val Thr Gln Pro Pro Ser Val Ser Val Ser Pro Gly Gln
 1               5                  10                  15

Thr Ala Ser Ile Thr Cys Ser Gly Asp Lys Leu Gly Lys Lys Tyr Thr
            20                  25                  30

Ser Trp Tyr Gln Gln Lys Pro Gly Gln Ser Pro Leu Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
```

```
                65                  70                  75                  80
Asp Glu Ala Asp Tyr Tyr Cys Gln Ala Trp Asp Ser Thr Thr His Val
                        85                  90                  95

Ile Phe Gly Gly Gly Thr Lys Leu Thr Val Leu
                100                 105

<210> SEQ ID NO 119
<211> LENGTH: 385
<212> TYPE: DNA
<213> ORGANISM: Artificial Sequence
<220> FEATURE:
<223> OTHER INFORMATION: heavy ch nuc

<400> SEQUENCE: 119
gaggtgcagc tggttgagtc tgggggaggc tgggtacagc ctgggggtc cctgagactc      60 tcctgtgcag cctctggatt caccttcagt aggtacgaca tgcactgggt ccgccaagtc    120
acaggcaaag gtctggagtg ggtctcagct attactactg ctggtgacac atactatcct   180
gactccgtga agggccgatt caccatctcc agagaaaatg ccaagagctc cttgtatctc    240
caaatgaaca acctgagagc cggggacacg gctctttatt actgtgcaag agggcccccg    300
accgattgta gtagtggtcg ctgcttaggg gtcggagtgg ggcttgaccc ctggggccag    360
ggaaccctgg tcaccgtctc ctcag                                         385

<210> SEQ ID NO 120
<211> LENGTH: 322
<212> TYPE: DNA
<213> ORGANISM: Artificial Sequence
<220> FEATURE:
<223> OTHER INFORMATION: light ch nuc

<400> SEQUENCE: 120
tcctatgaag tgactcagcc accctcagtg tccgtgtccc caggacagac agccagcatc    60
acctgctctg gagataaatt ggggaaaaaa tatacttcct ggtatcagca gaagccaggc    120
cagtcccctc tactggtcat ctatcaagat accaagcggc cctcagggat ccctgagcgg    180
ttctctggct ccaactctgg gaacacagcc actctgacca tcagcgggac ccaggctatg    240
gatgaggctg actattactg tcaggcgtgg gacagcacca ctcatgtaat attcggcgga    300
gggaccaagc tgaccgtcct ag                                            322

<210> SEQ ID NO 121
<211> LENGTH: 8
<212> TYPE: PRT
<213> ORGANISM: Artificial Sequence
<220> FEATURE:
<223> OTHER INFORMATION: CDRH1 aa

<400> SEQUENCE: 121

Gly Tyr Thr Phe Thr Asn Tyr Tyr
1               5

<210> SEQ ID NO 122
<211> LENGTH: 8
<212> TYPE: PRT
<213> ORGANISM: Artificial Sequence
<220> FEATURE:
<223> OTHER INFORMATION: CDRH2 aa

<400> SEQUENCE: 122

Ile Asp Pro Thr Gly Gly Thr Thr
1               5
```

```
<210> SEQ ID NO 123
<211> LENGTH: 20
<212> TYPE: PRT
<213> ORGANISM: Artificial Sequence
<220> FEATURE:
<223> OTHER INFORMATION: CDRH3 aa

<400> SEQUENCE: 123

Ala Arg Gly Gly Gly Tyr Ser Arg Asn Trp Tyr Ser Tyr Gln Asn Tyr
1               5                   10                  15

Gly Leu Asp Val
            20

<210> SEQ ID NO 124
<211> LENGTH: 3
<212> TYPE: PRT
<213> ORGANISM: Artificial Sequence
<220> FEATURE:
<223> OTHER INFORMATION: CDRL2 aa

<400> SEQUENCE: 124

Gly Asn Ser
1

<210> SEQ ID NO 125
<211> LENGTH: 11
<212> TYPE: PRT
<213> ORGANISM: Artificial Sequence
<220> FEATURE:
<223> OTHER INFORMATION: CDRL3 aa

<400> SEQUENCE: 125

Gln Ser Tyr Asp Ser Ser Leu Ser Gly Phe Val
1               5                   10

<210> SEQ ID NO 126
<211> LENGTH: 24
<212> TYPE: DNA
<213> ORGANISM: Artificial Sequence
<220> FEATURE:
<223> OTHER INFORMATION: CDRH1 nuc

<400> SEQUENCE: 126
ggatacactt tcaccaacta ctat                                          24

<210> SEQ ID NO 127
<211> LENGTH: 24
<212> TYPE: DNA
<213> ORGANISM: Artificial Sequence
<220> FEATURE:
<223> OTHER INFORMATION: CDRH2 nuc

<400> SEQUENCE: 127
atcgacccta ctggtggtac cacc                                          24

<210> SEQ ID NO 128
<211> LENGTH: 60
<212> TYPE: DNA
<213> ORGANISM: Artificial Sequence
<220> FEATURE:
<223> OTHER INFORMATION: CDRH3 nuc

<400> SEQUENCE: 128
gcgagagggg gaggatatag tcgcaactgg tacagctacc agaattacgg tttggacgtc   60
```

<210> SEQ ID NO 129
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 129 ggtaatagc                                                                  9

<210> SEQ ID NO 130
<211> LENGTH: 33
<212> TYPE: DNA
<213> ORGANISM: Artificial Sequence
<220> FEATURE:
<223> OTHER INFORMATION: CDRL3 nuc

<400> SEQUENCE: 130
cagtcctatg acagcagcct gagtggtttt gtc                                      33

<210> SEQ ID NO 131
<211> LENGTH: 127
<212> TYPE: PRT
<213> ORGANISM: Artificial Sequence
<220> FEATURE:
<223> OTHER INFORMATION: heavy ch aa

<400> SEQUENCE: 131

Gln Val Gln Leu Val Gln Ser Gly Ala Glu Val Lys Lys Pro Gly Ala
1               5                   10                  15

Ser Val Arg Leu Ser Cys Lys Ala Ser Gly Tyr Thr Phe Thr Asn Tyr
            20                  25                  30

Tyr Leu His Trp Val Arg Gln Ala Pro Gly Gln Gly Leu Glu Trp Met
        35                  40                  45

Gly Ile Ile Asp Pro Thr Gly Gly Thr Thr Pro Tyr Ala Gln Lys Phe
    50                  55                  60

His Gly Arg Phe Thr Met Thr Ser Asp Thr Ser Thr Ser Thr Val Phe
65                  70                  75                  80

Met Glu Leu Ser Ser Leu Arg Leu Asp Asp Thr Ala Val Tyr Tyr Cys
                85                  90                  95

Ala Arg Gly Gly Gly Tyr Ser Arg Asn Trp Tyr Ser Tyr Gln Asn Tyr
            100                 105                 110

Gly Leu Asp Val Trp Gly Arg Gly Thr Thr Val Thr Val Ser Ser
        115                 120                 125

<210> SEQ ID NO 132
<211> LENGTH: 111
<212> TYPE: PRT
<213> ORGANISM: Artificial Sequence
<220> FEATURE:
<223> OTHER INFORMATION: light ch aa

<400> SEQUENCE: 132

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Phe Pro Gly Thr Ala Pro Lys Leu
        35                  40                  45

Leu Ile Tyr Gly Asn Ser Asp Arg Pro Ser Gly Val Pro Asp Arg Phe
    50                  55                  60

```
Ser Gly Ser Gln Ser Gly Thr Ser Ala Ser Leu Ala Ile Thr Glu Leu
 65                  70                  75                  80

Gln Ala Ala Asp Glu Ala Asp Phe Tyr Cys Gln Ser Tyr Asp Ser Ser
                 85                  90                  95

Leu Ser Gly Phe Val Phe Gly Thr Gly Thr Lys Val Thr Val Leu
            100                 105                 110

<210> SEQ ID NO 133
<211> LENGTH: 381
<212> TYPE: DNA
<213> ORGANISM: Artificial Sequence
<220> FEATURE:
<223> OTHER INFORMATION: heavy ch nuc

<400> SEQUENCE: 133
caggtacagc tggtacagtc tggggctgag gtgaagaagc ctggggcctc agtgaggctt      60
tcctgtaagg catctggata cactttcacc aactactatc tacactgggt gcgacaggcc    120
cctggacaag ggcttgagtg gatgggaata atcgacccta ctggtggtac cacccctac    180 gcgcagaagt tccatggcag attcaccatg accagtgaca cgtccacgag cacagtcttc    240
atggagttga gcagcctgag attagatgat acggccgtat attactgtgc gagagggga    300 ggatatagtc gcaactggta cagctaccag aattacggtt tggacgtctg ggccgaggg    360 accacagtca ccgtctcctc a                                              381

<210> SEQ ID NO 134
<211> LENGTH: 333
<212> TYPE: DNA
<213> ORGANISM: Artificial Sequence
<220> FEATURE:
<223> OTHER INFORMATION: light ch nuc

<400> SEQUENCE: 134
caggctgtgc tgacgcagcc gccctcagtg tctggggccc aggacagag ggtcaccatc      60 tcctgcactg ggagcagctc caacatcggg gcaggttatg atgtacactg gtaccagcag    120
tttccaggaa cagccccaa actcctcatt tatggtaata gcgatcggcc ctcagggtc    180 cctgaccgat tctctggctc ccagtctgga acttcagcct ccctggccat cactgagctc    240
caggctgcgg atgaggctga ttttactgc cagtcctatg acagcagcct gagtggtttt    300
gtcttcggaa ctgggaccaa ggtcaccgtc cta                                 333

<210> SEQ ID NO 135
<211> LENGTH: 8
<212> TYPE: PRT
<213> ORGANISM: Artificial Sequence
<220> FEATURE:
<223> OTHER INFORMATION: CDRH1 aa

<400> SEQUENCE: 135

Gly Phe Thr Phe Asn Arg Ser Trp
 1               5

<210> SEQ ID NO 136
<211> LENGTH: 8
<212> TYPE: PRT
<213> ORGANISM: Artificial Sequence
<220> FEATURE:
<223> OTHER INFORMATION: CDRH2 aa

<400> SEQUENCE: 136
```

Ile Ile Pro Asp Gly Ser Glu Lys
1               5

<210> SEQ ID NO 137
<211> LENGTH: 15
<212> TYPE: PRT
<213> ORGANISM: Artificial Sequence
<220> FEATURE:
<223> OTHER INFORMATION: CDRH3 aa

<400> SEQUENCE: 137

Ala Arg Val Ala Glu Phe Asp Tyr Val Trp Gly Ser Phe Asp Phe
1               5                   10                  15

<210> SEQ ID NO 138
<211> LENGTH: 6
<212> TYPE: PRT
<213> ORGANISM: Artificial Sequence
<220> FEATURE:
<223> OTHER INFORMATION: CDRL1 aa

<400> SEQUENCE: 138

Lys Leu Gly Tyr Lys Tyr
1               5

<210> SEQ ID NO 139
<211> LENGTH: 9
<212> TYPE: PRT
<213> ORGANISM: Artificial Sequence
<220> FEATURE:
<223> OTHER INFORMATION: CDRL3 aa

<400> SEQUENCE: 139

Gln Ala Trp Asp Ser Arg Thr Gly Val
1               5

<210> SEQ ID NO 140
<211> LENGTH: 24
<212> TYPE: DNA
<213> ORGANISM: Artificial Sequence
<220> FEATURE:
<223> OTHER INFORMATION: CDRH1 nuc

<400> SEQUENCE: 140
ggtttcacct ttaataggtc ttgg                                      24

<210> SEQ ID NO 141
<211> LENGTH: 24
<212> TYPE: DNA
<213> ORGANISM: Artificial Sequence
<220> FEATURE:
<223> OTHER INFORMATION: CDRH2 nuc

<400> SEQUENCE: 141
ataatcccag atggaagtga gaaa                                      24

<210> SEQ ID NO 142
<211> LENGTH: 45
<212> TYPE: DNA
<213> ORGANISM: Artificial Sequence
<220> FEATURE:
<223> OTHER INFORMATION: CDRH3 nuc

<400> SEQUENCE: 142
gcgagagtgg cggagtttga ttacgtttgg gggagttttg acttc                45

```
<210> SEQ ID NO 143
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 143
aaattgggat ataaatat                                                    18

<210> SEQ ID NO 144
<211> LENGTH: 27
<212> TYPE: DNA
<213> ORGANISM: Artificial Sequence
<220> FEATURE:
<223> OTHER INFORMATION: CDRL3 nuc

<400> SEQUENCE: 144
caggcgtggg acagccgcac tggggtg                                          27

<210> SEQ ID NO 145
<211> LENGTH: 122
<212> TYPE: PRT
<213> ORGANISM: Artificial Sequence
<220> FEATURE:
<223> OTHER INFORMATION: heavy ch aa

<400> SEQUENCE: 145

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Arg Ser
            20                  25                  30

Trp Met Asn Trp Val Arg Gln Ala Pro Gly Lys Gly Leu Glu Trp Val
        35                  40                  45

Ala Asn Ile Ile Pro Asp Gly Ser Glu Lys Tyr Tyr Met Asp Ser Val
    50                  55                  60

Lys Gly Arg Phe Thr Val Ser Arg Asp Asn Thr Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Val Ala Glu Phe Asp Tyr Val Trp Gly Ser Phe Asp Phe Trp
            100                 105                 110

Gly Gln Gly Thr Leu Val Thr Val Ser Ser
        115                 120

<210> SEQ ID NO 146
<211> LENGTH: 106
<212> TYPE: PRT
<213> ORGANISM: Artificial Sequence
<220> FEATURE:
<223> OTHER INFORMATION: light ch aa

<400> SEQUENCE: 146

Ser Tyr Glu Leu Thr Gln Thr Pro Ser Val Ser Val Ser Pro Gly His
 1               5                  10                  15

Ala Ala Ser Ile Thr Cys Ser Gly Asp Lys Leu Gly Tyr Lys Tyr Thr
            20                  25                  30

Ser Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60
```

```
Asn Ser Gly Asn Thr Ala Thr Leu Thr Ile Ser Ala Thr Gln Ala Met
 65                  70                  75                  80

Asp Glu Ala Asp Tyr Tyr Cys Gln Ala Trp Asp Ser Arg Thr Gly Val
                 85                  90                  95

Phe Gly Gly Gly Thr Lys Leu Thr Val Leu
            100                 105

<210> SEQ ID NO 147
<211> LENGTH: 367
<212> TYPE: DNA
<213> ORGANISM: Artificial Sequence
<220> FEATURE:
<223> OTHER INFORMATION: heavy ch nuc

<400> SEQUENCE: 147
gaggtgcagt tggtggagtc gggggggaggc ttggtccagc ctgggggggtc cctgagactc      60 tcctgtgcag cctctggttt cacctttaat aggtcttgga tgaactgggt ccgccaggct     120
ccagggaagg ggctggagtg ggtggccaat ataatcccag atggaagtga aaatactat      180 atggactctg tgaagggccg attcaccgtc tccagagaca caccaagaa ctcagtgtat      240 ctgcaaatga acagcctgag agccgaggac acggctgtct attactgtgc gagagtggcg     300
gagtttgatt acgtttgggg gagttttgac ttctggggcc agggaacccct ggtcaccgtc    360 tcctctg                                                                367

<210> SEQ ID NO 148
<211> LENGTH: 319
<212> TYPE: DNA
<213> ORGANISM: Artificial Sequence
<220> FEATURE:
<223> OTHER INFORMATION: light ch nuc

<400> SEQUENCE: 148
tcctatgagt tgactcagac accctcagtg tccgtgtccc caggacacgc agccagcatc      60
acctgctctg gagataaatt gggatataaa tatacttcct ggtatcaaca gaagccaggc     120 cagtccctg tgctggtcat ctatcaagat accaagcggc cctcagggat ccctgagcga     180
ttctctggct ccaactctgg gaacacagcc actctgacca tcagcgcgac ccaggctatg    240
gatgaggctg actattactg tcaggcgtgg gacagccgca ctgggtgtt cggcggaggg      300 accaaactga ccgtcctgg                                                   319

<210> SEQ ID NO 149
<211> LENGTH: 8
<212> TYPE: PRT
<213> ORGANISM: Artificial Sequence
<220> FEATURE:
<223> OTHER INFORMATION: CDRH1 aa var1

<400> SEQUENCE: 149

Gly Phe Thr Phe Ser Arg Ser Trp
  1               5

<210> SEQ ID NO 150
<211> LENGTH: 18
<212> TYPE: DNA
<213> ORGANISM: Artificial Sequence
<220> FEATURE:
<223> OTHER INFORMATION: CDRH1 nuc var1

<400> SEQUENCE: 150
aaattgggat ataaatat                                                     18
```

<210> SEQ ID NO 151
<211> LENGTH: 122
<212> TYPE: PRT
<213> ORGANISM: Artificial Sequence
<220> FEATURE:
<223> OTHER INFORMATION: heavy ch aa var1

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Ser
            20                  25                  30

Trp Met Asn Trp Val Arg Gln Ala Pro Gly Lys Gly Leu Glu Trp Val
        35                  40                  45

Ala Asn Ile Ile Pro Asp Gly Ser Glu Lys Tyr Tyr Met Asp Ser Val
    50                  55                  60

Lys Gly Arg Phe Thr Val Ser Arg Asp Asn Thr Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Val Ala Glu Phe Asp Tyr Val Trp Gly Ser Phe Asp Phe Trp
            100                 105                 110

Gly Gln Gly Thr Leu Val Thr Val Ser Ser
        115                 120

<210> SEQ ID NO 152
<211> LENGTH: 367
<212> TYPE: DNA
<213> ORGANISM: Artificial Sequence
<220> FEATURE:
<223> OTHER INFORMATION: heavy ch nuc var1

<400> SEQUENCE: 152
gaggtgcagt tggtggagtc ggggggaggc ttggtccagc ctggggggtc cctgagactc    60
tcctgtgcag cctctggttt cacctttagt aggtcttgga tgaactgggt ccgccaggct   120
ccagggaagg ggctggagtg ggtggccaat ataatcccag atggaagtga aaatactat    180
atggactctg tgaagggccg attcaccgtc tccagagaca acaccaagaa ctcagtgtat   240
ctgcaaatga acagcctgag agccgaggac acggctgtct attactgtgc gagagtggcg   300
gagtttgatt acgtttgggg gagttttgac ttctggggcc agggaaccct ggtcaccgtc   360
tcctctg                                                              367

<210> SEQ ID NO 153
<211> LENGTH: 8
<212> TYPE: PRT
<213> ORGANISM: Artificial Sequence
<220> FEATURE:
<223> OTHER INFORMATION: CDRH1 aa

<400> SEQUENCE: 153

Gly Phe Thr Phe Ser Tyr Ala Trp
1               5

<210> SEQ ID NO 154
<211> LENGTH: 10
<212> TYPE: PRT
<213> ORGANISM: Artificial Sequence
<220> FEATURE:
<223> OTHER INFORMATION: CDRH2 aa

<400> SEQUENCE: 154

Ile Lys Ser Lys Met Asn Gly Glu Thr Thr
1               5                   10

<210> SEQ ID NO 155
<211> LENGTH: 16
<212> TYPE: PRT
<213> ORGANISM: Artificial Sequence
<220> FEATURE:
<223> OTHER INFORMATION: CDRH3 aa

<400> SEQUENCE: 155

Ile Thr Asp Pro Gly Asn Ala Gly Ser Ala Ser Tyr Gly Met Asp Val
1               5                   10                  15

<210> SEQ ID NO 156
<211> LENGTH: 11
<212> TYPE: PRT
<213> ORGANISM: Artificial Sequence
<220> FEATURE:
<223> OTHER INFORMATION: CDRL1 aa

<400> SEQUENCE: 156

Gln Ser Leu Leu His Ser Asp Gly Lys Thr Tyr
1               5                   10

<210> SEQ ID NO 157
<211> LENGTH: 3
<212> TYPE: PRT
<213> ORGANISM: Artificial Sequence
<220> FEATURE:
<223> OTHER INFORMATION: CDRL1 aa

<400> SEQUENCE: 157

Glu Val Ser
1

<210> SEQ ID NO 158
<211> LENGTH: 8
<212> TYPE: PRT
<213> ORGANISM: Artificial Sequence
<220> FEATURE:
<223> OTHER INFORMATION: CDRL3 aa

<400> SEQUENCE: 158

Met Gln Ser Val Gln Ser Leu Gly
1               5

<210> SEQ ID NO 159
<211> LENGTH: 24
<212> TYPE: DNA
<213> ORGANISM: Artificial Sequence
<220> FEATURE:
<223> OTHER INFORMATION: CDRH1 nuc

<400> SEQUENCE: 159
ggattcactt tcagttacgc ctgg                                              24

<210> SEQ ID NO 160
<211> LENGTH: 30
<212> TYPE: DNA
<213> ORGANISM: Artificial Sequence
<220> FEATURE:
<223> OTHER INFORMATION: CDRH2 nuc

<400> SEQUENCE: 160

-continued

```
attaaaagca aaatgaatgg cgagacaaca                                              30
```

<210> SEQ ID NO 161
<211> LENGTH: 48
<212> TYPE: DNA
<213> ORGANISM: Artificial Sequence
<220> FEATURE:
<223> OTHER INFORMATION: CDRH3 nuc

<400> SEQUENCE: 161

```
atcacagacc ctgggaacgc tggttcggcg agttacggaa tggacgtt                          48
```

<210> SEQ ID NO 162
<211> LENGTH: 33
<212> TYPE: DNA
<213> ORGANISM: Artificial Sequence
<220> FEATURE:
<223> OTHER INFORMATION: CDRL1 nuc

<400> SEQUENCE: 162

```
cagagcctcc tgcatagtga tggaaagacc tat                                          33
```

<210> SEQ ID NO 163
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 163

```
gaagtttcc                                                                      9
```

<210> SEQ ID NO 164
<211> LENGTH: 24
<212> TYPE: DNA
<213> ORGANISM: Artificial Sequence
<220> FEATURE:
<223> OTHER INFORMATION: CDRL3 nuc

<400> SEQUENCE: 164

```
atgcaaagtg tacagtccct cggt                                                    24
```

<210> SEQ ID NO 165
<211> LENGTH: 125
<212> TYPE: PRT
<213> ORGANISM: Artificial Sequence
<220> FEATURE:
<223> OTHER INFORMATION: heavy ch aa

<400> SEQUENCE: 165

Glu Glu Gln Leu Val Glu Ser Gly Gly Gly Leu Val Lys Pro Gly Gly
1               5                   10                  15

Ser Leu Arg Leu Ser Cys Gly Ala Ser Gly Phe Thr Phe Ser Tyr Ala
            20                  25                  30

Trp Met Ser Trp Val Arg Gln Ala Pro Gly Lys Gly Leu Glu Trp Val
        35                  40                  45

Ala Arg Ile Lys Ser Lys Met Asn Gly Glu Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Ser Ser Leu Lys Thr Glu Asp Thr Ala Val Tyr
                85                  90                  95

Tyr Cys Ile Thr Asp Pro Gly Asn Ala Gly Ser Ala Ser Tyr Gly Met
            100                 105                 110

Asp Val Trp Gly Gln Gly Thr Thr Val Thr Val Ser Ser
        115                 120                 125

<210> SEQ ID NO 166
<211> LENGTH: 111
<212> TYPE: PRT
<213> ORGANISM: Artificial Sequencel
<220> FEATURE:
<223> OTHER INFORMATION: light ch aa

<400> SEQUENCE: 166

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ala
        35                  40                  45

Pro Gln Leu Leu Ile Phe Glu Val Ser Thr Arg Phe Pro Gly Val Pro
    50                  55                  60

His Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Val Gln Ser Leu Gly Phe Gly Gly Gly Thr Lys Val Glu Ile Lys
            100                 105                 110

<210> SEQ ID NO 167
<211> LENGTH: 376
<212> TYPE: DNA
<213> ORGANISM: Artificial Sequence
<220> FEATURE:
<223> OTHER INFORMATION: heavy ch nuc

<400> SEQUENCE: 167
gaggagcagc tggtggagtc tgggggaggc ttggtaaagc ctgggggggtc ccttagactc      60 tcgtgtggag cctctggatt cactttcagt tacgcctgga tgagttgggt ccgccaggct     120
ccaggcaagg gctggagtg gttgcccgt attaaaagca aaatgaatgg cgagacaaca        180
gactacgctg cacccgtgaa aggcagattc accatctcaa gagatgattc aaaaaacacg     240
ctgtatctgc aaatgagtag cctgaaaacc gaggacacag ccgtctatta ttgtatcaca     300 gacccctggga acgctggttc ggcgagttac ggaatggacg tttggggcca agggaccacg    360
gtcaccgtct cctcag                                                     376

<210> SEQ ID NO 168
<211> LENGTH: 334
<212> TYPE: DNA
<213> ORGANISM: Artificial Sequence
<220> FEATURE:
<223> OTHER INFORMATION: light ch nuc

<400> SEQUENCE: 168
gatattgtga tgacccagac tccactctct ctgtccgtca cccctggaca gccggcctcc      60
atctcctgca agtctagtca gagcctcctg catagtgatg gaaagaccta tttgtattgg     120
tatctgcaga agccaggcca ggctccacaa ctcctgattt ttgaagtttc cacccggttc     180
cctggagtgc cacataggtt cagtggcagc gggtcaggga cagatttcac actgaaaatc     240
agccgggtgg aggctgagga tgttggggtt tattactgca tgcaaagtgt acagtccctc    300
ggtttcggcg agggaccaa ggtggagatc aaac    334

<210> SEQ ID NO 169
<211> LENGTH: 8
<212> TYPE: PRT
<213> ORGANISM: Artificial Sequence
<220> FEATURE:
<223> OTHER INFORMATION: CDRH1 aa

<400> SEQUENCE: 169

Gly Phe Thr Phe Asn Thr Phe Asp
1               5

<210> SEQ ID NO 170
<211> LENGTH: 8
<212> TYPE: PRT
<213> ORGANISM: Artificial Sequence
<220> FEATURE:
<223> OTHER INFORMATION: CDRH2 aa

<400> SEQUENCE: 170

Ile Ser Gly Ser Ser Ser Tyr Ile
1               5

<210> SEQ ID NO 171
<211> LENGTH: 15
<212> TYPE: PRT
<213> ORGANISM: Artificial Sequence
<220> FEATURE:
<223> OTHER INFORMATION: CDRH3 aa

<400> SEQUENCE: 171

Ser Arg Val Leu Trp Asp Ser Ser Thr Gly Thr Phe Asp Ser
1               5                   10                  15

<210> SEQ ID NO 172
<211> LENGTH: 6
<212> TYPE: PRT
<213> ORGANISM: Artificial Sequence
<220> FEATURE:
<223> OTHER INFORMATION: CDRL1 aa

<400> SEQUENCE: 172

Asn Ile Gly Ser Lys Ser
1               5

<210> SEQ ID NO 173
<211> LENGTH: 3
<212> TYPE: PRT
<213> ORGANISM: Artificial Sequence
<220> FEATURE:
<223> OTHER INFORMATION: CDRL2 aa

<400> SEQUENCE: 173

Asp Asp Ser
1

<210> SEQ ID NO 174
<211> LENGTH: 12
<212> TYPE: PRT
<213> ORGANISM: Artificial Sequence
<220> FEATURE:
<223> OTHER INFORMATION: CDRL3 aa

<400> SEQUENCE: 174

```
Gln Val Trp Asp Ser Ser Ser Gly Pro Phe Val Val
1               5                   10
```

<210> SEQ ID NO 175
<211> LENGTH: 24
<212> TYPE: DNA
<213> ORGANISM: Artificial Sequence
<220> FEATURE:
<223> OTHER INFORMATION: CDRH1 nuc

<400> SEQUENCE: 175
ggattcacct tcaataccct tgac                                          24

<210> SEQ ID NO 176
<211> LENGTH: 24
<212> TYPE: DNA
<213> ORGANISM: Artificial Sequence
<220> FEATURE:
<223> OTHER INFORMATION: CDRH2 nuc

<400> SEQUENCE: 176
attagtggta gtagtagtta cata                                          24

<210> SEQ ID NO 177
<211> LENGTH: 45
<212> TYPE: DNA
<213> ORGANISM: Artificial Sequence
<220> FEATURE:
<223> OTHER INFORMATION: CDRH3 nuc

<400> SEQUENCE: 177
tcgagagtgc tgtgggacag cagctcgact ggcacctttg actct                   45

<210> SEQ ID NO 178
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 178
aacattggaa gtaaaagt                                                 18

<210> SEQ ID NO 179
<211> LENGTH: 9
<212> TYPE: DNA
<213> ORGANISM: Artificial Sequence
<220> FEATURE:
<223> OTHER INFORMATION: CDRL2 nuc

<400> SEQUENCE: 179 gatgatagc                                                            9

<210> SEQ ID NO 180
<211> LENGTH: 36
<212> TYPE: DNA
<213> ORGANISM: Artificial Sequence
<220> FEATURE:
<223> OTHER INFORMATION: CDRL3 NUC

<400> SEQUENCE: 180
caggtgtggg atagtagtag tggtcctttt gtggtt                             36

<210> SEQ ID NO 181
<211> LENGTH: 122
<212> TYPE: PRT

<213> ORGANISM: Artificial Sequence
<220> FEATURE:
<223> OTHER INFORMATION: heavy ch aa

<400> SEQUENCE: 181

```
Glu Val Gln Leu Val Glu Ser Gly Gly Gly Leu Val Arg Pro Gly Gly
1               5                   10                  15
Ser Leu Arg Leu Ser Cys Ala Ala Ser Gly Phe Thr Phe Asn Thr Phe
            20                  25                  30
Asp Met Asn Trp Val Arg Gln Ala Pro Gly Arg Gly Leu Glu Trp Val
        35                  40                  45
Ser Ser Ile Ser Gly Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ser Arg Val Leu Trp Asp Ser Ser Thr Gly Thr Phe Asp Ser Trp
            100                 105                 110
Gly Gln Gly Thr Arg Val Thr Val Ser Ser
        115                 120
```

<210> SEQ ID NO 182
<211> LENGTH: 109
<212> TYPE: PRT
<213> ORGANISM: Artificial Sequence
<220> FEATURE:
<223> OTHER INFORMATION: light ch aa

<400> SEQUENCE: 182

```
Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Leu Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Gly Pro
                85                  90                  95
Phe Val Val Phe Gly Gly Gly Thr Lys Leu Thr Val Leu
            100                 105
```

<210> SEQ ID NO 183
<211> LENGTH: 367
<212> TYPE: DNA
<213> ORGANISM: Artificial Sequence
<220> FEATURE:
<223> OTHER INFORMATION: heavy ch nuc

<400> SEQUENCE: 183

```
gaggtgcagc tggtggagtc tgggggaggc ctggtcaggc ctggggggtc cctgagactc      60
tcctgtgcag cctctggatt caccttcaat acctttgaca tgaactgggt ccgccaggct     120
ccagggaggg gctggagtg gtctctcatcc attagtggta gtagtagtta catatactac     180
gcagactcag tgaagggccg attcaccatc tccagagaca cgccaagaa ctcactgtat     240
```

```
ctgcaaatga acagcctgag agccgaggac acggctgtgt attattgttc gagagtgctg    300
tgggacagca gctcgactgg cacctttgac tcttgggggc agggaacccg ggtcaccgtc    360
tcctcag                                                              367
```

<210> SEQ ID NO 184
<211> LENGTH: 328
<212> TYPE: DNA
<213> ORGANISM: Artificial Sequence
<220> FEATURE:
<223> OTHER INFORMATION: light ch nuc

<400> SEQUENCE: 184

```
tcctatgtgc tgactcagcc accctcggtg tcagtggccc caggacagac ggccaggatt     60
acctgtgggg gaaacaacat tggaagtaaa agtgtgcact ggtaccagca gaagccaggc    120
caggcccctg tgctggtcgt ctatgatgat agcgaccggc cctcagggat ccctgagcga    180
ctctctggct ccaactctgg gaacacggcc accctgacca tcagcagggt cgaagccggg    240
gatgaggccg actattactg tcaggtgtgg gatagtagta gtggtccttt tgtggttttc    300
ggcggaggga ccaagctgac cgtcctag                                       328
```

<210> SEQ ID NO 185
<211> LENGTH: 10
<212> TYPE: PRT
<213> ORGANISM: Artificial Sequence
<220> FEATURE:
<223> OTHER INFORMATION: CDRH1 aa

<400> SEQUENCE: 185

```
Gly Gly Ser Val Ser Ser Gly Ser Tyr Tyr
1               5                   10
```

<210> SEQ ID NO 186
<211> LENGTH: 7
<212> TYPE: PRT
<213> ORGANISM: Artificial Sequence
<220> FEATURE:
<223> OTHER INFORMATION: CDRH2 aa

<400> SEQUENCE: 186

```
Ile Tyr Tyr Ser Gly Pro Thr
1               5
```

<210> SEQ ID NO 187
<211> LENGTH: 11
<212> TYPE: PRT
<213> ORGANISM: Artificial Sequence
<220> FEATURE:
<223> OTHER INFORMATION: CDRH3 aa

<400> SEQUENCE: 187

```
Ala Arg Ala Phe Ala Lys Asn Trp Phe Asp Pro
1               5                   10
```

<210> SEQ ID NO 188
<211> LENGTH: 6
<212> TYPE: PRT
<213> ORGANISM: Artificial Sequence
<220> FEATURE:
<223> OTHER INFORMATION: CDRL1 aa

<400> SEQUENCE: 188

```
Asn Ile Gly Ser Arg Asn
1               5
```

```
<210> SEQ ID NO 189
<211> LENGTH: 11
<212> TYPE: PRT
<213> ORGANISM: Artificial Sequence
<220> FEATURE:
<223> OTHER INFORMATION: CDRL3 aa

<400> SEQUENCE: 189

Gln Val Trp Asp Gly Ser Ser Asp Val Ala Ile
1               5                   10

<210> SEQ ID NO 190
<211> LENGTH: 30
<212> TYPE: DNA
<213> ORGANISM: Artificial Sequence
<220> FEATURE:
<223> OTHER INFORMATION: CDRH1 nuc

<400> SEQUENCE: 190
ggtggctccg tcagcagtgg tagttactac                                    30

<210> SEQ ID NO 191
<211> LENGTH: 21
<212> TYPE: DNA
<213> ORGANISM: Artificial Sequence
<220> FEATURE:
<223> OTHER INFORMATION: CDRH2 nuc

<400> SEQUENCE: 191
atctattaca gtgggcccac c                                             21

<210> SEQ ID NO 192
<211> LENGTH: 33
<212> TYPE: DNA
<213> ORGANISM: Artificial Sequence
<220> FEATURE:
<223> OTHER INFORMATION: CDRH3 nuc

<400> SEQUENCE: 192
gcgagagcat ttgcgaagaa ctggttcgac ccc                                33

<210> SEQ ID NO 193
<211> LENGTH: 18
<212> TYPE: DNA
<213> ORGANISM: Artificial Sequence
<220> FEATURE:
<223> OTHER INFORMATION: CDRL1 nuc

<400> SEQUENCE: 193
aacattggaa gtcgaaat                                                 18

<210> SEQ ID NO 194
<211> LENGTH: 33
<212> TYPE: DNA
<213> ORGANISM: Artificial Sequence
<220> FEATURE:
<223> OTHER INFORMATION: CDRL3 nuc

<400> SEQUENCE: 194
caggtgtggg atggtagtag tgatgttgca att                                33

<210> SEQ ID NO 195
<211> LENGTH: 119
<212> TYPE: PRT
<213> ORGANISM: Artificial Sequence
```

<220> FEATURE:
<223> OTHER INFORMATION: heavy ch aa

<400> SEQUENCE: 195

Gln Val Gln Leu Gln Glu Ser Gly Pro Gly Leu Leu Lys Ala Ser Glu
1               5                   10                  15

Thr Leu Ser Leu Thr Cys Thr Val Ser Gly Gly Ser Val Ser Ser Gly
            20                  25                  30

Ser Tyr Tyr Trp Thr Trp Ile Arg Gln Pro Pro Gly Lys Gly Leu Glu
        35                  40                  45

Trp Ile Gly Tyr Ile Tyr Tyr Ser Gly Pro Thr Asn Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Arg Ser Val Thr Ala Ala Asp Thr Ala Val Tyr Tyr
                85                  90                  95

Cys Ala Arg Ala Phe Ala Lys Asn Trp Phe Asp Pro Trp Gly Gln Gly
            100                 105                 110

Thr Leu Val Thr Val Ser Ser
        115

<210> SEQ ID NO 196
<211> LENGTH: 108
<212> TYPE: PRT
<213> ORGANISM: Artificial Sequence
<220> FEATURE:
<223> OTHER INFORMATION: light ch aa

<400> SEQUENCE: 196

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Arg Asn Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp Val
                85                  90                  95

Ala Ile Phe Gly Gly Gly Thr Lys Leu Thr Val Leu
            100                 105

<210> SEQ ID NO 197
<211> LENGTH: 358
<212> TYPE: DNA
<213> ORGANISM: Artificial Sequence
<220> FEATURE:
<223> OTHER INFORMATION: heavy ch nuc

<400> SEQUENCE: 197
caggtgcagc tgcaggagtc gggcccagga ctgctgaagg cttcggagac cctgtctctc        60
acatgcactg tctctggtgg ctccgtcagc agtggtagtt actactggac ctggatccgg       120 cagccccag ggaagggact ggagtggatt ggctatatct attacagtgg gcccaccaac        180
tacaatccct ccctcaagag tcgagtcacc atgtcagtag acacgtccaa gaaccagttc       240
tccctgaagg tgaggtctgt gaccgctgcg gacacggccg tatattactg tgcgagagca       300

```
tttgcgaaga actggttcga ccccctgggggc cagggaaccc tggtcaccgt ctcctcag        358

<210> SEQ ID NO 198
<211> LENGTH: 325
<212> TYPE: DNA
<213> ORGANISM: Artificial Sequence
<220> FEATURE:
<223> OTHER INFORMATION: light ch nuc

<400> SEQUENCE: 198
tcctatgtgc tgactcagcc accctcagtg tcggtggccc caggaaagac ggccaggatt         60
acctgtgggg gaaacaacat tggaagtcga aatgtacact ggtaccagca gaagccaggc        120
caggcccctg tgttggtcat ctattatgat agcgaccggc cctcagggat ccctgagcga        180
ttctctggct ccaactctgg gaacacggcc accctgacca tcagcagggt cgaagccggg        240
gatgaggccg actattactg tcaggtgtgg gatggtagta gtgatgttgc aatttttggc        300
ggagggacca agctgaccgt cctag                                              325
```

DENGUE VIRUS NEUTRALIZING ANTIBODIES AND USE THEREOF

This application claims priority to U.S. Provisional Application Ser. No. 61/104,911, entitled "Dengue Virus Neutralizing Antibodies and Use Thereof," filed Oct. 13, 2008, which is incorporated herein by reference in its entirety.

BACKGROUND

Dengue viruses (DENV) are human pathogens with a significant threat to world health. These viruses are estimated to cause several hundred thousand cases of dengue fever, dengue hemorrhagic fever and dengue shock syndrome annually. There are four closely related serotypes of dengue viruses, DENV-1, DENV-2, DENV-3 and DENV-4, of the genus *Flavivirus*. The four viruses are spread from human to human through the bite of *Aedes aegypti*, a highly urbanized mosquito species that has successfully resisted all attempts at eradication and control. Vaccination is considered to be the only efficient method of control of dengue. To this end, several tetravalent dengue candidate vaccines are in late stages of development.

A first infection with one Dengue virus serotype induces a life-long protective immunity to the homologous serotype. However, there is no cross-protection against infection by a different serotype. Indeed, pre-existing immunity against one serotype is associated with increased risk for dengue infection and dengue hemorrhagic fever caused by a different serotype due to antibody-dependent enhancement (ADE) of infection. In ADE, antibodies raised by prior dengue infection or passively transferred from mother form infectious immune complexes that attach to Fc-receptor-bearing cells in the mononuclear phagocyte lineage resulting in efficient infection.

Accordingly, there is a need for materials and methods for preventing dengue virus infection without increasing the risk of antibody-dependent enhancement of infection.

SUMMARY

The invention is based, in part, on the discovery of antibodies and cocktails of antibodies that neutralize dengue virus infection without contributing to antibody-dependent enhancement of dengue virus infection. Accordingly, in one aspect of the invention, the invention comprises a human antibody, an antibody variant, or an antigen binding fragment thereof, that neutralize a dengue virus, wherein the antibody, antibody variant, or antigen binding fragment does not contribute to antibody-dependent enhancement of dengue virus infection. In one embodiment, the invention comprises a human antibody, an antibody variant, or an antigen binding fragment thereof, that neutralize a dengue virus, wherein the antibody, antibody variant, or antigen binding fragment comprises a mutation in the Fc region, and wherein the mutation reduces binding of the antibody to an Fc receptor.

In another embodiment of the invention, the invention comprises a pharmaceutical composition comprising two or more human antibodies, or antigen binding fragments thereof. The antibodies or antigen binding fragments neutralize dengue virus serotypes DENV-1, DENV-2, DENV-3, and DENV-4 by binding at least two distinct epitopes on each dengue virus serotype. The antibodies of the pharmaceutical composition do not contribute to antibody-dependent enhancement of dengue virus infection.

In yet another embodiment, the invention comprises an antibody, or an antigen binding fragment thereof, comprising at least one complementarity determining region (CDR) sequence having the sequence of any one of SEQ ID NOs: 1-6, 17-22, 33-38, 49-54, 67-72, 83-88, 99, 100, 105-110, 121-123, 124, 125, 135-139, 149, 153-158, 169-174, 185-188, or 189, wherein the antibody neutralizes dengue virus infection.

In yet another embodiment, the invention comprises an antibody, or an antigen binding fragment thereof, wherein the antibody comprises a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 45 and a light chain variable region comprising the amino acid sequence of SEQ ID NO: 46; or a heavy chain variable region comprising the amino acid sequence of SEQ ID NO: 61 and a light chain variable region comprising the amino acid sequence of SEQ ID NO: 62; or a heavy chain variable region comprising the amino acid sequence of SEQ ID NO: 65 and a light chain variable region comprising the amino acid sequence of SEQ ID NO: 62; or a heavy chain variable region comprising the amino acid sequence of SEQ ID NO: 79 and a light chain variable region comprising the amino acid sequence of SEQ ID NO: 80; or a heavy chain variable region comprising the amino acid sequence of SEQ ID NO: 95 and a light chain variable region comprising the amino acid sequence of SEQ ID NO: 96; or a heavy chain variable region comprising the amino acid sequence of SEQ ID NO: 95 and a light chain variable region comprising the amino acid sequence of SEQ ID NO: 103; or a heavy chain variable region comprising the amino acid sequence of SEQ ID NO: 117 and a light chain variable region comprising the amino acid sequence of SEQ ID NO: 118; or a heavy chain variable region comprising the amino acid sequence of SEQ ID NO: 131 and a light chain variable region comprising the amino acid sequence of SEQ ID NO: 132; or a heavy chain variable region comprising the amino acid sequence of SEQ ID NO: 145 and a light chain variable region comprising the amino acid sequence of SEQ ID NO: 146; or a heavy chain variable region comprising the amino acid sequence of SEQ ID NO: 151 and a light chain variable region comprising the amino acid sequence of SEQ ID NO: 146; or a heavy chain variable region comprising the amino acid sequence of SEQ ID NO: 165 and a light chain variable region comprising the amino acid sequence of SEQ ID NO: 166; or a heavy chain variable region comprising the amino acid sequence of SEQ ID NO: 181 and a light chain variable region comprising the amino acid sequence of SEQ ID NO: 182; or a heavy chain variable region comprising the amino acid sequence of SEQ ID NO: 195 and a light chain variable region comprising the amino acid sequence of SEQ ID NO: 196, wherein the antibody neutralizes dengue virus infection.

In a further embodiment, the invention comprises a recombinant antibody, antibody variant, or antigen binding fragment thereof, that can neutralize a dengue virus. The recombinant antibody, antibody variant, or antigen binding fragment does not contribute to antibody-dependent enhancement of dengue virus infection.

In another aspect, the invention comprises a nucleic acid molecule comprising a polynucleotide encoding an antibody or antibody fragment of the invention that neutralizes dengue virus infection. In yet another aspect, the invention comprises a cell expressing an antibody of the invention. In still another aspect, the invention comprises an isolated or purified immunogenic polypeptide comprising an epitope that binds to an antibody of the invention.

The invention also comprises a pharmaceutical composition comprising an antibody, an antibody variant or an antigen binding fragment of the invention, a nucleic acid of the invention, or an immunogenic polypeptide of the invention and a pharmaceutically acceptable diluent or carrier and, optionally, an agent useful for extending the half life of the antibody or antigen binding fragment thereof.

In another aspect of the invention, the invention provides a method of inhibiting or preventing dengue virus infection or a dengue virus-related disease or a method of treating dengue virus infection or a dengue virus-related disease. The method comprises administering to a subject in need thereof, a therapeutically effective amount of at least one antibody, antibody variant, antigen binding fragment, or a pharmaceutical composition of the invention.

In yet another aspect of the invention, the invention comprises a method of screening for polypeptides that can induce or reveal an immune response against dengue virus, comprising screening polypeptide libraries using an antibody, an antibody fragment or variant of the invention.

In yet another aspect of the invention, the invention comprises a method of monitoring the quality of anti-dengue virus vaccines. The method comprises using an antibody, an antibody variant, or an antigen binding fragment thereof of the invention to check that the antigen of the vaccine contains the specific epitope in the correct conformation.

In a further aspect of the invention, the invention comprises a vaccine comprising an epitope which specifically binds to an antibody, an antibody fragment or variant of the invention.

Use of an antibody of the invention, or an antigen binding fragment thereof, a nucleic acid of the invention, an immunogenic polypeptide of the invention, or a pharmaceutical composition of the invention (i) in the manufacture of a medicament for the treatment of dengue virus infection, (ii) in a vaccine, or (iii) in diagnosis of dengue virus infection is also contemplated to be within the scope of the invention. Further, use of an antibody of the invention, or an antigen binding fragment thereof, for monitoring the quality of anti-DENV vaccines by checking that the antigen of said vaccine contains the specific epitope in the correct conformation is also contemplated to be within the scope of the invention.

In a further aspect, the invention comprises an epitope which specifically binds to an antibody of any one of the invention, or an antigen binding fragment thereof, for use (i) in therapy, (ii) in the manufacture of a medicament for treating dengue virus infection, (iii) as a vaccine, or (iv) in screening for ligands able to neutralise dengue virus infection.

BRIEF DESCRIPTION OF FIGURES

FIG. 1. VERO cells and K562 cells were used in virus neutralization and enhancement assays with each serotype of dengue virus using wild-type anti-dengue virus antibodies. Antibodies to dengue virus inhibit infection of the target virus on VERO cells in a dose-dependent manner. On K562 cells, the antibodies lead to a dose dependent antibody-dependent enhancement (ADE) of infection.

FIG. 2. Anti-dengue virus antibodies that have a CH2 L4A and L5A substitution (LALA variants) in the heavy chain neutralize target virus infection on VERO cells as did the unmodified antibodies. However, the LALA variants completely abolished the antibody-dependent enhancement of infection by the target virus on K562 cells.

DETAILED DESCRIPTION OF THE INVENTION

The invention is based on the discovery of antibodies and cocktails of antibodies that neutralize dengue virus (DENV) infection without contributing to antibody-dependent enhancement (ADE) of dengue virus infection. In one aspect of the invention, the invention comprises a human antibody, a variant antibody, or an antigen binding fragment thereof, that neutralizes a dengue virus without contributing to antibody-dependent enhancement of dengue virus infection. The antibodies or antibody fragments can neutralize more than one dengue virus serotype, for example, 2, 3 or all 4 dengue virus serotypes DENV-1, DENV-2, DENV-3, and DENV-4.

The invention also comprises a pharmaceutical composition comprising, for example, an antibody cocktail that comprises two or more human antibodies, antibody variants or antigen binding fragments thereof. The pharmaceutical compositions of the invention comprising a cocktail of human antibodies, antibody fragments or variants neutralize all four dengue virus serotypes, i.e., DENV-1, DENV-2, DENV-3, and DENV-4. In one embodiment, the cocktail of antibodies, antibody fragments or variants neutralize dengue virus by binding at least two distinct epitopes on each dengue virus serotype. It is noted that the antibodies, variants and fragments of the pharmaceutical composition do not contribute to antibody-dependent enhancement of dengue virus infection. In one embodiment, the cocktail comprises two antibodies, fragments or variants thereof. In another embodiment, the cocktail comprises three antibodies, fragments or variants thereof. In yet another embodiment, the cocktail comprises more than 3 antibodies, e.g., 4, 5, 6, 7 or 8 antibodies.

As used herein, the terms "fragment," "antibody fragment," and "antigen binding fragment" are used interchangeably to refer to any fragment of an antibody of the invention that retains the antigen-binding activity of the antibody. Exemplary antibody fragments include, but are not limited to, Fab, Fab', F(ab')$_2$, Fv, and scFv fragments.

The terms "mutation," and "substitution" are used interchangeably to refer to a change in one or more nucleic acid or amino acid residues.

As used herein, the terms "variant," and "antibody variant" are used interchangeably to refer to any variant of an antibody of the invention that retains the antigen-binding activity of the antibodies. The term variant includes antibodies that comprise mutations and/or substitutions. Exemplary antibody variants include, but are not limited to, those that have an L to A substitution at position CH2 4, 5, or both.

Antibodies of the Invention

The invention provides antibodies that neutralize dengue virus, but do not contribute to ADE of dengue virus infection. A "neutralizing antibody" is one that can neutralize the ability of a pathogen to initiate and/or perpetuate an infection in a host. The antibodies of the invention are able to neutralize one or more dengue virus serotypes DENV-1, DENV-2, DENV-3, and DENV-4. In one embodiment, the antibody of the invention neutralizes more than one, e.g., 2, 3, or all 4 dengue virus serotypes. In another embodiment, a pharmaceutical composition comprising two or more antibodies, antibody fragments or variants can neutralize all 4 dengue virus serotypes. In yet another embodiment, the pharmaceutical composition comprising two or more antibodies, antibody fragments or variants neutralizes dengue virus infection by targeting two distinct epitopes on each dengue virus serotype. These antibodies, antigen binding fragment and variants can be used as prophylactic or therapeutic agents upon appropriate formulation, or as a diagnostic tool, as described herein.

The antibodies of the invention may be monoclonal, for example, human monoclonal antibodies, or recombinant antibodies. The invention also provides fragments of the antibodies of the invention, particularly fragments that retain the antigen-binding activity of the antibodies. Although the specification, including the claims, may, in some places, refer explicitly to antibody fragment(s), variant(s) and/or derivative(s) of antibodies, it is understood that the term "antibody" or "antibody of the invention" includes all categories of antibodies, namely, antibody fragment(s), variant(s) and derivative(s) of antibodies.

Without being bound to any theory, it is believed that antibody-dependent enhancement of dengue virus infection is brought about by the binding of the Fc region of the antibody, in particular, the Fc region of the heavy chain of an IgG molecule, to an Fc receptor, e.g., an Fcγ receptor on a host cell. The invention, on the other hand, provides antibodies, including IgG molecules, that have reduced binding to the Fc receptors (FcR). In one embodiment, the antibody of the invention comprises one or more mutations in the Fc region. The mutation(s) may be any mutation that reduces binding of the antibody to an Fc receptor. In one embodiment, the Fc region of an antibody of the invention comprises a substitution at positions CH2 4, 5, or both. In general, the amino acid at positions 4 and 5 of CH2 of the wild-type IgG1 and IgG3 is a leucine ("L"). In one embodiment, the antibodies of the invention comprise an amino acid at position CH2 4, 5, or both, that is not an L. In another embodiment, the antibodies of the invention comprise an alanine ("A") at position CH2 4, or 5, or both. An antibody comprising a CH2 L4A and an L5A substitution is referred to herein as a "LALA" variant.

Alternatively, the invention provides antibody fragments that do not comprise an Fc region and thus do not bind to an FcR. Exemplary antibody fragments include, but are not limited to, Fab, Fab', F(ab')$_2$, Fv and scFv.

The sequences of the heavy chains and light chains of several exemplary antibodies of the invention, each comprising three CDRs on the heavy chain and three CDRs on the light chain have been determined. The position of the CDR amino acids are defined according to the IMGT numbering system [1, 2, 3]. The sequences of the CDRs, heavy chains, light chains as well as the sequences of the nucleic acid molecules encoding the CDRs, heavy chains, light chains of many exemplary antibodies of the invention are disclosed in the sequence listing. Table 1 provides the SEQ ID NOs for the amino acid sequences of the six CDRs, the variable region of the heavy and light chains, respectively, of exemplary antibodies of the invention. Table 2 provides the SEQ ID NOs for the sequences of the nucleic acid molecules encoding the CDRs, heavy chains and light chains of exemplary antibodies of the invention.

TABLE 1

Amino Acid SEQ IDs for Antibody CDRs, Heavy and Light Chains

| Antibody | CDRs | Heavy Chain Variable Region | Light Chain Variable Region |
|---|---|---|---|
| HMB-DV-1 | 1-6 | 13 | 14 |
| HMB-DV-2 | 17-22 | 29 | 30 |
| HMB-DV-3 | 33-38 | 45 | 46 |
| HMB-DV-4 | 49-54 | 61, 65 | 62 |
| HMB-DV-5 | 67-72 | 79 | 80 |
| HMB-DV-6 | 83-88 | 95 | 96 |

TABLE 1-continued

Amino Acid SEQ IDs for Antibody CDRs, Heavy and Light Chains

| Antibody | CDRs | Heavy Chain Variable Region | Light Chain Variable Region |
|---|---|---|---|
| HMB-DV-7 | 83-85, 99, 53, 100 | 95 | 103 |
| HMB-DV-8 | 105-110 | 117 | 118 |
| HMB-DV-9 | 121-123, 70 124, 125 | 131 | 132 |
| HMB-DV-10 | 135-139, 109 | 145 | 146 |
| HMB-DV-11 | 149, 136-139, 109 | 151 | 146 |
| HMB-DV-12 | 153-158 | 165 | 166 |
| HMB-DV-13 | 169-174 | 181 | 182 |
| HMB-DV-14 | 185-188, 37, 189 | 195 | 196 |

TABLE 2

Nucleic Acid SEQ IDs for Antibody CDRs, Heavy and Light Chains

| Antibody | CDRs | Heavy Chain Variable Region | Light Chain Variable Region |
|---|---|---|---|
| HMB-DV-1 | 7-12 | 15 | 16 |
| HMB-DV-2 | 23-28 | 31 | 32 |
| HMB-DV-3 | 39-44 | 47 | 48 |
| HMB-DV-4 | 55-60 | 63, 66 | 64 |
| HMB-DV-5 | 73-78 | 81 | 82 |
| HMB-DV-6 | 89-94 | 97 | 98 |
| HMB-DV-7 | 89-91, 101, 59, 102 | 97 | 104 |
| HMB-DV-8 | 111-116 | 119 | 120 |
| HMB-DV-9 | 126-128, 76, 129, 130 | 133 | 134 |
| HMB-DV-10 | 140-143, 115, 144 | 147 | 148 |
| HMB-DV-11 | 150, 141-143, 115, 144 | 152 | 148 |
| HMB-DV-12 | 159-164 | 167 | 168 |
| HMB-DV-13 | 175-180 | 183 | 184 |
| HMB-DV-14 | 190-193, 43, 194 | 197 | 198 |

In one embodiment, the antibodies or antigen-binding fragments of the invention comprise one or more heavy or light chain CDRs of the exemplary antibodies of the invention. In an exemplary embodiment, the antibodies or antigen-binding fragments of the invention neutralize dengue virus infection and comprise at least one CDR sequence having the sequence of any one of SEQ ID NOs: 1-6, 17-22, 33-38, 49-54, 67-72, 83-88, 99, 100, 105-110, 121-123, 124, 125, 135-139, 149, 153-158, 169-174, 185-188, or 189.

In another embodiment, the antibodies, antibody variants or antigen binding fragments of the invention comprise a heavy chain comprising an amino acid sequence of one or more of SEQ ID NOs: 1-3, 17-19, 33-35, 49-51, 67-69, 83-85, 105-107, 121-123, 135-137, 149, 153-155, 169-171, or 185-187. In yet another embodiment, the antibodies, antibody variants or antigen binding fragments of the invention comprise a heavy chain CDR1 selected from the group consisting of SEQ ID NOs: 1, 17, 33, 49, 67, 83, 105, 121, 135, 149, 153, 169, and 185; a heavy chain CDR2 selected from the group consisting of SEQ ID NOs: 2, 18, 34, 50, 68, 84, 106, 122, 136, 154, 170, and 186; and a heavy chain CDR3 selected from the group consisting of SEQ ID NOs: 3, 19, 35, 51, 69, 85, 107, 123, 137, 155, 171, and 187.

For example, the antibodies of the invention comprise a heavy chain comprising SEQ ID NO: 1 for CDRH1, SEQ ID NO: 2 for CDRH2, SEQ ID NO: 3 for CDRH3; SEQ ID NO: 17 for CDRH1, SEQ ID NO: 18 for CDRH2 and SEQ ID NO: 19 for CDRH3; SEQ ID NO: 33 for CDRH1, SEQ ID NO: 34 for CDRH2 and SEQ ID NO: 35 for CDRH3; SEQ ID NO: 49 for CDRH1, SEQ ID NO: 50 for CDRH2 and SEQ ID NO: 51 for CDRH3; SEQ ID NO: 67 for CDRH1, SEQ ID NO: 68 for CDRH2 and SEQ ID NO: 69 for CDRH3; SEQ ID NO: 83 for CDRH1, SEQ ID NO: 84 for CDRH2 and SEQ ID NO: 85 for CDRH3; SEQ ID NO: 105 for CDRH1, SEQ ID NO: 106 for CDRH2 and SEQ ID NO: 107 for CDRH3; SEQ ID NO: 121 for CDRH1, SEQ ID NO: 122 for CDRH2 and SEQ ID NO: 123 for CDRH3; SEQ ID NO: 135 for CDRH1, SEQ ID NO: 136 for CDRH2 and SEQ ID NO: 137 for CDRH3; SEQ ID NO: 149 for CDRH1, SEQ ID NO: 136 for CDRH2 and SEQ ID NO: 137 for CDRH3; SEQ ID NO: 153 for CDRH1, SEQ ID NO: 154 for CDRH2 and SEQ ID NO: 155 for CDRH3; SEQ ID NO: 169 for CDRH1, SEQ ID NO: 170 for CDRH2 and SEQ ID NO: 171 for CDRH3; and SEQ ID NO: 185 for CDRH1, SEQ ID NO: 186 for CDRH2 and SEQ ID NO: 187 for CDRH3.

In yet another embodiment, the antibodies, antibody variants or antibody fragments of the invention comprise a light chain comprising an amino acid sequence of one or more of SEQ ID NOs: 4-6, 20-22, 36-38, 52-54, 70-72, 86-88, 99, 100, 108-110, 124, 125, 138, 139, 156-158, 172-174, 188, or 189. In a further embodiment, the antibodies, antibody variants or antibody fragments of the invention comprise a light chain CDR1 selected from the group consisting of SEQ ID NOs: 4, 20, 36, 52, 70, 86, 99, 108, 138, 156, 172, and 188; a light chain CDR2 selected from the group consisting of SEQ ID NOs: 5, 21, 37, 53, 71, 87, 109, 124, 157, and 173; and a light chain CDR3 selected from the group consisting of SEQ ID NOs: 6, 22, 38, 54, 72, 88, 100, 110, 125, 139, 158, 174, and 189.

For example, the antibodies of the invention comprise a light chain comprising SEQ ID NO: 4 for CDRL1, SEQ ID NO: 5 for CDRL2; SEQ ID NO: 6 for CDRL3; SEQ ID NO: 20 for CDRL1, SEQ ID NO: 21 for CDRL2; SEQ ID NO: 22 for CDRL3; SEQ ID NO: 36 for CDRL1, SEQ ID NO: 37 for CDRL2; SEQ ID NO: 38 for CDRL3; SEQ ID NO: 52 for CDRL1, SEQ ID NO: 53 for CDRL2; SEQ ID NO: 54 for CDRL3; SEQ ID NO: 70 for CDRL1, SEQ ID NO: 71 for CDRL2; SEQ ID NO: 72 for CDRL3; SEQ ID NO: 86 for CDRL1, SEQ ID NO: 87 for CDRL2; SEQ ID NO: 88 for CDRL3; SEQ ID NO: 99 for CDRL1, SEQ ID NO: 53 for CDRL2; SEQ ID NO: 100 for CDRL3; SEQ ID NO: 108 for CDRL1, SEQ ID NO: 109 for CDRL2; SEQ ID NO: 110 for CDRL3; SEQ ID NO: 70 for CDRL1, SEQ ID NO: 124 for CDRL2; SEQ ID NO: 125 for CDRL3; SEQ ID NO: 138 for CDRL1, SEQ ID NO: 109 for CDRL2; SEQ ID NO: 139 for CDRL3; SEQ ID NO: 156 for CDRL1, SEQ ID NO: 157 for CDRL2; SEQ ID NO: 158 for CDRL3; SEQ ID NO: 172 for CDRL1, SEQ ID NO: 173 for CDRL2; SEQ ID NO: 174 for CDRL3; and SEQ ID NO: 188 for CDRL1, SEQ ID NO: 37 for CDRL2; SEQ ID NO: 189 for CDRL3.

In one embodiment, an antibody of the invention, or antigen binding fragment thereof, comprises all of the CDRs of antibody HMB-DV-1 as listed in Table 1, and neutralizes dengue virus infection in a human host. In another embodiment, an antibody of the invention, or antigen binding fragment thereof, comprises all of the CDRs of antibody HMB-DV-2 as listed in Table 1, and neutralizes dengue virus infection in a human host. In another embodiment, an antibody of the invention, or antigen binding fragment thereof, comprises all of the CDRs of antibody HMB-DV-3 as listed in Table 1, and neutralizes dengue virus infection in a human host. In yet another embodiment, an antibody of the invention, or antigen binding fragment thereof, comprises all of the CDRs of antibody HMB-DV-4 as listed in Table 1, and neutralizes dengue virus infection in a human host. In yet another embodiment, an antibody of the invention, or antigen binding fragment thereof, comprises all of the CDRs of antibody HMB-DV-5 as listed in Table 1, and neutralizes dengue virus infection in a human host. In yet another embodiment, an antibody of the invention, or antigen binding fragment thereof, comprises all of the CDRs of antibody HMB-DV-6 as listed in Table 1, and neutralizes dengue virus infection in a human host. In yet another embodiment, an antibody of the invention, or antigen binding fragment thereof, comprises all of the CDRs of antibody HMB-DV-7 as listed in Table 1, and neutralizes dengue virus infection in a human host.

In a further embodiment, an antibody of the invention, or antigen binding fragment thereof, comprises all of the CDRs of antibody HMB-DV-8 as listed in Table 1, and neutralizes dengue virus infection in a human host. In another embodiment, an antibody of the invention, or antigen binding fragment thereof, comprises all of the CDRs of antibody HMB-DV-9 as listed in Table 1, and neutralizes dengue virus infection in a human host. In still another embodiment, an antibody of the invention, or antigen binding fragment thereof, comprises all of the CDRs of antibody HMB-DV-10 as listed in Table 1, and neutralizes dengue virus infection in a human host. In yet another embodiment, an antibody of the invention, or antigen binding fragment thereof, comprises all of the CDRs of antibody HMB-DV-11 as listed in Table 1, and neutralizes dengue virus infection in a human host. In yet another embodiment, an antibody of the invention, or antigen binding fragment thereof, comprises all of the CDRs of antibody HMB-DV-12 as listed in Table 1, and neutralizes dengue virus infection in a human host. In yet another embodiment, an antibody of the invention, or antigen binding fragment thereof, comprises all of the CDRs of antibody HMB-DV-13 as listed in Table 1, and neutralizes dengue virus infection in a human host. In yet another embodiment, an antibody of the invention, or antigen binding fragment thereof, comprises all of the CDRs of antibody HMB-DV-14 as listed in Table 1, and neutralizes dengue virus infection in a human host.

In still another embodiment, the antibodies of the invention comprise a heavy chain with an amino acid sequence that is at least 70%, at least 75%, at least 80%, at least 85%, at least 90%, at least 95%, at least 98%, or at least 99% identical to those of SEQ ID NOs: 13, 29, 45, 61, 65, 79, 95, 117, 131, 145, 151, 165, 181, or 195. In yet another embodiment, the antibodies of the invention comprise a light chain with an amino acid sequence that is at least 70%, at least 75%, at least 80%, at least 85%, at least 90%, at least 95%, at least 98%, or at least 99% identical to those of SEQ ID NOs: 14, 30, 46, 62, 80, 96, 103, 118, 132, 146, 166, 182, or 196.

In a further embodiment, the antibodies, antibody variants or antibody fragments of the invention comprise a heavy chain variable region comprising the amino acid sequence of any one of SEQ ID NOs: 13, 29, 45, 61, 65, 79, 95, 117, 131, 145, 151, 165, 181, or 195, and a light chain variable region comprising the amino acid sequence of any one of SEQ ID NOs: 14, 30, 46, 62, 80, 96, 103, 118, 132, 146, 166, 182, or 196.

In yet another embodiment, the antibodies, antibody variants or antibody fragments of the invention neutralize dengue virus infection and comprise a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 45 and a light chain variable region comprising the amino acid sequence of SEQ ID NO: 46; or a heavy chain variable region comprising the amino acid sequence of SEQ ID NO: 61 and a light chain variable region comprising the amino acid sequence of SEQ ID NO: 62; or a heavy chain variable region comprising the amino acid sequence of SEQ ID NO: 65 and a light chain variable region comprising the amino acid sequence of SEQ ID NO: 62; or a heavy chain variable region comprising the amino acid sequence of SEQ ID NO: 79 and a light chain variable region comprising the amino acid sequence of SEQ ID NO: 80; or a heavy chain variable region comprising the amino acid sequence of SEQ ID NO: 95 and a light chain variable region comprising the amino acid sequence of SEQ ID NO: 96; or a heavy chain variable region comprising the amino acid sequence of SEQ ID NO: 95 and a light chain variable region comprising the amino acid sequence of SEQ ID NO: 103; or a heavy chain variable region comprising the amino acid sequence of SEQ ID NO: 117 and a light chain variable region comprising the amino acid sequence of SEQ ID NO: 118; or a heavy chain variable region comprising the amino acid sequence of SEQ ID NO: 131 and a light chain variable region comprising the amino acid sequence of SEQ ID NO: 132; or a heavy chain variable region comprising the amino acid sequence of SEQ ID NO: 145 and a light chain variable region comprising the amino acid sequence of SEQ ID NO: 146; or a heavy chain variable region comprising the amino acid sequence of SEQ ID NO: 151 and a light chain variable region comprising the amino acid sequence of SEQ ID NO: 146; or a heavy chain variable region comprising the amino acid sequence of SEQ ID NO: 165 and a light chain variable region comprising the amino acid sequence of SEQ ID NO: 166; or a heavy chain variable region comprising the amino acid sequence of SEQ ID NO: 181 and a light chain variable region comprising the amino acid sequence of SEQ ID NO: 182; or a heavy chain variable region comprising the amino acid sequence of SEQ ID NO: 195 and a light chain variable region comprising the amino acid sequence of SEQ ID NO: 196.

Methods for chain replacement and for CDR grafting are well known in the art. Originally these methods were developed to humanize non-human antibodies (generally mouse antibodies) or to select human antibody counterparts having equivalent bioactivity to the non-human antibodies. These methods include replacement techniques where only one of the CDRs, for example, the CDR3s, of the non-human antibody are retained and the remainder of the V-region, including the framework and the other two CDRs, for example, the CDRs 1 and 2, are individually replaced in steps performed sequentially (e.g. U.S. Patent Application No. 20030166871; Rader, et al., *Proc Natl Acad Sci USA* 95:8910-15, 1998; Steinberg, et al., *J Biol Chem* 275:36073-78, 2000; Rader, et al., *J Biol Chem* 275:13668-76, 2000).

In addition, methods of creating antibodies with the binding specificities of a reference antibody for a target antigen are described in Patent Application No. WO05/069,970. The methods include transferring, from the reference antibody to a recipient antibody or antibody fragment, the minimal essential binding specificity of the reference antibody. Examples of regions that can be transferred include, but are not limited to, the transfer of a single CDR segment, for example a CDR3 segment, from the heavy and/or from the light chain, or a D segment, or a CDR3-FR4 segment, or any CDR3-FR4 segment that comprises the minimal essential binding specificity determinant. Antibodies created using these methods retain the binding specificity, and often affinity, of the reference antibody.

The antibodies, antibody variants or antibody fragments of the invention include antibodies that comprise, inter alia, one or more CDRs, a heavy chain or a light chain of an exemplary antibody of the invention and retain their specificity and ability to neutralize dengue virus infection.

Exemplary antibodies of the invention include, but are not limited to, HMB-DV1, HMB-DV2, HMB-DV3, HMB-DV4, HMB-DV5, HMB-DV6, HMB-DV7, HMB-DV8, HMB-DV9, HMB-DV10, HMB-DV11, HMB-DV12, HMB-DV13, and HMB-DV14.

Variants of HMB-DV4 consist of a heavy chain variants having amino acid sequence recited in SEQ ID NO: 61 and SEQ ID NO: 65, and a light chain having the amino acid sequence recited in SEQ ID NO: 62. The nucleic acid sequences encoding the heavy chain variants are recited in SEQ ID NO: 63 and SEQ ID NO: 66. The nucleic acid encoding the light chain is recited in SEQ ID NO: 64. Thus, antibodies comprising the HMB-DV4 variant heavy chains (SEQ ID NOs: 61, 65) and light chain (SEQ ID NO: 62) are included within the scope of the invention.

As used herein, the term "HMB-DV4" is used to refer to any and/or all variants of HMB-DV4, for example, those with heavy chains corresponding to SEQ ID NOs: 61 and 65 and light chain corresponding to SEQ ID NO: 62.

In one embodiment, an antibody cocktail of the invention comprises two or more antibodies selected from the group consisting of HMB-DV1, HMB-DV2, HMB-DV3, HMB-DV4, HMB-DV5, HMB-DV6, HMB-DV7, HMB-DV8, HMB-DV9, HMB-DV10, HMB-DV11, HMB-DV12, HMB-DV13, and HMB-DV14. In another embodiment, a cocktail of the invention comprises three antibodies selected from the group consisting of HMB-DV1, HMB-DV2, HMB-DV3, HMB-DV4, HMB-DV5, HMB-DV6, HMB-DV7, HMB-DV8, HMB-DV9, HMB-DV10, HMB-DV11, HMB-DV12, HMB-DV13, and HMB-DV14. In yet another embodiment, an antibody cocktail of the invention comprises more than three, for example, 4, 5, 6, 7, or 8 antibodies selected from the group consisting of HMB-DV1, HMB-DV2, HMB-DV3, HMB-DV4, HMB-DV5, HMB-DV6, HMB-DV7, HMB-DV8, HMB-DV9, HMB-DV10, HMB-DV11, HMB-DV12, HMB-DV13, and HMB-DV14. In an exemplary embodiment, a cocktail of the invention comprises HMB-DV5, HMB-DV6, and HMB-DV8.

The invention further comprises an antibody, or fragment thereof, that binds to an epitope capable of binding to an antibody of the invention. The invention also comprises an antibody or an antibody fragment that competes with an antibody of the invention.

In another aspect, the invention also includes nucleic acid sequences encoding part or all of the light and heavy chains and CDRs of the antibodies of the present invention. In one embodiment, nucleic acid sequences according to the invention include nucleic acid sequences having at least 70%, at least 75%, at least 80%, at least 85%, at least 90%, at least 95%, at least 98%, or at least 99% identity to the nucleic acid encoding a heavy or light chain of an antibody of the invention. In another embodiment, a nucleic acid sequence of the invention has the sequence of a nucleic acid encoding a heavy or light chain CDR of an antibody of the invention. For example, a nucleic acid sequence according to the invention comprises a sequence that is at least 70%, at least 75%, at least 80%, at least 85%, at least 90%, at least 95%, at least 98%, or at least 99% identical to the nucleic acid sequences of SEQ ID NOs: 7-12, 23-28, 39-44, 55-60, 73-78, 89-94, 101, 102, 111-116, 126-128, 129, 130, 140-144, 150, 159-164, 175-180, and 190-194.

Due to the redundancy of the genetic code, variants of these sequences will exist that encode the same amino acid sequences. These variants are included within the scope of the invention.

Variant antibodies are also included within the scope of the invention. Thus, variants of the sequences recited in the application are also included within the scope of the invention. Such variants include natural variants generated by somatic mutation in vivo during the immune response or in vitro upon culture of immortalized B cell clones. Alternatively, variants may arise due to the degeneracy of the genetic code, as mentioned above or may be produced due to errors in transcription or translation. Variants may also be introduced to modify the antibody effector function, for instance in the Fc region to reduce the binding of the antibody to an Fc receptor.

Further variants of the antibody sequences having improved affinity and/or potency may be obtained using methods known in the art and are included within the scope of the invention. For example, amino acid substitutions may be used to obtain antibodies with further improved affinity. Alternatively, codon optimisation of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

In one embodiment variant antibody sequences may share 70% or more (i.e. 75%, 80%, 85%, 90%, 95%, 97%, 98%, 99% or more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm nih.gov/) [Blosum 62 matrix; gap open penalty=11 and gap extension penalty=1].

Further included within the scope of the invention are vectors, for example expression vectors, comprising a nucleic acid sequence according to the invention. Cells transformed with such vectors are also included within the scope of the invention. Examples of such cells include but are not limited to, eukaryotic cells, e.g. yeast cells, animal cells or plant cells. In one embodiment the cells are mammalian, e.g. human, CHO, HEK293T, PER.C6, NS0, myeloma or hybridoma cells.

The invention also relates to monoclonal antibodies that bind to an epitope capable of binding an antibody of the invention. In one embodiment, the invention includes a monoclonal antibody that binds to an epitope capable of binding a monoclonal antibody selected from the group consisting of HMB-DV1, HMB-DV2, HMB-DV3, HMB-DV4, HMB-DV5, HMB-DV6, HMB-DV7, HMB-DV8, HMB-DV9, HMB-DV10, HMB-DV11, HMB-DV12, HMB-DV13, and HMB-DV14.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme. The antibodies may also be used for the molecular identification and characterisation (epitope mapping) of antigens.

Antibodies of the invention will typically be glycosylated. N-linked glycans attached to the $C_H2$ domain of a heavy chain, for instance, can influence C1q and FcR binding, with aglycosylated antibodies having lower affinity for these receptors. The glycan structure can also affect activity e.g. differences in complement-mediated cell death may be seen depending on the number of galactose sugars (0, 1 or 2) at the terminus of a glycan's biantennary chain. An antibody's glycans preferably do not lead to a human immunogenic response after administration.

Antibodies of the invention can be coupled to a drug for delivery to a treatment site or coupled to a detectable label to facilitate imaging of a site comprising cells of interest, such as cells infected with dengue virus. Methods for coupling antibodies to drugs and detectable labels are well known in the art, as are methods for imaging using detectable labels. Labelled antibodies may be employed in a wide variety of assays, employing a wide variety of labels. Detection of the formation of an antibody-antigen complex between an antibody of the invention and an epitope of interest (a DENV epitope) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}I$, $^{131}I$, $^{35}S$, or $^3H$. Such labeled reagents may be used in a variety of well-known assays, such as radioimmunoassays, enzyme immunoassays, e.g., ELISA, fluorescent immunoassays, and the like.

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, calicheamicin bacterial toxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-256; ed. Hellstrom et al. (1987) "Antibodies for Drug Delivery," in *Controlled Drug Delivery*, ed. Robinson et al. (2d ed; Marcel Dekker, Inc.), pp. 623-653; Thorpe (1985) "Antibody Carriers of Cytotoxic Agents in Cancer Therapy: A Review," in *Monoclonal Antibodies '84: Biological and Clinical Applications*, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in *Monoclonal Antibodies for Cancer Detection and Therapy*, ed. Baldwin et al. (Academic Press, New York, 1985), pp. 303-316; and Thorpe et al. (1982) *Immunol. Rev.* 62:119-158.

Alternatively, an antibody can be conjugated to a second antibody to form an antibody heteroconjugate as described in reference 4. In addition, linkers may be used between the labels and the antibodies of the invention [5]. Antibodies or, antigen-binding fragments thereof may be directly labelled with radioactive iodine, indium, yttrium, or other radioactive particle known in the art [6]. Treatment may consist of a combination of treatment with conjugated and non-conjugated antibodies administered simultaneously or subsequently [7, 8].

Antibodies of the invention may also be attached to a solid support.

Additionally, antibodies of the invention, or functional antibody fragments thereof, can be chemically modified by covalent conjugation to a polymer to, for example, increase their circulating half-life, for example. Examples of polymers, and methods to attach them to peptides, are shown in references 9-12. In some embodiments the polymers may be selected from polyoxyethylated polyols and polyethylene glycol (PEG). PEG is soluble in water at room temperature and has the general formula: R(O—CH$_2$—CH$_2$)$_n$O—R where R can be hydrogen, or a protective group such as an alkyl or alkanol group. In one embodiment the protective group may have between 1 and 8 carbons. In a further embodiment the protective group is methyl. The symbol n is a positive integer. In one embodiment n is between 1 and 1,000. In another embodiment n is between 2 and 500. In one embodiment the PEG has an average molecular weight between 1,000 and 40,000. In a further embodiment the PEG has a molecular weight between 2,000 and 20,000. In yet a further embodiment the PEG has a molecular weight of between 3,000 and 12,000. In one embodiment PEG has at least one hydroxy group. In another embodiment the PEG has a terminal hydroxy group. In yet another embodiment it is the terminal hydroxy group which is activated to react with a free amino group on the inhibitor. However, it will be understood that the type and amount of the reactive groups may be varied to achieve a covalently conjugated PEG/antibody of the present invention.

Antibodies of the invention can be modified by introducing random amino acid mutations into particular region of the CH2 or CH3 domain of the heavy chain in order to alter their binding affinity for FcRn and/or their serum half-life in comparison to the unmodified antibodies. Examples of such modifications include, but are not limited to, substitutions of at least one amino acid from the heavy chain constant region selected from the group consisting of amino acid residues 250, 314, and 428.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. In some embodiments POG has a molecular weight in the same range as PEG The structure for POG is shown in reference 13, and a discussion of POG/IL-2 conjugates is found in reference 9.

Another drug delivery system that can be used for increasing circulatory half-life is the liposome. Methods of preparing liposome delivery systems are discussed in references 14, 15 and 16. Other drug delivery systems are known in the art and are described in, for example, references 17 and 18.

Antibodies of the invention may be provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention may be immunogenic in non-human (or heterologous) hosts e.g. in mice. In particular, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanisation or from xeno-mice.

Antibodies of the invention can be of any isotype (e.g. IgA, IgG, IgM i.e. an α, γ or μ heavy chain), but will generally be IgG. Within the IgG isotype, antibodies may be IgG1, IgG2, IgG3 or IgG4 subclass. In one embodiment, the antibody is IgG1. Antibodies of the invention may have a κ or λ light chain.

Included within the scope of the invention are DENV-neutralizing recombinant or engineered bispecific antibody molecules or antigen binding fragments thereof. Such antibodies and fragments may comprise a first binding site for an epitope on a first Dengue virus serotype and a second binding site for a second epitope on the same dengue virus serotype or on a different, for example, a second, third or fourth, dengue virus serotype. The variable domains of the respective binding sites can be formed as immunoglobulin isotypes of the invention or as heterodimeric Fab, Fab', F(ab')$_2$, ScFv or diabodies that can be linked together via one or more peptide linkers.

Production of Antibodies

Monoclonal antibodies according to the invention can be made by any method known in the art. The general methodology for making monoclonal antibodies using hybridoma technology is well known [19, 20]. Preferably, the alternative EBV immortalisation method described in reference 21 is used.

Using the method described in reference 21, B cells producing the antibody of the invention can be transformed with EBV in the presence of a polyclonal B cell activator. Transformation with EBV is a standard technique and can easily be adapted to include polyclonal B cell activators.

Additional stimulants of cellular growth and differentiation may optionally be added during the transformation step to further enhance the efficiency. These stimulants may be cytokines such as IL-2 and IL-15. In one aspect, IL-2 is added during the immortalisation step to further improve the efficiency of immortalisation, but its use is not essential.

The immortalised B cells produced using these methods can then be cultured using methods known in the art and antibodies isolated therefrom.

The antibodies of the invention can also be made by culturing single plasma cells in microwell culture plates using the method described in UK Patent Application 0819376.5. Further, from single plasma cell cultures, RNA can be extracted and single cell PCR can be performed using methods known in the art. The VH and VL regions of the antibodies can be amplified by RT-PCR, sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

Monoclonal antibodies may be further purified, if desired, using filtration, centrifugation and various chromatographic methods such as HPLC or affinity chromatography. Techniques for purification of monoclonal antibodies, including techniques for producing pharmaceutical-grade antibodies, are well known in the art.

Fragments of the monoclonal antibodies of the invention can be obtained from the monoclonal antibodies by methods that include digestion with enzymes, such as pepsin or papain, and/or by cleavage of disulfide bonds by chemical reduction. Alternatively, fragments of the monoclonal antibodies can be obtained by cloning and expression of part of the sequences of the heavy or light chains. Antibody "fragments" may include Fab, Fab', F(ab)$_2$ and Fv fragments. The invention also encompasses single-chain Fv fragments (scFv) derived from the heavy and light chains of a monoclonal antibody of the invention e.g. the invention includes a scFv comprising the CDRs from an antibody of the invention. Also included are heavy or light chain monomers and dimers as well as single chain antibodies, e.g. single chain Fv in which the heavy and light chain variable domains are joined by a peptide linker.

Standard techniques of molecular biology may be used to prepare DNA sequences coding for the antibodies or fragments or variants of the antibodies of the present invention. Desired DNA sequences may be synthesised completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, HEK293T, PER.C6, NS0, myeloma or hybridoma cells.

The present invention also provides a process for the production of an antibody of the invention comprising culturing a host cell comprising a vector of the present invention under conditions suitable for leading to expression of protein from DNA encoding the antibody of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a cell, and ii) isolating the expressed antibody product. Additionally, the method may include iii) purifying the antibody.

Screening and Isolation of B Cells

Transformed B cells may be screened for those producing antibodies of the desired antigen specificity, and individual B cell clones may then be produced from the positive cells.

The screening step may be carried out by ELISA, by staining of tissues or cells (including infected or transfected cells), a neutralisation assay or one of a number of other methods known in the art for identifying desired antigen specificity. The assay may select on the basis of simple antigen recognition, or may select on the additional basis of a desired function e.g. to select neutralizing antibodies rather than just antigen-binding antibodies, to select antibodies that can change characteristics of targeted cells, such as their signalling cascades, their shape, their growth rate, their capability of influencing other cells, their response to the influence by other cells or by other reagents or by a change in conditions, their differentiation status, etc.

The cloning step for separating individual clones from the mixture of positive cells may be carried out using limiting dilution, micromanipulation, single cell deposition by cell sorting or another method known in the art.

The immortalised B cell clones of the invention can be used in various ways e.g. as a source of monoclonal antibodies, as a source of nucleic acid (DNA or mRNA) encoding a monoclonal antibody of interest, for research, etc.

The invention provides a composition comprising immortalised B memory cells, wherein the cells produce antibodies that neutralize one or more dengue virus serotypes, and wherein the antibodies are produced at ≥5 pg per cell per day. The invention also provides a composition comprising clones of an immortalised B memory cell, wherein the clones produce a monoclonal antibody that neutralizes one or more dengue virus serotypes, and wherein the antibody is produced at ≥5 pg per cell per day.

Exemplary immortalised B cell clone according to the invention include, but are not limited to, HMB-DV1, HMB-DV2, HMB-DV3, HMB-DV4, HMB-DV5, HMB-DV6, HMB-DV7, HMB-DV8, HMB-DV9, HMB-DV10, HMB-DV11, HMB-DV12, HMB-DV13, and HMB-DV14.

Epitopes

As mentioned above, the antibodies of the invention can be used to map the epitopes to which they bind. The epitopes recognised by the antibodies of the present invention may have a number of uses. The epitope and mimotopes thereof in purified or synthetic form can be used to raise immune responses (i.e. as a vaccine, or for the production of antibodies for other uses) or for screening patient serum for antibodies that immunoreact with the epitope or mimotopes thereof. In one embodiment such an epitope or mimotope, or antigen comprising such an epitope or mimotope may be used as a vaccine for raising an immune response. The antibodies and antigen binding fragments of the invention can also be used in a method of monitoring the quality of vaccines. In particular the antibodies can be used to check that the antigen in a vaccine contains the specific epitope in the correct conformation.

The epitope may also be useful in screening for ligands that bind to said epitope. Such ligands, include but are not limited to antibodies, including those from camels, sharks and other species, fragments of antibodies, peptides, phage display technology products, aptamers, adnectins, synthetic compounds, or fragments of other viral or cellular proteins, that may block the epitope and so prevent infection. Such ligands are encompassed within the scope of the invention.

Recombinant Expression

The immortalised B memory cells of the invention may also be used as a source of nucleic acid for the cloning of antibody genes for subsequent recombinant expression. Expression from recombinant sources is more common for pharmaceutical purposes than expression from B cells or hybridomas e.g. for reasons of stability, reproducibility, culture ease, etc.

Thus the invention provides a method for preparing a recombinant cell, comprising the steps of: (i) obtaining one or more nucleic acids (e.g. heavy and/or light chain genes) from the B cell clone that encodes the antibody of interest; and (ii) inserting the nucleic acid into an expression host in order to permit expression of the antibody of interest in that host.

Similarly, the invention provides a method for preparing a recombinant cell, comprising the steps of: (i) sequencing nucleic acid(s) from the B cell clone that encodes the antibody of interest; and (ii) using the sequence information from step (i) to prepare nucleic acid(s) for insertion into an expression host in order to permit expression of the antibody of interest in that host. The nucleic acid may, but need not, be manipulated between steps (i) and (ii) to introduce restriction sites, to change codon usage, to optimise transcription and/or translation regulatory sequences, and/or to modify effector function.

The invention also provides a method of preparing a recombinant cell, comprising the step of transforming a host cell with one or more nucleic acids that encode a monoclonal antibody of interest, wherein the nucleic acids are nucleic acids that were derived from an immortalised B cell clone of the invention. Thus the procedures for first preparing the nucleic acid(s) and then using it to transform a host cell can be performed at different times by different people in different places (e.g., in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture techniques can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells are well known in the art (e.g., see reference 22).

The expression host is preferably a eukaryotic cell, including yeast and animal cells, particularly mammalian cells (e.g. CHO cells, NS0 cells, human cells such as PER.C6 [Crucell; reference 23] or HKB-11 [Bayer; references 24 & 25] cells, myeloma cells [26 & 27], etc.), as well as plant cells. Preferred expression hosts can glycosylate the antibody of the invention, particularly with carbohydrate structures that are not themselves immunogenic in humans. In one embodiment the expression host may be able to grow in serum-free media. In a further embodiment the expression host may be able to grow in culture without the presence of animal-derived products.

The expression host may be cultured to give a cell line.

The invention provides a method for preparing one or more nucleic acid molecules (e.g. heavy and light chain genes) that encode an antibody of interest, comprising the steps of: (i) preparing an immortalised B cell clone according to the invention; (ii) obtaining from the B cell clone nucleic acid that encodes the antibody of interest. The invention also provides a method for obtaining a nucleic acid sequence that encodes an antibody of interest, comprising the steps of: (i) preparing an immortalised B cell clone according to the invention; (ii) sequencing nucleic acid from the B cell clone that encodes the antibody of interest.

The invention also provides a method of preparing nucleic acid molecule(s) that encodes an antibody of interest, comprising the step of obtaining the nucleic acid from a B cell clone that was obtained from a transformed B cell of the invention. Thus the procedures for first obtaining the B cell clone and then preparing nucleic acid(s) from it can be performed at very different times by different people in different places (e.g. in different countries).

The invention provides a method for preparing an antibody (e.g. for pharmaceutical use), comprising the steps of: (i) obtaining and/or sequencing one or more nucleic acids (e.g. heavy and light chain genes); (ii) using the sequence information from step (i) to prepare nucleic acid(s) for insertion into an expression host in order to permit expression of the antibody of interest in that host; (iii) culturing or sub-culturing the expression host under conditions where the antibody of interest is expressed; and, optionally, (iv) purifying the antibody of the interest. The nucleic acid can, but need not be, obtained and/or sequenced from a B cell clone expressing the antibody of interest. In one embodiment, the nucleic acid from step (i) may, optionally be modified so as to introduce desired substitutions in the amino acid sequence of the antibody.

The invention also provides a method of preparing an antibody comprising the steps of: culturing or sub-culturing an expression host cell population under conditions where the antibody of interest is expressed and, optionally, purifying the antibody of the interest, wherein said expression host cell population has been prepared by (i) providing nucleic acid(s) encoding an antibody of interest; (ii) inserting the nucleic acid(s) into an expression host that can express the antibody of interest, and (iii) culturing or sub-culturing expression hosts comprising said inserted nucleic acids to produce said expression host cell population.

Pharmaceutical Compositions

The invention provides a pharmaceutical composition containing the antibodies and/or antibody fragments of the invention and/or nucleic acid encoding such antibodies and/or immortalised B cells that express such antibodies and/or the epitopes recognised by the antibodies of the invention. A pharmaceutical composition may also contain a pharmaceutically acceptable carrier to allow administration. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Within the scope of the invention, forms of administration may include those forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. In one embodiment the compositions are adapted for administration to human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. Dosage treatment may be a single dose schedule or a multiple dose schedule. Known antibody-based pharmaceuticals provide guidance relating to frequency of administration e.g. whether a pharmaceutical should be delivered daily, weekly, monthly, etc. Frequency and dosage may also depend on the severity of symptoms.

Compositions of the invention may be prepared in various forms. For example, the compositions may be prepared as injectables, either as liquid solutions or suspensions. Solid forms suitable for solution, or suspension, in liquid vehicles prior to injection can also be prepared (e.g. a lyophilised composition, like Synagis™ and Herceptin™, for reconstitution with sterile water containing a preservative). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. For example, a lyophilised antibody can be provided in kit form with sterile water or a sterile buffer.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Gennaro (2000) *Remington: The Science and Practice of Pharmacy*, 20th edition, ISBN: 0683306472.

Pharmaceutical compositions of the invention generally have a pH between 5.5 and 8.5, in some embodiments this may be between 6 and 8, and in further embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Pharmaceutical compositions will include a therapeutically effective amount of one or more antibodies of the invention and/or a polypeptide comprising an epitope that binds an antibody of the invention i.e. an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g., Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc.

In one embodiment pharmaceutical compositions can include more than one (e.g. 2, 3, 4, 5, 6, 7, 8, etc.) antibody of the invention. In another embodiment the composition comprises two or more (e.g. 2, 3, 4, 5, etc.) antibodies, wherein the first antibody is specific for a first DENV epitope, and the second antibody is specific for a second DENV epitope. In yet another embodiment, the pharmaceutical composition comprises three antibodies of the invention. In another embodiment, the composition comprises two or more (e.g. 2, 3, 4, 5, etc.) antibodies, that together neutralise more than one dengue virus serotype. In yet another embodiment, the two or more antibodies of the invention together neutralise all four dengue virus serotypes, DENV-1, DENV-2, DENV-3 and DENV-4. In a further embodiment two or more antibodies of the invention together neutralise all four dengue virus serotypes by binding at least two distinct epitopes on each dengue virus serotype.

Exemplary antibodies of the invention for use in a pharmaceutical composition that neutralize a dengue virus without contributing to antibody-dependent enhancement of dengue virus infection include, but are not limited to, HMB-DV1, HMB-DV2, HMB-DV3, HMB-DV4, HMB-DV5, HMB-DV6, HMB-DV7, HMB-DV8, HMB-DV9, HMB-DV10, HMB-DV11, HMB-DV12, HMB-DV13, and HMB-DV14.

In one embodiment, a pharmaceutical composition includes two exemplary antibodies of the invention, for example, HMB-DV3 and HMB-DV7; HMB-DV3 and HMB-DV9; HMB-DV3 and HMB-DV12; HMB-DV3 and HMB-DV14; HMB-DV6 and HMB-DV7; HMB-DV6 and HMB-DV8. In another embodiment, a pharmaceutical composition includes three exemplary antibodies of the invention, for example, HMB-DV2, HMB-DV3 and HMB-DV6; HMB-DV2, HMB-DV6 and HMB-DV8; HMB-DV2, HMB-DV8 and HMB-DV9; HMB-DV2, HMB-DV8 and HMB-DV12; HMB-DV2, HMB-DV8 and HMB-DV14; HMB-DV5, HMB-DV6 and HMB-DV8. Based on the teachings herein, one of skill in the art can determine other combinations of antibodies for use in a pharmaceutical composition.

In one embodiment, the invention provides a pharmaceutical composition comprising the antibody HMB-DV1 or an antigen binding fragment thereof, and a pharmaceutically acceptable diluent or carrier. In another embodiment, the invention provides a pharmaceutical composition comprising the antibody HMB-DV2 or an antigen binding fragment thereof, and a pharmaceutically acceptable diluent or carrier. In another embodiment, the invention provides a pharmaceutical composition comprising the antibody HMB-DV3 or an antigen binding fragment thereof, and a pharmaceutically acceptable diluent or carrier. In another embodiment, the invention provides a pharmaceutical composition comprising the antibody HMB-DV4 or an antigen binding fragment thereof, and a pharmaceutically acceptable diluent or carrier. In yet another embodiment, the invention provides a pharmaceutical composition comprising the antibody HMB-DV5 or an antigen binding fragment thereof, and a pharmaceutically acceptable diluent or carrier. In another embodiment, the invention provides a pharmaceutical composition comprising the antibody HMB-DV6 or an antigen binding fragment thereof, and a pharmaceutically acceptable diluent or carrier. In another embodiment, the invention provides a pharmaceutical composition comprising the antibody HMB-DV7 or an antigen binding fragment thereof, and a pharmaceutically acceptable diluent or carrier.

In yet another embodiment, the invention provides a pharmaceutical composition comprising the antibody HMB-DV8 or an antigen binding fragment thereof, and a pharmaceutically acceptable diluent or carrier. In another embodiment, the invention provides a pharmaceutical composition comprising the antibody HMB-DV9 or an antigen binding fragment thereof, and a pharmaceutically acceptable diluent or carrier. In another embodiment, the invention provides a pharmaceutical composition comprising the antibody HMB-DV10 or an antigen binding fragment thereof, and a pharmaceutically acceptable diluent or carrier. In yet another embodiment, the invention provides a pharmaceutical composition comprising the antibody HMB-DV11 or an antigen binding fragment thereof, and a pharmaceutically acceptable diluent or carrier. In another embodiment, the invention provides a pharmaceutical composition comprising the antibody HMB-DV12 or an antigen binding fragment thereof, and a pharmaceutically acceptable diluent or carrier. In another embodiment, the invention provides a pharmaceutical composition comprising the antibody HMB-DV13 or an antigen binding fragment thereof, and a pharmaceutically acceptable diluent or carrier. In yet another embodiment, the invention provides a pharmaceutical composition comprising the antibody HMB-DV14 or an antigen binding fragment thereof, and a pharmaceutically acceptable diluent or carrier.

Antibodies of the invention may be administered (either combined or separately) with other therapeutics e.g. with chemotherapeutic compounds, with radiotherapy, etc. Preferred therapeutic compounds include anti-viral compounds. Such combination therapy provides an additive or synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

In compositions of the invention that include antibodies of the invention, the antibodies may make up at least 50% by weight (e.g. 60%, 70%, 75%, 80%, 85%, 90%, 95%, 97%, 98%, 99% or more) of the total protein in the composition. The antibodies are thus in purified form.

The invention provides a method of preparing a pharmaceutical, comprising the steps of: (i) preparing an antibody of the invention; and (ii) admixing the purified antibody with one or more pharmaceutically-acceptable carriers.

The invention also provides a method of preparing a pharmaceutical, comprising the step of admixing an antibody with one or more pharmaceutically-acceptable carriers, wherein the antibody is a monoclonal antibody that was obtained from a transformed B cell of the invention. Thus the procedures for first obtaining the monoclonal antibody and then preparing the pharmaceutical can be performed at very different times by different people in different places (e.g. in different countries).

As an alternative to delivering antibodies for therapeutic purposes, it is possible to deliver nucleic acid (typically DNA) that encodes the monoclonal antibody (or active fragment thereof) of interest to a subject, such that the nucleic acid can be expressed in the subject in situ to provide a desired therapeutic effect. Suitable gene therapy and nucleic acid delivery vectors are known in the art.

Compositions of the invention may be immunogenic compositions, and in some embodiments may be vaccine compositions comprising an antigen comprising a DENV epitope. Vaccines according to the invention may either be prophylactic (i.e. to prevent infection) or therapeutic (i.e. to treat infection).

Compositions may include an antimicrobial, particularly if packaged in a multiple dose format. Compositions may comprise detergent e.g. a Tween (polysorbate), such as Tween 80. Detergents are generally present at low levels e.g. <0.01%. Compositions may include sodium salts (e.g. sodium chloride) to give tonicity. A concentration of 10±2 mg/ml NaCl is typical.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

The compositions of the invention may also comprise one or more immunoregulatory agents. In one embodiment, one or more of the immunoregulatory agents include(s) an adjuvant.

Medical Treatments and Uses

The antibodies, antigen binding fragments, derivatives and variants thereof, or the cocktails and pharmaceutical compositions of the invention can be used for the treatment of DENV infection, for the prevention of DENV infection or for the diagnosis of DENV infection.

Methods of diagnosis may include contacting an antibody or an antibody fragment with a sample. Such samples may be tissue samples taken from, for example, salivary glands, lung, liver, pancreas, kidney, ear, eye, placenta, alimentary tract, heart, ovaries, pituitary, adrenals, thyroid, brain or skin. The methods of diagnosis may also include the detection of an antigen/antibody complex.

The invention therefore provides (i) an antibody, an antibody fragment, or variants and derivatives thereof according to the invention, (ii) an immortalised B cell clone according to the invention, (iii) an epitope capable of binding an antibody of the invention or (iv) a ligand, preferably an antibody, capable of binding an epitope that binds an antibody of the invention for use in therapy.

Also provided is a method of treating a subject comprising administering to that subject (i) an antibody, an antibody fragment, variants and derivatives thereof, or a pharmaceutical composition according to the invention, or, a ligand, preferably an antibody, capable of binding an epitope that binds an antibody of the invention.

The invention also provides the use of (i) an antibody, an antibody fragment, or variants and derivatives thereof according to the invention, (ii) an immortalised B cell clone according to the invention, (iii) an epitope capable of binding an antibody of the invention, or (iv) a ligand, preferably an antibody, that binds to an epitope capable of binding an antibody of the invention, in the manufacture of a medicament for the prevention or treatment of DENV infection.

The invention provides a pharmaceutical composition for use as a medicament for the prevention or treatment of DENV infection. It also provides the use of an antibody of the invention and/or a protein comprising an epitope to which such an antibody binds in the manufacture of a medicament for treatment of a patient and/or diagnosis in a patient. It also provides a method for treating a subject, e.g., a human subject. The method comprises the step of administering to the subject a therapeutically effective dose of a composition of the invention. One way of checking efficacy of therapeutic treatment involves monitoring disease symptoms after administration of the composition of the invention. Treatment can be a single dose schedule or a multiple dose schedule.

In one embodiment, an antibody, antibody fragment, antibody variant, epitope or pharmaceutical composition according to the invention is administered to a subject in need of such treatment. Such a subject includes, but is not limited to, one who is particularly at risk of or susceptible to DENV infection.

Antibodies of the invention can be used in passive immunisation. Antibodies and fragments or variants thereof, or a nucleic acid encoding an antibody or an antibody fragment or variant as described in the present invention may also be used in a kit for the diagnosis of dengue virus infection.

Epitopes capable of binding an antibody of the invention, e.g., the monoclonal antibodies HMB-DV1, HMB-DV2, HMB-DV3, HMB-DV4, HMB-DV5, HMB-DV6, HMB-DV7, HMB-DV8, HMB-DV9, HMB-DV10, HMB-DV11, HMB-DV12, HMB-DV13, and HMB-DV14, may be used in a kit for monitoring the efficacy of vaccination procedures by detecting the presence of protective anti-DENV antibodies.

Antibodies, antibody fragments, or variants and derivatives thereof, as described in the present invention may also be used in a kit for monitoring vaccine manufacture with the desired immunogenicity.

The invention also provides a method of preparing a pharmaceutical composition, comprising the step of admixing a monoclonal antibody with one or more pharmaceutically-acceptable carriers, wherein the monoclonal antibody is a monoclonal antibody that was obtained from an expression host of the invention. Thus the procedures for first obtaining the monoclonal antibody (e.g. expressing it and/or purifying it) and then admixing it with the pharmaceutical carrier(s) can be performed at very different times by different people in different places (e.g. in different countries).

Starting with a transformed B cell of the invention, various steps of culturing, sub-culturing, cloning, sub-cloning, sequencing, nucleic acid preparation etc. can be performed in order to perpetuate the antibody expressed by the transformed B cell, with optional optimisation at each step. In a preferred embodiment, the above methods further comprise techniques of optimisation (e.g. affinity maturation or optimisation) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or amend certain nucleic acid sequences. Changes from such manipulation include, but are not limited to, changes to introduce restriction sites, to amend codon usage, to add or optimise transcription and/or translation regulatory sequences, etc. It is also possible to change the nucleic acid to alter the encoded amino acids. For example, it may be useful to introduce one or more (e.g. 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g. labels) or can introduce tags (e.g. for purification purposes). Mutations can be introduced in specific sites or can be introduced at random, followed by selection (e.g. molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Moreover, changes achieved in independent steps may be combined. Different properties introduced into the encoded amino acids may include, but are not limited to, enhanced affinity.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a patient is intended to include prevention and prophylaxis as well as therapy. The term "patient" means all mammals including humans. Generally, the patient is a human.

EXAMPLES

Exemplary embodiments of the present invention are provided in the following examples. The following examples are presented only by way of illustration and to assist one of ordinary skill in using the invention. The examples are not intended in any way to limit the scope of the invention.

Example 1

Cloning of B Cells and Screening for Identification of Dengue Virus Specific Abs Memory B cells were isolated from the blood of DENV immune donors and immortalized using EBV and CpG as described in reference. Briefly, IgG$^+$ memory B cells were isolated using CD22 beads, followed by removal of IgM$^+$, IgD$^+$ IgA$^+$ B cells using specific antibodies and cell sorting. The sorted cells (IgG$^+$) were immortalized with EBV in the presence of CpG 2006 and irradiated allogeneic mononuclear cells. Replicate cultures each containing 30-50 memory B cells were set up in several 96 well U-bottom plates. After two weeks the culture supernatants were collected and tested for their capacity to stain C6/36 cells infected with DENV of serotypes 1, 2, 3 or 4 by immunofluorescence analysis and/or to bind to recombinant DENV1-4 E2 proteins by ELISA. Supernatants were tested for their capacity to neutralize DENV infection of either VERO cells or DC-SIGN-transfected Raji cells and to enhance infection of K562 cells. B cell clones were isolated from positive polyclonal cultures as described previously [28]. IgG concentrations in the supernatants of selected clones were determined using an IgG-specific ELISA.

Example 2

Human mAbs from Immortalized B Cells Recognize Dengue Virus Proteins and Neutralize Infection For the viral neutralization and viral enhancement assay, titrated amounts of attenuated DENV of serotypes 1, 2, 3 or 4 were mixed with an equal volume of culture supernatants. Viruses and multiplicity of infection (MOI) used were: rDEN1Δ30 (03JB186-1A+V2) MOI 0.04; rDEN2/4Δ30 (04JBV351-1A-V2) MOI 0.04; rDEN3/4Δ30 (DEN3#107C) MOI 0.02; rDEN4Δ30 (06JBV591-V3+1A1+v2) MOI 0.04. After 1-hour incubation at room temperature the mixture was added to target cells (e.g. VERO cells, DC-SIGN-Raji cells or K562 cells) in 96 well flat bottom plates and incubated at 37° C. for 72-96 hours. The cells were then stained with a mouse monoclonal antibody to Dengue virus 1-4 E proteins (clone 4G2), followed by a fluorescein-labeled goat anti mouse Ig and analyzed by FACS. The neutralizing titer is indicated as the concentration of antibody (μg/ml) that gives a 50% reduction of DENV infection.

For identification of the target antigens recognized by the monoclonal antibodies yeasts displaying Dengue virus E protein domains III or domain I-II were stained with the monoclonal antibodies followed by Cy5-labeled goat anti human IgG antibodies and analyzed by FACS. Western blotting experiments were performed using lysates of DENV-infected cells.

Table 3 shows that three different types of antibodies have been identified. They include those that are specific for domain III (DIII) of E protein, those that are specific for domains I-II (DI-II) of E protein and those specific for prM. The antibodies show different degrees of cross-reactivity with the 4 different DENV serotypes and neutralize those serotypes to which they bind.

TABLE 3

Target Antigen Specificity of Neutralizing anti-Dengue Virus Antibodies

| Antibody | Target Antigen | Dengue Virus Serotypes Neutralized |
|---|---|---|
| HMB-DV-1 | E, DIII | 1, 2, 3 |
| HMB-DV-2 | E, DIII | 1, 3 |
| HMB-DV-3 | prM | 1, 2, 3, 4 |
| HMB-DV-4 | E, DI-II | 1, 2, 3, 4 |
| HMB-DV-5 | E, DI-II | 1, 2, 3, 4 |
| HMB-DV-6 | E, DIII | 1, 2, 3 |
| HMB-DV-7 | E, DIII | 1, 2, 3 |
| HMB-DV-8 | E | 4 |
| HMB-DV-9 | E, DIII | 2 |
| HMB-DV-10 | E, DIII | 1, 2, 3, 4 |
| HMB-DV-11 | E, DIII | 1, 2, 3, 4 |

TABLE 3-continued

Target Antigen Specificity of Neutralizing anti-Dengue Virus Antibodies

| Antibody | Target Antigen | Dengue Virus Serotypes Neutralized |
|---|---|---|
| HMB-DV-12 | E, DI-DII | 2 |
| HMB-DV-13 | E, DIII | 1, 2, 3, 4 |
| HMB-DV-14 | E, DIII | 2 |

Table 4 shows the results of virus neutralization assays on VERO cells and DC-SIGN-transfected Raji cells.

TABLE 4

Neutralization of Dengue Virus (serotypes DENV1-DENV4) by Antibodies

| Antibody | Cell type | Neutralization $EC_{50}$ values (μg/ml) | | | |
|---|---|---|---|---|---|
| | | DENV1 | DENV2 | DENV3 | DENV4 |
| HMB-DV-1 | VERO | 0.013 | 0.577 | 0.014 | >20 |
| | DC-SIGN-Raji | 0.032 | 5.340 | 0.055 | >20 |
| HMB-DV-2 | VERO | 0.006 | >20 | 0.006 | >20 |
| | DC-SIGN-Raji | 0.014 | >20 | 0.013 | >20 |
| HMB-DV-3 | VERO | 0.912 | 1.615 | 0.120 | 0.070 |
| | DC-SIGN-Raji | ND | ND | ND | ND |
| HMB-DV-4 | VERO | 0.591 | 0.251 | 0.809 | 0.367 |
| | DC-SIGN-Raji | 2.250 | 1.370 | 0.613 | >20 |
| HMB-DV-5 | VERO | 0.066 | 0.034 | 0.118 | 0.200 |
| | DC-SIGN-Raji | 2.390 | 0.504 | 0.348 | >20 |
| HMB-DV-6 | VERO | 0.008 | 0.002 | 0.011 | >20 |
| | DC-SIGN-Raji | 0.027 | 0.440 | 0.332 | >20 |
| HMB-DV-7 | VERO | 0.016 | 0.004 | 0.020 | >20 |
| | DC-SIGN-Raji | ND | ND | ND | ND |
| HMB-DV-8 | VERO | >20 | >20 | >20 | 0.006 |
| | DC-SIGN-Raji | ND | ND | ND | ND |
| HMB-DV-9 | VERO | >20 | 0.002 | >20 | >20 |
| | DC-SIGN-Raji | ND | ND | ND | ND |
| HMB-DV-10 | VERO | >20 | 0.084 | >20 | 0.466 |
| | DC-SIGN-Raji | ND | ND | ND | ND |
| HMB-DV-11 | VERO | >20 | 0.048 | >20 | 0.520 |
| | DC-SIGN-Raji | ND | ND | ND | ND |
| HMB-DV-12 | VERO | ND | 0.003 | ND | ND |
| | DC-SIGN-Raji | ND | ND | ND | ND |
| HMB-DV-13 | VERO | 0.993 | 3.326 | 1.513 | >20 |
| | DC-SIGN-Raji | ND | ND | ND | ND |
| HMB-DV-14 | VERO | >20 | 0.002 | >20 | >20 |
| | DC-SIGN-Raji | ND | ND | ND | ND |

ND: not determined

Example 3

Neutralizing Recombinant Anti-Dengue Virus Antibodies with Mutations in the Fc Region do not Cause Enhancement of Virus Infection on K562 Cells Antibody-dependent enhancement (ADE) of dengue virus infection has been described in the literature. This property could limit the therapeutic effectiveness of anti-dengue virus antibodies for use in clinical situations. Therefore, mRNAs from the immortalized B cell lines expressing antibodies HMB-DV-5, HMB-DV-6 and HMB-DV-8 were isolated, cDNA was synthesized using oligo-dT specific primers, variable regions of heavy and light chain were sequenced and cloned into an expression vector using specific primers. Vectors were transfected into host cells for recombinant expression. In addition to recombinant production of the wild-type IgG1 antibodies, each of the heavy chains was mutated at amino acids 4 and 5 of CH2 domain by substituting an alanine in place of the natural leucine using site-directed mutagenesis thereby creating the LALA variant of each antibody. Both recombinant wild type and mutated antibodies were harvested from the expression cell lines and purified. Both wild-type IgG1 anti-dengue virus antibody and the LALA variant bound to the target protein in comparable manner (data not shown).

Virus neutralization and enhancement was determined as above on VERO cells and K562 cells. Each of the three antibodies has a defined molecular target as well as serotype target (see Table 3). FIG. 1 shows that the unmodified recombinant antibodies neutralize target virus infection of VERO cells in a dose-dependent manner (DOTTED LINES). On K562 cells, a cell line that is not efficiently infected by Dengue viruses, the unmodified antibodies show an enhancement of viral infection at concentrations that are generally higher that those required for neutralization (SOLID LINES). The experiment was repeated using the LALA variants of each antibody. FIG. 2 shows that each of the LALA variants of the recombinant anti-dengue virus antibodies also neutralized the target virus on VERO cells (DOTTED LINES) in a dose-dependent manner. However, each of the LALA antibodies did not show evidence of antibody-dependent enhancement of infection on K562 cells (SOLID LINES). Note, the dose-response is flat on the K562 cells at the concentrations of antibodies used in this experiment and the line appears very close to the X-axis.

All patents and publications referred to herein are expressly incorporated by reference in their entirety.

It should be noted that there are alternative ways of implementing the present invention and that various modifications can be made without departing from the scope and spirit of the invention. Accordingly, the present embodiments are to be considered as illustrative and not restrictive, and the invention is not to be limited to the details given herein, but may be modified within the scope and equivalents of the appended claims.

REFERENCES (THE CONTENTS OF WHICH ARE HEREBY INCORPORATED BY REFERENCE)

[1] Lefranc et al. (2003) *Dev Comp Immunol.* 27(1):55-77.
[2] Lefranc et al. (1997) *Immunology Today,* 18:509.
[3] Lefranc (1999) *The Immunologist,* 7:132-136.
[4] U.S. Pat. No. 4,676,980
[5] U.S. Pat. No. 4,831,175
[6] U.S. Pat. No. 5,595,721
[7] WO00/52031
[8] WO00/52473
[9] U.S. Pat. No. 4,766,106
[10] U.S. Pat. No. 4,179,337
[11] U.S. Pat. No. 4,495,285
[12] U.S. Pat. No. 4,609,546
[13] Knauf et al. (1988) *J. Bio. Chem.* 263:15064-15070
[14] Gabizon et al. (1982) *Cancer Research* 42:4734
[15] Cafiso (1981) *Biochem Biophys Acta* 649:129
[16] Szoka (1980) *Ann. Rev. Biophys. Eng.* 9:467
[17] Poznansky et al. (1980) *Drug Delivery Systems* (R. L. Juliano, ed., Oxford, N.Y.) pp. 253-315
[18] Poznansky (1984) *Pharm Revs* 36:277
[19] Kohler, G. and Milstein, C., 1975, *Nature* 256:495-497.
[20] Kozbar et al. 1983, *Immunology Today* 4:72.
[21] WO2004/076677
[22] Chapter 4 of *Kuby Immunology* (4th edition, 2000; ASIN: 0716733315
[23] Jones et al. *Biotechnol Prog* 2003, 19(1):163-8
[24] Cho et al. *Cytotechnology* 2001, 37:23-30
[25] Cho et al. *Biotechnol Prog* 2003, 19:229-32
[26] U.S. Pat. No. 5,807,715
[27] U.S. Pat. No. 6,300,104
[28] Traggiai et al. (2004) *Nat Med* 10(8):871-875

SEQ ID List

| SEQ ID | mAb | Description | Sequence |
|---|---|---|---|
| 1 | HMB-DV-1 | CDRH1 aa | GFSFSSSS |
| 2 | | CDRH2 aa | ISTSGNYI |
| 3 | | CDRH3 aa | ARDPCSSTTCYFGYYAMDV |
| 4 | | CDRL1 aa | NIGSKT |
| 5 | | CDRL2 aa | RDT |
| 6 | | CDRL3 aa | QVWDGTSVV |
| 7 | | CDRH1 nuc | ggattcagctttagtagctctagc |
| 8 | | CDRH2 nuc | atcagtactagtggtaattacatc |
| 9 | | CDRH3 nuc | gcgagagatccctgtagtagtaccacgtgctattttggttattacgctatggacgt |
| 10 | | CDRL1 nuc | aatattggaagtaaaact |
| 11 | | CDRL2 nuc | agggatacc |
| 12 | | CDRL3 nuc | caggtgtgggacggcacttctgtggtg |
| 13 | | heavy ch aa | EVQLVESGGGLVKPGGSLRLSCTASGFSFSSSSMNWV RQAPGKGLQWVSYISTSGNYIYYADSVKGRFTISRDN AKNSVYLQMNSLRVEDTAVYYCARDPCSSTTCYFGY YAMDVWGQGTTVAVSS |

SEQ ID List

| SEQ ID | mAb | Description | Sequence |
|---|---|---|---|
| 14 | | light ch aa | SYELTQPLSVSVALGQTARVTCGGNNIGSKTVHWYQ QRPGQAPVLVIYRDTNRPSGIPERFSGSKSGSAATLTIS RAQAGDEAEYYCQVWDGTSVVFGGGTKLTVL |
| 15 | | heavy ch nuc | gaggtgcagctggtgcagtctgggggaggcctggtcaagccggggggtccctga gactctcctgtacagcctctggattcagctttagtagctctagcatgaactgggtccgc caggctccagggaaggggctgcagtgggtctcatacatcagtactagtggtaattac atctactacgcagactcagtgaagggccgattcaccatctccagagacaacgccaag aactcagtgtatctgcaaatgaacagctgagagtcgaggacacggctgtgtattact gtgcgagagatccctgtagtagtaccacgtgctattttggttattacgctatggacgtct ggggccaagggaccacggtcgccgtctcctcag |
| 16 | | light ch nuc | tcctatgagctgactcagccactctctgtgtcagtggccctgggacagacggccagg gttacctgtgggggaaacaatattggaagtaaaactgtgcactggtaccagcagagg ccaggccaggcccctgtgctggtcatttataggggataccaaccggccctctgggatc cctgagcgattctctggctccaagtcggggagcgcggccaccctgaccatcagcag agcccaagccggggatgaggctgagtattactgccaggtgtgggacggcacttctgt ggtgttcggcggagggaccaagctgaccgtcctag |
| 17 | HMB-DV-2 | CDRH1 aa | GGSISSASYY |
| 18 | | CDRH2 aa | IYTSGST |
| 19 | | CDRH3 aa | AREWAARGGIVDY |
| 20 | | CDRL1 aa | QSISYY |
| 21 | | CDRL2 aa | GAS |
| 22 | | CDRL3 aa | QQSYDFPRT |
| 23 | | CDRH1 nuc | ggtggctccatcagcagtgctagttactac |
| 24 | | CDRH2 nuc | atctataccagcgggagcacc |
| 25 | | CDRH3 nuc | gcgagagagtgggcagctcggggggcattgttgactac |
| 26 | | CDRL1 nuc | cagagcattagttactat |
| 27 | | CDRL2 nuc | ggtgcatcc |
| 28 | | CDRL3 nuc | caacaaagttacgattttcctcggacg |
| 29 | | heavy ch aa | QVQLQESGPTLVKPSQTLSLTCSVSGGSISSASYYWSW IRQPAGKGLEWIGQIYTSGSTKYNPSLKSRLTLSMDTS KNQFTLKLSSVTAADTALYYCAREWAARGGIVDYW GQGTLVTVSS |
| 30 | | light ch aa | DIQMTQSPSSLSASVGDRVTITCRASQSISYYLNWYQQ KPGKAPKVLIYGASSLQSGVPSRFSGSGSETDFTLTISS LQPEDEATYYCQQSYDEPRTEGQGTKVEIK |
| 31 | | heavy ch nuc | caggtgcagctgcaggagtcggggccaacactggtgaagccttcacagaccctgtc cctcacctgcagtgtctctggtggctccatcagcagtgctagttactactggagctgga tccggcagcccgccgggaagggactggagtggattgggcaaatctataccagcgg gagcaccaagtacaaccctcctcaagagtcgactcaccctgtcaatggacacgtc caagaaccagttcaccctgaagctgagctctgtgaccgccgcagatacggccttatat tattgcgcgagagagtgggcagctcggggggcattgttgactactggggccaggg aaccctggtcaccgtctcctcag |
| 32 | | light ch nuc | gacatccagatgacccagtctccatcctccctgtctgcatctgtaggagacagagtca ccatcacttgccgagcaagtcagagcattagttactatttaaattggtatcagcagaaa cccgggaaagcccctaaggtcctgatctatggtgcatccagtttgcaaagcggggtc ccatcaaggttcagtggcagtggatctgagacagatttcactctcaccatcagcagtct gcaacctgaagattttgcaacttactactgtcaacaaagttacgattttcctcggacgttc ggccaagggaccaaggtggaaatcaagc |
| 33 | HMB-DV-3 | CDRH1 aa | GGSISSSGYS |
| 34 | | CDRH2 aa | ISASGTT |
| 35 | | CDRH3 aa | ARDTECSDTSCFPSIWFDT |
| 36 | | CDRL1 aa | NIGTKG |

SEQ ID List

| SEQ ID | mAb | Description | Sequence |
|---|---|---|---|
| 37 | | CDRL2 aa | YDS |
| 38 | | CDRL3 aa | QVWDNTDDSSDHPV |
| 39 | | CDRH1 nuc | ggtggctccatcagcagtagtggttactcc |
| 40 | | CDRH2 nuc | atttctgccagtgggaccacc |
| 41 | | CDRH3 nuc | gcgagggatacggagtgtagtgatacgagttgcttttccctccatctggttcgatacc |
| 42 | | CDRL1 nuc | aacattggaactaaaggt |
| 43 | | CDRL2 nuc | tatgatagc |
| 44 | | CDRL3 nuc | caggtgtgggataatactgatgacagtagtgatcacccggtg |
| 45 | | heavy ch aa | QVQLQESGPGLVKSSQTLSLTCTVSGGSISSSGYSWN WIRQPAGKGLEWIGRISASGTTNYNPSVKSRGTVSVD TSKNQFSLRLTSVTAADTAVYYCARDTECSDTSCFPSI WFDTWGQGALVTVSS |
| 46 | | light ch aa | SYELTQPPSVSVAPGKTATITCGGNNIGTKGVHWYQR KAGQAPVLVIYYDSVRPSGIPERFSGSNSGNTATLTISR VEAGDEADYYCQVWDNTDDSSDHPVFGGGSKLTVL |
| 47 | | heavy ch nuc | caggtgcagctgcaggagtcgggcccaggactggtgaagagttcacagaccctgtc cctcacctgcactgtctctggtggctccatcagcagtagtggttactcctggaactgga tccggcagcccgccgggaagggactggagtggattgggcgtatttctgccagtggg accaccaactacaacccctcgtcaagagtcgaggcactgtttcagtagacacgtcc aagaaccagttctcctgaggctgacctctgttaccgccgcggacacggccgtttact attgtgcgagggatacggagtgtagtgatacgagttgcttttccctccatctggttcgata cctggggccagggagccctggtcaccgtctcctcag |
| 48 | | light ch nuc | tcctatgtgctgactcagccaccctcagtgtcagtggccccaggaaagacggccacc attacctgtggggggaaacaacattggaactaaaggtgtgcactggtaccagcggaag gcaggccaggcccctgtgttggtcatctattatgatagcgtccggccctcagggatcc ctgagcgcttctctctggctccaactctgggaacacggccacccctgaccatcagcaggg tcgaagccggggatgaggccgactattactgtcaggtgtgggataatactgatgaca gtagtgatcacccggtgttcggcggagggtccaagctgaccgtcctag |
| 49 | HMB-DV-4 | CDRH1 aa | SGSISTSDYY |
| 50 | | CDRH2 aa | VYYSEST |
| 51 | | CDRH3 aa | ARQRGNWFDS |
| 52 | | CDRL1 aa | QGISNY |
| 53 | | CDRL2 aa | AAS |
| 54 | | CDRL3 aa | QQLNNYEFT |
| 55 | | CDRH1 nuc | agtggctccatcagcactagtgattactac |
| 56 | | CDRH2 nuc | gtctattatagtgagagcacc |
| 57 | | CDRH3 nuc | gccagacaacgaggaaactggttcgactcc |
| 58 | | CDRL1 nuc | cagggcattagcaattat |
| 59 | | CDRL2 nuc | gctgcatcc |
| 60 | | CDRL3 nuc | caacaacttaataattacgaattcact |
| 61 | | heavy ch aa | QLQMHESGPGLVKPSETLSLTCIVSSGSISTSDYYWGW IRQPPGKGLEWIGSVYYSESTYYSPSLKSRITISVDTSR NQFSLNVSSVTAADTAIYFCARQRGNWFDSWGQGTL VTVSS |
| 62 | | light ch aa | AIQLTQSPSSLSASVGDRVTITCRASQGISNYLAWYQQ KPGKAPKLLIYAASTLQSGVPSRFSGSGSGTDFTLTISS LQPEDFATYYCQQLNNYEFTFGPGTKVDIK |

SEQ ID List

| SEQ ID | mAb | Description | Sequence |
|---|---|---|---|
| 63 | | heavy ch nuc | cagctgcagatgcacgagtcgggcccaggactggtgaagccttcggagaccctgtc<br>cctcacgtgcattgtctctagtggctccatcagcactagtgattactactggggctggat<br>ccgccagccccccagggaaggggctggagtggattgggagtgtctattatagtgaga<br>gcacctactacagtccgtccctcaagagtcgaatcaccatatccgtagacacgtccag<br>gaaccagttctccctgaacgtgagttctgtgaccgccgcagacacggctatatatttct<br>gtgccagacaacgaggaaactggttcgactcctggggccagggaaccctggtcacc<br>gtctcctcag |
| 64 | | light ch nuc | gccatccagttgacccagtctccatcctccctatctgcatctgtaggagacagagtcac<br>catcacttgccgggccagtcagggcattagcaattatttagcctggtatcagcaaaaa<br>ccagggaaagcccctaagctcctgatctatgctgcatccactttgcaaagtggggtcc<br>catcaaggttcagcggcagtggctctgggacagatttcactctcaccatcagcagcct<br>gcagcctgaagattttgcaacttattactgtcaacaacttaataattacgaattcactt<br>tcggccctgggaccaaagtggatatcaaac |
| 65 | | heavy ch var1 aa | QLQMHESGPGLVKPSETLSLTCTVSSGSISTSDYYWG<br>WIRQPPGKGLEWIGSVYYSESTYYSPSLKSRITISVDTS<br>RNQFSLNVSSVTAADTAIYFCARQRGNWFDSWGQGT<br>LVTVSS |
| 66 | | heavy ch var1 nuc | cagctgcagatgcacgagtcgggcccaggactggtgaagccttcggagaccctgtc<br>cctcacgtgcactgtctctagtggctccatcagcactagtgattactactgggggctgga<br>tccgccagccccccagggaaggggctggagtggattgggagtgtctattatagtgaga<br>gcacctactacagtccgtccctcaagagtcgaatcaccatatccgtagacacgtccag<br>gaaccagttctccctgaacgtgagttctgtgaccgccgcagacacggctatatatttct<br>gtgccagacaacgaggaaactggttcgactcctggggccagggaaccctggtcacc<br>gtctcctcag |
| 67 | HMB-DV-5 | CDRH1 aa | AFNFSTNA |
| 68 | | CDRH2 aa | ISYDGSHK |
| 69 | | CDRH3 aa | ATVGVLTWPVNAEYFHH |
| 70 | | CDRL1 aa | SSNIGAGYD |
| 71 | | CDRL2 aa | GNN |
| 72 | | CDRL3 aa | QSYDSSLTGVV |
| 73 | | CDRH1 nuc | gcattcaacttcagtaccaatgcc |
| 74 | | CDRH2 nuc | atatcatatgatggaagccataaa |
| 75 | | CDRH3 nuc | gcgacagtgggagtccttacatggcccgtcaacgctgagtactttcaccac |
| 76 | | CDRL1 nuc | agctccaacatcggggcaggttatgat |
| 77 | | CDRL2 nuc | ggtaacaac |
| 78 | | CDRL3 nuc | cagtcctatgacagcagcctgactggtgtggta |
| 79 | | heavy ch aa | QAHLVESGGGVVQPGRSLRLSCAASAFNFSTNAMHW<br>VRQAPGKGLEWVAVISYDGSHKYYADSVKGRFTISR<br>DNSKNTLYLQMNSLRAADTAVYYCATVGVLTWPVN<br>AEYFHHWGQGSLVSVSS |
| 80 | | light ch aa | QSVLTQPPSVSGAPGQRVTISCTGSSSNIGAGYDVHW<br>YQQLPGTAPKLLICGNNNRPSGVPDRFSGSKSGTSASL<br>AITGLQAEDEADYYCQSYDSSLTGVVFGGGTKLTVL |
| 81 | | heavy ch nuc | caggcgcacctggtggaatctgggggaggcgtggtccagcctggaggtccctga<br>gactctcctgtgcagcctctgcattcaacttcagtaccaatgccatgcactgggtccgc<br>caggctccaggcaaggggctggaatgggtggcagtaatatcatatgatggaagcca<br>taaatactacgcagactccgtgaagggccgattcaccatctccagagacaattccaag<br>aacacgctgtatctgcaaatgaacagcctgagagcggcggacacggctgtctattac<br>tgtgcgacagtgggagtccttacatggcccgtcaacgctgagtactttcaccactggg<br>gccagggctccctggtcagcgtctcttcag |
| 82 | | light ch nuc | cagtctgtgctgacgcagccgccctcagtgtctggggcccccagggcagagggtcac<br>catctcctgcactgggagcagctccaacatcggggcaggttatgatgtacactggtac<br>cagcagcttcctggaacagcccccaaactcctcatctgtggtaacaacaatcggccct<br>caggagtccctgaccgattctctggctccaagtctggcacctcagcctcctggccat<br>cactgggctccaggctgaggatgaggctgattattattgccagtcctatgacagcagc<br>ctgactggtgtggtattcggcggagggaccaagctgaccgtcctag |

-continued

SEQ ID List

| SEQ ID | mAb | Description | Sequence |
|---|---|---|---|
| 83 | HMB-DV-6 | CDRH1 aa | GFTFDDYA |
| 84 | | CDRH2 aa | ISWNSATI |
| 85 | | CDRH3 aa | AKGGPRGLQLLSSWVDY |
| 86 | | CDRL1 aa | QDIRRY |
| 87 | | CDRL2 aa | TTS |
| 88 | | CDRL3 aa | QQSYSPPHT |
| 89 | | CDRH1 nuc | ggattcacgtttgatgattatgcc |
| 90 | | CDRH2 nuc | attagttggaatagtgccaccata |
| 91 | | CDRH3 nuc | gcgaaggggcccctaggggctgcaactgctatcatcgtgggtcgactac |
| 92 | | CDRL1 nuc | caggacattcgcaggtat |
| 93 | | CDRL2 nuc | actacatcc |
| 94 | | CDRL3 nuc | caacagagttacagtcccctcacact |
| 95 | | heavy ch aa | EVQLVESGGGLVQPGRSLRLSCAASGFTFDDYAMFW VRQAPGKGLEWISGISWNSATIGYADSVKGRFTISRDN AKKSLDLQMNSLRPDDTALYYCAKGGPRGLQLLSSW VDYWGQGTLVTVSS |
| 96 | | light ch aa | DIQMTQSPSSLSASVGDRVTITCRASQDIRRYLNWYQ QRPGRVPQLLIYTTSTLQSGVPSRFSGSGSVTDFTLTIS SLQPEDFGTYYCQQSYSPPHTFGQGTKLEIK |
| 97 | | heavy ch nuc | gaagtgcagctggtggagtctggggg aggcttggtacagcctggcaggtccctgag actctcctgtgcagcctctggattcacgtttgatgattatgccatgttctgggtccggca agctccaggaagggcctggaatggatctcaggtattagttggaatagtgccaccat aggctatgcggactctgtgaagggccgattcaccatctccagagacaacgccaaga agtccctggatctgcagatgaatagtctgagacctgatgacacggccttatattattgtg cgaaggggcccctaggggctgcaactgctatcatcgtgggtcgactactggggc cagggaaccctggtcaccgtctcctcgg |
| 98 | | light ch nuc | gacatccagatgacccagtctccgtcctccctgtctgcgtctgttggggacagagtca ccatcacttgccgggcaagtcaggacattcgcaggtatttgaattggtatcagcagag accagggagagtccctcagctcctgatctatactacatccactctccaaagtggggtc ccatccaggttcagtggcagtggatctgtgacagatttcactctcaccatcagcagtct gcaacctgaagattttggaacttactactgtcaacagagttacagtcccctcacacttt tggccaggggaccaagctggagatcaagc |
| 99 | HMB-DV-7 | CDRL1 aa var1 | QGISNW |
| 53 | | CDRL2 aa var1 | AAS |
| 100 | | CDRL3 aa var1 | QQANSFPPT |
| 101 | | CDRL1 nuc var1 | cagggtattagcaactgg |
| 59 | | CDRL2 nuc var1 | gctgcatcc |
| 102 | | CDRL3 nuc var1 | cagcaggctaacagtttccctccgacg |
| 103 | | light ch aa var1 | DILMTQSPSFVSASVGDRVTITCRASQGISNWLAWYQ QKPGKAPNLLISAASSLQSGVPSRFSGSGSGTDFTLTIS SLQPEDFATYFCQQANSFPPTFGQGTKVESK |
| 104 | | light ch nuc var1 | gacatcctcatgacccagtctccatctttcgtgtctgcatctgtaggagacagagtcac catcacttgtcgggcgagtcagggtattagcaactggttagcctggtatcagcagaaa ccagggaaagcccctaacctcctgatctctgctgcatccagtttgcaaagtggggtcc |

SEQ ID List

| SEQ ID | mAb | Description | Sequence |
|---|---|---|---|
| | | | catcaaggttcagcggcagtggatctgggacagatttcactctcaccatcagcagcct gcagcctgaagattttgcaacttacttttgtcagcaggctaacagtttccctccgacgtt cggccaagggaccaaggtggaaagcaaac |
| 105 | HMB-DV-8 | CDRH1 aa | GFTFSRYD |
| 106 | | CDRH2 aa | ITTAGDT |
| 107 | | CDRH3 aa | ARGPPTDCSSGRCLGVGVGLDP |
| 108 | | CDRL1 aa | KLGKKY |
| 109 | | CDRL2 aa | QDT |
| 110 | | CDRL3 aa | QAWDSTTHVI |
| 111 | | CDRH1 nuc | ggattcaccttcagtaggtacgac |
| 112 | | CDRH2 nuc | attactactgctggtgacaca |
| 113 | | CDRH3 nuc | gcaagagggccccccgaccgattgtagtagtggtcgctgcttaggggtcggagtggg gcttgacccc |
| 114 | | CDRL1 nuc | aaattggggaaaaaatat |
| 115 | | CDRL2 nuc | caagatacc |
| 116 | | CDRL3 nuc | caggcgtgggacagcaccactcatgtaata |
| 117 | | heavy ch aa | EVQLVESGGGWVQPGGSLRLSCAASGFTFSRYDMHW VRQVTGKGLEWVSAITTAGDTYYPDSVKGRFTISREN AKSSLYLQMNNLRAGDTALYYCARGPPTDCSSGRCL GVGVGLDPWGQGTLVTVSS |
| 118 | | light ch aa | SYEVTQPPSVSVSPGQTASITCSGDKLGKKYTSWYQQ KPGQSPLLVIYQDTKRPSGIPERFSGSNSGNTATLTISG TQAMDEADYYCQAWDSTTHVIFGGGTKLTVL |
| 119 | | heavy ch nuc | gaggtgcagctggttgagtctggggggaggctgggtacagcctggggggtccctga gactctcctgtgcagcctctggattcaccttcagtaggtacgacatgcactgggtccgc caagtcacaggcaaaggtctggagtgggtctcagctattactactgctggtgacacat actatcctgactccgtgaagggccgattcaccatctccagagaaaatgccaagagct ccttgtatcttcaaatgaacaacctgagagccggggacacggctctttattactgtgca agagggccccccgaccgattgtagtagtggtcgctgcttaggggtcggagtggggctt gaccctggggccagggaaccctggtcaccgtctcctcag |
| 120 | | light ch nuc | tcctatgaagtgactcagccaccctcagtgtccgtgtccccaggacagacagccagc atcacctgctctggagataaattggggaaaaaatatacttcctggtatcagcagaagc caggccagtcccctctactggtcatctatcaagataccaagcggccctcagggatcc ctgagcggttctctggctccaactctgggaacacagccactctgaccatcagcggga cccaggctatggatgaggctgactattactgtcaggcgtgggacagcaccactcatg taatattcggcggagggaccaagctgaccgtcctag |
| 121 | HMB-DV-9 | CDRH1 aa | GYTFTNYY |
| 122 | | CDRH2 aa | IDPTGGTT |
| 123 | | CDRH3 aa | ARGGGYSRNWYSYQNYGLDV |
| 70 | | CDRL1 aa | SSNIGAGYD |
| 124 | | CDRL2 aa | GNS |
| 125 | | CDRL3 aa | QSYDSSLSGFV |
| 126 | | CDRH1 nuc | ggatacactttcaccaactactat |
| 127 | | CDRH2 nuc | atcgaccctactggtggtaccacc |
| 128 | | CDRH3 nuc | gcgagaggggggaggatatagtcgcaactggtacagctaccagaattacggtttgga cgtc |
| 76 | | CDRL1 nuc | agctccaacatcggggcaggttatgat |

SEQ ID List

| SEQ ID | mAb | Description | Sequence |
|---|---|---|---|
| 129 | | CDRL2 nuc | ggtaatagc |
| 130 | | CDRL3 nuc | cagtcctatgacagcagcctgagtggttttgtc |
| 131 | | heavy ch aa | QVQLVQSGAEVKKPGASVRLSCKASGYTFTNYYLHW<br>VRQAPGQGLEWMGIIDPTGGTTPYAQKFHGRFTMTS<br>DTSTSTVFMELSSLRLDDTAVYYCARGGGYSRNWYS<br>YQNYGLDVWGRGTTVTVSS |
| 132 | | light ch aa | QAVLTQPPSVSGAPGQRVTISCTGSSSNIGAGYDVHW<br>YQQFPGTAPKLLIYGNSDRPSGVPDRFSGSQSGTSASL<br>AITELQAADEADFYCQSYDSSLSGFVFGTGTKVTVL |
| 133 | | heavy ch nuc | caggtacagctggtacagtctggggctgaggtgaagaagcctggggcctcagtgag<br>gctttcctgtaaggcatctggatacactttcaccaactactatctacactgggtgcgaca<br>ggcccctggacaagggcttgagtggatgggaataatcgaccctactggtggtaccac<br>cccctacgcgcagaagttccatggcagattcaccatgaccagtgacacgtccacgag<br>cacagtcttcatggagttgagcagcctgagattagatgatacggccgtatattactgtg<br>cgagagggggaggatatagtcgcaactggtacagctaccagaattacggtttggac<br>gtctggggccgagggaccacagtcaccgtctcctca |
| 134 | | light ch nuc | caggctgtgctgacgcagccgccctcagtgtctggggcccccaggacagagggtca<br>ccatctcctgcactgggagcagctccaacatcggggcaggttatgatgtacactggta<br>ccagcagtttccaggaacagcccccaaactcctcatttatggtaatagcgatcggccc<br>tcaggggtccctgaccgattctctggctcccagtctggaacttcagcctcctggccat<br>cactgagctccaggctgcggatgaggctgattttactgccagtcctatgacagcagc<br>ctgagtggttttgtcttcggaactgggaccaaggtcaccgtccta |
| 135 | HMB-DV-10 | CDRH1 aa | GFTFNRSW |
| 136 | | CDRH2 aa | IIPDGSEK |
| 137 | | CDRH3 aa | ARVAEFDYVWGSFDF |
| 138 | | CDRL1 aa | KLGYKY |
| 109 | | CDRL2 aa | QDT |
| 139 | | CDRL3 aa | QAWDSRTGV |
| 140 | | CDRH1 nuc | ggtttcacctttaataggtcttgg |
| 141 | | CDRH2 nuc | ataatcccagatggaagtgagaaa |
| 142 | | CDRH3 nuc | gcgagagtggcggagtttgattacgtttgggggagttttgacttc |
| 143 | | CDRL1 nuc | aaattgggatataaatat |
| 115 | | CDRL2 nuc | caagatacc |
| 144 | | CDRL3 nuc | caggcgtgggacagccgcactggggtg |
| 145 | | heavy ch aa | EVQLVESGGGLVQPGGSLRLSCAASGFTFNRSWMNW<br>VRQAPGKGLEWVANIIPDGSEKYYMDSVKGRFTVSR<br>DNTKNSVYLQMNSLRAEDTAVYYCARVAEFDYVWG<br>SFDFWGQGTLVTVSS |
| 146 | | light ch aa | SYELTQTPSVSVSPGHAASITCSGDKLGYKYTSWYQQ<br>KPGQSPVLVIYQDTKRPSGIPERFSGSNSGNTATLTISA<br>TQAMDEADYYCQAWDSRTGVFGGGTKLTVL |
| 147 | | heavy ch nuc | gaggtgcagttggtggagtcgggggggaggcttggtccagcctggggggtccctga<br>gactctcctgtgcagcctctggtttcacctttaataggtcttggatgaactgggtccgcc<br>aggctccagggaaggggctggagtgggtggccaatataatcccagatggaagtga<br>gaaatactatatggactctgtgaagggccgattcaccgtctccagagacaacaccaa<br>gaactcagtgtatctgcaaatgaacagcctgagagccgaggacacggctgtctatta<br>ctgtgcgagagtggcggagtttgattacgtttgggggagttttgacttctggggccag<br>ggaaccctggtcaccgtctcctctg |
| 148 | | light ch nuc | tcctatgagttgactcagacaccctcagtgtccgtgtccccaggacacgcagccagc<br>atcacctgctctggagataaattgggatataaatatacttcctggtatcaacagaagcc<br>aggccagtcccctgtgctggtcatctatcaagataccaagcggcccctcagggatccct<br>gagcgattctctggctccaactctgggaacacagccactctgaccatcagcgcgacc |

| SEQ ID | mAb | Description | Sequence |
|---|---|---|---|
| | | | caggctatggatgaggctgactattactgtcaggcgtgggacagccgcactggggtg ttcggcggagggaccaaactgaccgtcctgg |
| 149 | HMB-DV-11 | CDRH1 aa var1 | GFTFSRSW |
| 150 | | CDRH1 nuc var1 | aaattgggatataaatat |
| 151 | | heavy ch aa var1 | EVQLVESGGGLVQPGGSLRLSCAASGFTFSRSWMNW VRQAPGKGLEWVANIIPDGSEKYYMDSVKGRFTVSR DNTKNSVYLQMNSLRAEDTAVYYCARVAEFDYVWG SFDFWGQGTLVTVSS |
| 152 | | heavy ch nuc var1 | gaggtgcagttggtggagtcggggggaggcttggtccagcctggggggtccctga gactctcctgtgcagcctctggtttcacctttagtaggtcttggatgaactgggtccgcc aggctccagggaaggggctggagtgggtggccaatataatcccagatggaagtga gaaatactatatggactctgtgaagggccgattcaccgtctccagagacaacaccaa gaactcagtgtatctgcaaatgaacagcctgagagccgaggacacggctgtctatta ctgtgcgagagtggcggagtttgattacgtttgggggagttttgacttctggggccag ggaaccctggtcaccgtctcctctg |
| 153 | HMB-DV-12 | CDRH1 aa | GFTFSYAW |
| 154 | | CDRH2 aa | IKSKMNGETT |
| 155 | | CDRH3 aa | ITDPGNAGSASYGMDV |
| 156 | | CDRL1 aa | QSLLHSDGKTY |
| 157 | | CDRL2 aa | EVS |
| 158 | | CDRL3 aa | MQSVQSLG |
| 159 | | CDRH1 nuc | ggattcactttcagttacgcctgg |
| 160 | | CDRH2 nuc | attaaaagcaaaatgaatggcgagacaaca |
| 161 | | CDRH3 nuc | atcacagaccctgggaacgctggttcggcgagttacggaatggacgtt |
| 162 | | CDRL1 nuc | cagagcctcctgcatagtgatggaaagacctat |
| 163 | | CDRL2 nuc | gaagtttcc |
| 164 | | CDRL3 nuc | atgcaaagtgtacagtccctcggt |
| 165 | | heavy ch aa | EEQLVESGGGLVKPGGSLRLSCGASGFTFSYAWMSW VRQAPGKGLEWVARIKSKMNGETTDYAAPVKGRFTI SRDDSKNTLYLQMSSLKTEDTAVYYCITDPGNAGSAS YGMDVWGQGTTVTVSS |
| 166 | | light ch aa | DIVMTQTPLSLSVTPGQPASISCKSSQSLLHSDGKTYL YWYLQKPGQAPQLLIFEVSTRFPGVPHRFSGSGSGTDF TLKISRVEAEDVGVYYCMQSVQSLGFGGGTKVEIK |
| 167 | | heavy ch nuc | gaggagcagctggtggagtctggggggaggcttggtaaagcctggggggtcccttag actctcgtgtggagcctctggattcactttcagttacgcctggatgagttgggtccgcc aggctccaggcaaggggctggagtgggttgcccgtattaaaagcaaaatgaatggc gagacaacagactacgctgcacccgtgaaaggccagattcaccatctcaagagatgat tcaaaaaacacgctgtatctgcaaatgagtagcctgaaaaccgaggacacagccgtc tattattgtatcacagaccctgggaacgctggttcggcgagttacggaatggacgtttg gggccaagggaccacggtcaccgtctcctcag |
| 168 | | light ch nuc | gatattgtgatgacccagactccactctctctgtccgtcaccccctggacagccggcctc catctcctgcaagtctagtcagagcctcctgcatagtgatggaaagacctatttgtattg gtatctgcagaagccaggccaggctccacaactcctgattttttgaagtttccacccggt tccctggagtgccacataggttcagtggcagcgggtcagggacagatttcacactga aaatcagccgggtggaggctgaggatgttggggtttattactgcatgcaaagtgtaca gtccctcggtttcggcggagggaccaaggtggagatcaaac |
| 169 | HMB-DV-13 | CDRH1 aa | GFTFNTFD |
| 170 | | CDRH2 aa | ISGSSSYI |

| SEQ ID | mAb | Description | Sequence |
|---|---|---|---|
| 171 | | CDRH3 aa | SRVLWDSSTGTFDS |
| 172 | | CDRL1 aa | NIGSKS |
| 173 | | CDRL2 aa | DDS |
| 174 | | CDRL3 aa | QVWDSSSGPFVV |
| 175 | | CDRH1 nuc | ggattcaccttcaatacctttgac |
| 176 | | CDRH2 nuc | attagtggtagtagtagttacata |
| 177 | | CDRH3 nuc | tcgagagtgctgtgggacagcagctcgactggcacctttgactct |
| 178 | | CDRL1 nuc | aacattggaagtaaaagt |
| 179 | | CDRL2 nuc | gatgatagc |
| 180 | | CDRL3 nuc | caggtgtgggatagtagtagtggtccttttgtggtt |
| 181 | | heavy ch aa | EVQLVESGGGLVRPGGSLRLSCAASGFTFNTFDMNW VRQAPGRGLEWVSSISGSSSYIYYADSVKGRFTISRDN AKNSLYLQMNSLRAEDTAVYYCSRVLWDSSTGTFD SWGQGTRVTVSS |
| 182 | | light ch aa | SYVLTQPPSVSVAPGQTARITCGGNNIGSKSVHWYQQ KPGQAPVLVVYDDSDRPSGIPERLSGSNSGNTATLTIS RVEAGDEADYYCQVWDSSSGPFVVFGGGTKLTVL |
| 183 | | heavy ch nuc | gaggtgcagctggtggagtctgggggaggcctggtcaggcctggggggtccctga gactctcctgtgcagcctctggattcaccttcaatacctttgacatgaactgggtccgcc aggctccagggaggggctggagtgggtctcatccattagtggtagtagtagttacat atactacgcagactcagtgaagggccgattcaccatctccagagacaacgccaaga actcactgtatctgcaaatgaacagcctgagagccgaggacacggctgtgtattattgt tcgagagtgctgtgggacagcagctcgactggcacctttgactcttgggggcaggga acccgggtcaccgtctcctcag |
| 184 | | light ch nuc | tcctatgtgctgactcagccacccctcggtgtcagtggccccaggacagacgccag gattacctgtgggggaaacaacattggaagtaaaagtgtgcactggtaccagcagaa gccaggccaggcccctgtgctggtcgtctatgatgatagcgaccggccctcagggat ccctgagcgactctctggctccaactctgggaacacggccaccctgaccatcagcag ggtcgaagccggggatgaggccgactattactgtcaggtgtgggatagtagtagtgg tccttttgtggttttcggcggagggaccaagctgaccgtcctag |
| 185 | HMB-DV-14 | CDRH1 aa | GGSVSSGSYY |
| 186 | | CDRH2 aa | IYYSGPT |
| 187 | | CDRH3 aa | ARAFAKNWFDP |
| 188 | | CDRL1 aa | NIGSRN |
| 37 | | CDRL2 aa | YDS |
| 189 | | CDRL3 aa | QVWDGSSDVAI |
| 190 | | CDRH1 nuc | ggtggctccgtcagcagtggtagttactac |
| 191 | | CDRH2 nuc | atctattacagtgggcccacc |
| 192 | | CDRH3 nuc | gcgagagcatttgcgaagaactggttcgacccc |
| 193 | | CDRL1 nuc | aacattggaagtcgaaat |
| 43 | | CDRL2 nuc | tatgatagc |
| 194 | | CDRL3 nuc | caggtgtgggatggtagtagtgatgttgcaatt |
| 195 | | heavy ch aa | QVQLQESGPGLLKASETLSLTCTVSGGSVSSGSYYWT WIRQPPGKGLEWIGYIYYSGPTNYNPSLKSRVTMSVD TSKNQFSLKVRSVTAADTAVYYCARAFAKNVVFDPW GQGTLVTVSS |

| SEQ ID mAb | Description | Sequence |
|---|---|---|
| 196 | light ch aa | SYVLTQPPSVSVAPGKTARITCGGNNIGSRNVHWYQQ<br>KPGQAPVLVIYYDSDRPSGIPERFSGSNSGNTATLTISR<br>VEAGDEADYYCQVWDGSSDVAIFGGGTKLTVL |
| 197 | heavy ch nuc | caggtgcagctgcaggagtcgggcccaggactgctgaaggcttcggagaccctgtc<br>tctcacatgcactgtctctggtggctccgtcagcagtggtagttactactggacctggat<br>ccggcagccccagggaagggactggagtggattggctatatctattacagtgggc<br>ccaccaactacaatccctccctcaagagtcgagtcaccatgtcagtagacacgtccaa<br>gaaccagttctccctgaaggtgaggtctgtgaccgctgcggacacggccgtatattac<br>tgtgcgagagcatttgcgaagaactggttcgacccctggggccagggaaccctggt<br>caccgtctcctcag |
| 198 | light ch nuc | tcctatgtgctgactcagccaccctcagtgtcggtggccccaggaaagacggccag<br>gattacctgtgggggaaacaacattggaagtcgaaatgtacactggtaccagcagaa<br>gccaggccaggcccctgtgttggtcatctattatgatagcgaccggccctcagggatc<br>cctgagcgattctctggctccaactctgggaacacggccaccctgaccatcagcagg<br>gtcgaagccggggatgaggccgactattactgtcaggtgtgggatggtagtagtgat<br>gttgcaattttggcggagggaccaagctgaccgtcctag |

The invention claimed is:

1. An isolated human antibody, or an antigen-binding fragment thereof, that neutralizes a dengue virus of serotypes DENV-1, DENV-2, DENV-3, or DENV-4, wherein the antibody does not contribute to antibody-dependent enhancement of dengue virus infection, wherein the Fc region of said antibody or antigen-binding fragment thereof comprises a CH2 L4A mutation, a CH2 L5A mutation, or both, and wherein the antibody, or the antigen binding fragment thereof, comprises the heavy chain CDR1, CDR2 and CDR3 and the light chain CDR1, CDR2 and CDR3 sequences as set forth in (i) SEQ ID NOs: 1-6, respectively; (ii) SEQ ID NOs: 17-22, respectively; (iii) SEQ ID NOs: 33-38, respectively; (iv) SEQ ID NOs: 49-54, respectively; (v) SEQ ID NOs: 67-72, respectively; (vi) SEQ ID NOs: 83-88, respectively; (vii) SEQ ID NOs: 83-85, 99, 53, and 100, respectively; (viii) SEQ ID NOs: 105-110, respectively; (ix) SEQ ID NOs: 121-123, 70 124, and 125, respectively; (x) SEQ ID NOs: 135-139, and 109, respectively; (xi) SEQ ID NOs: 149, 136-139, and 109, respectively; (xii) SEQ ID NOs: 153-158, respectively; (xiii) SEQ ID NOs: 169-174, respectively; or (xiv) SEQ ID NOs: 185-188 37, and 189, respectively.

2. The antibody of claim 1, wherein the antibody is a monoclonal antibody or a recombinant antibody.

3. The antibody of claim 1, wherein the antibody neutralizes two, three or four different dengue virus serotypes.

4. The antibody of claim 1, or an antigen binding fragment thereof, wherein the antibody comprises (i) a heavy chain variable region having at least 80% sequence identity to the amino acid sequence of SEQ ID NO: 13 and a light chain variable region having at least 90% sequence identity to the amino acid sequence of SEQ ID NO: 14; or (ii) a heavy chain variable region having at least 80% sequence identity to the amino acid sequence of SEQ ID NO: 29 and a light chain variable region having at least 80% sequence identity to the amino acid sequence of SEQ ID NO: 30; or (iii) a heavy chain variable region having at least 80% sequence identity to the amino acid sequence of SEQ ID NO: 45 and a light chain variable region having at least 80% sequence identity to the amino acid sequence of SEQ ID NO: 46; or (iv) a heavy chain variable region having at least 80% sequence identity to the amino acid sequence of SEQ ID NOs: 61 or 65 and a light chain variable region having at least 80% sequence identity to the amino acid sequence of SEQ ID NO: 62; or (v) a heavy chain variable region having at least 80% sequence identity to the amino acid sequence of SEQ ID NO: 79 and a light chain variable region having at least 80% sequence identity to the amino acid sequence of SEQ ID NO: 80; or (vi) a heavy chain variable region having at least 80% sequence identity to the amino acid sequence of SEQ ID NO: 95 and a light chain variable region having at least 80% sequence identity to the amino acid sequence of SEQ ID NO: 96; or (vii) a heavy chain variable region having at least 80% sequence identity to the amino acid sequence of SEQ ID NO: 95 and a light chain variable region having at least 80% sequence identity to the amino acid sequence of SEQ ID NO: 103; or (viii) a heavy chain variable region having at least 80% sequence identity to the amino acid sequence of SEQ ID NO: 117 and a light chain variable region having at least 80% sequence identity to the amino acid sequence of SEQ ID NO: 118; or (ix) a heavy chain variable region having at least 80% sequence identity to the amino acid sequence of SEQ ID NO: 131 and a light chain variable region having at least 80% sequence identity to the amino acid sequence of SEQ ID NO: 132; or (x) a heavy chain variable region having at least 80% sequence identity to the amino acid sequence of SEQ ID NO: 145 and a light chain variable region having at least 80% sequence identity to the amino acid sequence of SEQ ID NO: 146; or (xi) a heavy chain variable region having at least 80% sequence identity to the amino acid sequence of SEQ ID NO: 151 and a light chain variable region having at least 80% sequence identity to the amino acid sequence of SEQ ID NO: 146; or (xii) a heavy chain variable region having at least 80% sequence identity to the amino acid sequence of SEQ ID NO: 165 and a light chain variable region having at least 80% sequence identity to the amino acid sequence of SEQ ID NO: 166; or (xiii) a heavy chain variable region having at least 80% sequence identity to the amino acid sequence of SEQ ID NO: 181 and a light chain variable region having at least 80% sequence identity to the amino acid sequence of SEQ ID NO: 182; or (xiv) a heavy chain variable region having at least 80% sequence identity to the amino acid sequence of SEQ ID NO: 195 and a light chain variable region having at least 80% sequence identity to the amino acid sequence of SEQ ID NO: 196.

5. The antibody of claim 1, or an antigen binding fragment thereof, wherein the antibody comprises a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 45 and a light chain variable region comprising the amino acid sequence of SEQ ID NO: 46; or a heavy chain variable region comprising the amino acid sequence of SEQ ID NO: 61 and a light chain variable region comprising the amino acid sequence of SEQ ID NO: 62; or a heavy chain variable region comprising the amino acid sequence of SEQ ID NO: 65 and a light chain variable region comprising the amino acid sequence of SEQ ID NO: 62; or a heavy chain variable region comprising the amino acid sequence of SEQ ID NO: 79 and a light chain variable region comprising the amino acid sequence of SEQ ID NO: 80; or a heavy chain variable region comprising the amino acid sequence of SEQ ID NO: 95 and a light chain variable region comprising the amino acid sequence of SEQ ID NO: 96; or a heavy chain variable region comprising the amino acid sequence of SEQ ID NO: 95 and a light chain variable region comprising the amino acid sequence of SEQ ID NO: 103; or a heavy chain variable region comprising the amino acid sequence of SEQ ID NO: 117 and a light chain variable region comprising the amino acid sequence of SEQ ID NO: 118; or a heavy chain variable region comprising the amino acid sequence of SEQ ID NO: 131 and a light chain variable region comprising the amino acid sequence of SEQ ID NO: 132; or a heavy chain variable region comprising the amino acid sequence of SEQ ID NO: 145 and a light chain variable region comprising the amino acid sequence of SEQ ID NO: 146; or a heavy chain variable region comprising the amino acid sequence of SEQ ID NO: 151 and a light chain variable region comprising the amino acid sequence of SEQ ID NO: 146; or a heavy chain variable region comprising the amino acid sequence of SEQ ID NO: 165 and a light chain variable region comprising the amino acid sequence of SEQ ID NO: 166; or a heavy chain variable region comprising the amino acid sequence of SEQ ID NO: 181 and a light chain variable region comprising the amino acid sequence of SEQ ID NO: 182; or a heavy chain variable region comprising the amino acid sequence of SEQ ID NO: 195 and a light chain variable region comprising the amino acid sequence of SEQ ID NO: 196.

6. The antibody of claim 1 or 5, wherein the antibody or antibodies are selected from the group consisting of HMB-DV-1, HMB-DV-2, HMB-DV-3, HMB-DV-4, HMB-DV-5, HMB-DV-6, HMB-DV-7, HMB-DV-8, HMB-DV-9, HMB-DV-10, HMB-DV-11, HMB-DV-12, HMB-DV-13, and HMB-DV-14.

7. The antibody of claim 1, or an antigen binding fragment thereof, wherein the antibody is a monoclonal antibody, a single chain antibody, Fab, Fab', F(ab')2, Fv or scFv.

8. An isolated immortalised B cell clone expressing the antibody of claim 1.

9. A pharmaceutical composition comprising the antibody of claim 1, or an antigen binding fragment thereof, a nucleic acid molecule comprising a polynucleotide encoding said antibody, or an antigen binding fragment thereof; a vector comprising said polynucleotide; a cell expressing said vector, and a pharmaceutically acceptable diluent or carrier and, optionally, an agent useful for extending the half life of the antibody or antigen binding fragment thereof.

10. The pharmaceutical composition of claim 9, wherein the pharmaceutical composition comprises antibody HMB-DV-5, antibody HMB-DV-6, or antibody HMB-DV-8, or antigen binding fragments thereof.

11. The pharmaceutical composition of claim 9, wherein the pharmaceutical composition comprises: (i) antibody HMB-DV-5, or an antigen binding fragment thereof, in addition to antibody HMB-DV-6, or antigen binding fragment thereof; (ii) antibody HMB-DV-5, or an antigen binding fragment thereof, in addition to antibody HMB-DV-8, or an antigen binding fragment thereof; (iii) antibody HMB-DV-6, or an antigen binding fragment thereof, in addition to antibody HMB-DV-8, or an antigen binding fragment thereof; or (iv) antibody HMB-DV-5, or an antigen binding fragment thereof, in addition to antibody HMB-DV-6, or an antigen binding fragment thereof, in addition to antibody HMB-DV-8, or an antigen binding fragment thereof.

* * * * *